(12) United States Patent
Webler et al.

(10) Patent No.: US 8,187,324 B2
(45) Date of Patent: May 29, 2012

(54) TELESCOPING APPARATUS FOR DELIVERING AND ADJUSTING A MEDICAL DEVICE IN A VESSEL

(75) Inventors: William E. Webler, Escondido, CA (US); Daniel L. Cox, Palo Alto, CA (US); Richard Newhauser, San Francisco, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 1454 days.

(21) Appl. No.: 11/445,694

(22) Filed: Jun. 1, 2006

(65) Prior Publication Data

US 2007/0213812 A1    Sep. 13, 2007

Related U.S. Application Data

(63) Continuation-in-part of application No. 10/295,714, filed on Nov. 15, 2002, now Pat. No. 7,485,143, and a continuation-in-part of application No. 10/464,132, filed on Jun. 17, 2003, now abandoned, which is a continuation-in-part of application No. 10/295,714, application No. 11/445,694, which is a continuation-in-part of application No. 11/112,546, filed on Apr. 22, 2005, and a continuation-in-part of application No. 11/008,902, filed on Dec. 10, 2004, now Pat. No. 7,981,152, and a continuation-in-part of application No. 10/740,360, filed on Dec. 17, 2003, now Pat. No. 7,828,819, which is a continuation-in-part of application No. 10/295,714.

(51) Int. Cl.
*A61F 2/24* (2006.01)
(52) U.S. Cl. ...................................... 623/2.37
(58) Field of Classification Search .............. 623/1.11, 623/1.12, 1.23, 2.36, 2.37
See application file for complete search history.

(56) References Cited

U.S. PATENT DOCUMENTS

| | | | |
|---|---|---|---|
| 3,177,543 A | 11/1962 | Fountain |
| 3,716,058 A | 2/1973 | Tanner, Jr. |
| 3,804,097 A | 4/1974 | Rudie |
| 4,072,146 A | 2/1978 | Howes |
| 4,128,100 A | 12/1978 | Wendorff |
| 4,675,004 A | 6/1987 | Hadford et al. |
| 4,719,924 A | 1/1988 | Crittenden et al. |

(Continued)

FOREIGN PATENT DOCUMENTS

DE    10161543 A1    6/2003

(Continued)

OTHER PUBLICATIONS

PCT Search Report and Written Opinion for PCT/US2007/011948, mailed Nov. 16, 2007, 16 pages.

(Continued)

*Primary Examiner* — Brian E. Pellegrino
(74) *Attorney, Agent, or Firm* — Blakely, Sokoloff, Taylor & Zafman, LLP

(57) ABSTRACT

A medical device that can be used for treating a defective heart valve. One aspect of the invention pertains to a longitudinally adjustable medical device that comprises a distal portion, a proximal portion, and a cord member. The distal portion comprises a distal anchoring member, a distal telescope, and a distal backbone. The proximal portion comprises a proximal anchoring member, a proximal telescope, and a proximal backbone. The distal backbone and the proximal backbone are configured to provide a structural support to the device while providing flexibility to the device. The cord member is disposed within the device and used to facilitate longitudinal adjustment for the device.

28 Claims, 33 Drawing Sheets

U.S. PATENT DOCUMENTS

| | | |
|---|---|---|
| 4,781,186 A | 11/1988 | Simpson et al. |
| 4,808,156 A | 2/1989 | Dean |
| 4,817,250 A | 4/1989 | Kurosaki |
| 4,830,023 A | 5/1989 | de Toledo et al. |
| 4,920,980 A | 5/1990 | Jackowski |
| 4,927,421 A | 5/1990 | Goble et al. |
| 4,932,962 A | 6/1990 | Yoon et al. |
| 4,994,067 A | 2/1991 | Summers |
| 5,040,548 A | 8/1991 | Yock |
| 5,061,273 A | 10/1991 | Yock |
| 5,100,418 A | 3/1992 | Yoon et al. |
| 5,100,421 A | 3/1992 | Christoudias |
| 5,102,421 A | 4/1992 | Anspach, Jr. |
| 5,116,337 A | 5/1992 | Johnson |
| 5,129,902 A | 7/1992 | Goble et al. |
| 5,141,520 A | 8/1992 | Goble et al. |
| 5,156,616 A | 10/1992 | Meadows et al. |
| 5,163,903 A | 11/1992 | Crittenden et al. |
| 5,171,233 A | 12/1992 | Amplatz et al. |
| 5,201,598 A | 4/1993 | Tehan |
| 5,234,443 A | 8/1993 | Phan et al. |
| 5,242,456 A | 9/1993 | Nash et al. |
| 5,246,441 A | 9/1993 | Ross et al. |
| 5,261,889 A | 11/1993 | Laine et al. |
| 5,273,533 A | 12/1993 | Bonaldo |
| 5,290,244 A | 3/1994 | Moonka |
| 5,350,395 A | 9/1994 | Yock |
| 5,352,215 A | 10/1994 | Thome et al. |
| 5,358,479 A | 10/1994 | Wilson |
| 5,370,662 A | 12/1994 | Stone et al. |
| 5,374,275 A | 12/1994 | Bradley et al. |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,456,667 A | 10/1995 | Ham et al. |
| 5,487,757 A | 1/1996 | Truckai et al. |
| 5,495,974 A | 3/1996 | Deschenes et al. |
| 5,518,162 A | 5/1996 | Deschenes et al. |
| 5,520,700 A | 5/1996 | Beyar et al. |
| 5,522,873 A | 6/1996 | Jackman et al. |
| 5,531,686 A | 7/1996 | Lundquist et al. |
| 5,549,582 A | 8/1996 | Larsson et al. |
| 5,554,184 A | 9/1996 | Machiraju |
| 5,569,277 A | 10/1996 | Evans et al. |
| 5,571,215 A | 11/1996 | Sterman et al. |
| 5,588,188 A | 12/1996 | Jermyn, Jr. |
| 5,609,598 A | 3/1997 | Laufer et al. |
| 5,613,937 A | 3/1997 | Garrison et al. |
| 5,613,954 A | 3/1997 | Nelson et al. |
| 5,617,854 A | 4/1997 | Munsif |
| 5,626,613 A | 5/1997 | Schmieding |
| 5,632,754 A | 5/1997 | Farley et al. |
| 5,640,955 A | 6/1997 | Ockuly et al. |
| 5,642,736 A | 7/1997 | Avitall |
| 5,643,319 A | 7/1997 | Green et al. |
| 5,681,280 A | 10/1997 | Rusk et al. |
| 5,681,346 A | 10/1997 | Orth et al. |
| 5,682,906 A | 11/1997 | Sterman et al. |
| 5,687,723 A | 11/1997 | Avitall |
| 5,709,224 A | 1/1998 | Behl et al. |
| 5,728,129 A | 3/1998 | Summers |
| 5,782,828 A | 7/1998 | Chen et al. |
| 5,810,869 A | 9/1998 | Kaplan et al. |
| 5,810,882 A | 9/1998 | Bolduc et al. |
| 5,823,955 A | 10/1998 | Kuck et al. |
| 5,824,008 A | 10/1998 | Bolduc et al. |
| 5,865,800 A | 2/1999 | Mirarchi et al. |
| 5,868,733 A | 2/1999 | Ockuly et al. |
| 5,868,767 A | 2/1999 | Farley et al. |
| 5,916,213 A | 6/1999 | Haissaguerre et al. |
| 5,954,731 A | 9/1999 | Yoon |
| 5,961,440 A | 10/1999 | Schweich, Jr. et al. |
| 5,964,772 A | 10/1999 | Bolduc et al. |
| 5,972,022 A | 10/1999 | Huxel |
| 5,989,284 A | 11/1999 | Laufer |
| 6,001,095 A | 12/1999 | de la Rama et al. |
| 6,001,104 A | 12/1999 | Benderev et al. |
| 6,001,127 A | 12/1999 | Schoon et al. |
| 6,004,332 A | 12/1999 | Yoon et al. |
| 6,017,358 A | 1/2000 | Yoon et al. |
| 6,021,340 A | 2/2000 | Randolph et al. |
| 6,027,514 A | 2/2000 | Stine |
| 6,036,715 A | 3/2000 | Yock |
| 6,045,497 A | 4/2000 | Schweich, Jr. et al. |
| 6,050,936 A | 4/2000 | Schweich, Jr. et al. |
| 6,051,008 A | 4/2000 | Saadat et al. |
| 6,059,715 A | 5/2000 | Schweich, Jr. et al. |
| 6,066,100 A | 5/2000 | Willard et al. |
| 6,077,214 A | 6/2000 | Mortier et al. |
| 6,090,096 A | 7/2000 | St. Goar et al. |
| 6,093,199 A | 7/2000 | Brown et al. |
| 6,110,100 A | 8/2000 | Talpade |
| 6,113,609 A | 9/2000 | Adams |
| 6,117,176 A | 9/2000 | Chen |
| 6,120,520 A | 9/2000 | Saadat et al. |
| 6,123,699 A | 9/2000 | Webster, Jr. |
| 6,149,669 A | 11/2000 | Li |
| 6,152,943 A | 11/2000 | Sawhney |
| 6,161,543 A | 12/2000 | Cox et al. |
| 6,162,168 A | 12/2000 | Schweich, Jr. et al. |
| 6,164,283 A | 12/2000 | Lesh |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,174,323 B1 | 1/2001 | Biggs et al. |
| 6,176,240 B1 | 1/2001 | Nikolchev et al. |
| 6,178,346 B1 | 1/2001 | Amundson et al. |
| 6,179,840 B1 | 1/2001 | Bowman |
| 6,182,664 B1 | 2/2001 | Cosgrove |
| 6,183,411 B1 | 2/2001 | Mortier et al. |
| 6,187,040 B1 | 2/2001 | Wright |
| 6,190,401 B1 | 2/2001 | Green et al. |
| 6,190,408 B1 | 2/2001 | Melvin |
| 6,200,302 B1 | 3/2001 | Johnson |
| 6,203,531 B1 | 3/2001 | Ockuly et al. |
| 6,210,378 B1 | 4/2001 | Ouchi |
| 6,210,407 B1 | 4/2001 | Webster, Jr. |
| 6,210,432 B1 | 4/2001 | Solem et al. |
| 6,231,561 B1 | 5/2001 | Frazier et al. |
| 6,231,587 B1 | 5/2001 | Makower |
| 6,241,728 B1 | 6/2001 | Gaiser et al. |
| 6,254,568 B1 | 7/2001 | Ponzi |
| 6,254,598 B1 | 7/2001 | Edwards et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,267,781 B1 | 7/2001 | Tu |
| 6,269,819 B1 | 8/2001 | Oz et al. |
| 6,270,526 B1 | 8/2001 | Cox |
| 6,283,127 B1 | 9/2001 | Sterman et al. |
| 6,283,962 B1 | 9/2001 | Tu et al. |
| 6,290,674 B1 | 9/2001 | Roue et al. |
| 6,299,622 B1 | 10/2001 | Snow et al. |
| 6,306,133 B1 | 10/2001 | Tu et al. |
| 6,312,447 B1 | 11/2001 | Grimes |
| 6,325,823 B1 | 12/2001 | Horzewski et al. |
| 6,355,030 B1 | 3/2002 | Aldrich et al. |
| 6,371,978 B1 | 4/2002 | Wilson |
| 6,374,476 B1 | 4/2002 | Ponzi et al. |
| 6,379,373 B1 | 4/2002 | Sawhney et al. |
| 6,402,780 B2 | 6/2002 | Williamson et al. |
| 6,402,781 B1 | 6/2002 | Langberg et al. |
| 6,408,214 B1 | 6/2002 | Williams et al. |
| 6,419,696 B1 | 7/2002 | Ortiz et al. |
| 6,436,110 B2 | 8/2002 | Bowman et al. |
| 6,447,517 B1 | 9/2002 | Bowman |
| 6,461,366 B1 | 10/2002 | Seguin |
| 6,482,224 B1 | 11/2002 | Michler et al. |
| 6,488,689 B1 | 12/2002 | Kaplan et al. |
| 6,493,575 B1 | 12/2002 | Kesten et al. |
| 6,497,707 B1 | 12/2002 | Bowman et al. |
| 6,500,167 B1 | 12/2002 | Webster, Jr. |
| 6,517,553 B2 | 2/2003 | Klein et al. |
| 6,537,198 B1 | 3/2003 | Vidlund et al. |

| | | |
|---|---|---|
| 6,537,314 B2 | 3/2003 | Langberg et al. |
| 6,551,271 B2 | 4/2003 | Nguyen |
| 6,554,794 B1 | 4/2003 | Mueller et al. |
| 6,554,852 B1 | 4/2003 | Oberlander |
| 6,575,998 B2 | 6/2003 | Beyar |
| 6,585,718 B2 | 7/2003 | Hayzelden et al. |
| 6,599,311 B1 | 7/2003 | Biggs et al. |
| 6,605,086 B2 | 8/2003 | Hayzelden et al. |
| 6,610,033 B1 | 8/2003 | Melanson et al. |
| 6,610,058 B2 | 8/2003 | Flores |
| 6,619,291 B1 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | Goar et al. |
| 6,638,286 B1 | 10/2003 | Burbank et al. |
| 6,648,903 B1 | 11/2003 | Pierson, III |
| 6,656,221 B2 | 12/2003 | Taylor et al. |
| 6,676,702 B2 | 1/2004 | Mathis |
| 6,706,011 B1 | 3/2004 | Murphy-Chutorian et al. |
| 6,706,065 B2 | 3/2004 | Langberg et al. |
| 6,709,442 B2 | 3/2004 | Miller et al. |
| 6,709,456 B2 | 3/2004 | Langberg et al. |
| 6,712,804 B2 | 3/2004 | Roue et al. |
| 6,718,985 B2 | 4/2004 | Hlavka et al. |
| 6,719,767 B1 | 4/2004 | Kimblad |
| 6,723,038 B1 | 4/2004 | Schroeder |
| 6,733,500 B2 | 5/2004 | Kelley et al. |
| 6,746,472 B2 | 6/2004 | Frazier et al. |
| 6,755,812 B2 | 6/2004 | Peterson et al. |
| 6,761,734 B2 | 7/2004 | Suhr |
| 6,764,510 B2 | 7/2004 | Vidlund et al. |
| 6,770,066 B1 | 8/2004 | Weaver et al. |
| 6,770,070 B1 | 8/2004 | Balbierz |
| 6,780,167 B2 | 8/2004 | Leone et al. |
| 6,790,231 B2 | 9/2004 | Liddicoat et al. |
| 6,800,090 B2 | 10/2004 | Alferness et al. |
| 6,808,510 B1 | 10/2004 | DiFiore |
| 6,810,882 B2 | 11/2004 | Langberg et al. |
| 6,824,562 B2 | 11/2004 | Mathis et al. |
| 6,852,124 B2 | 2/2005 | Cox et al. |
| 6,890,353 B2 | 5/2005 | Cohn et al. |
| 6,905,476 B2 | 6/2005 | Ponzi |
| 6,908,478 B2 | 6/2005 | Alferness et al. |
| 6,911,035 B1 | 6/2005 | Blomme |
| 6,921,391 B1 | 7/2005 | Barker et al. |
| 6,951,549 B1 | 10/2005 | Beyerlein |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinski et al. |
| 6,997,951 B2 | 2/2006 | Solem et al. |
| 7,073,504 B2 | 7/2006 | Callister et al. |
| 7,087,064 B1 | 8/2006 | Hyde |
| 7,104,999 B2 | 9/2006 | Overaker |
| 7,160,318 B2 | 1/2007 | Greenberg et al. |
| 7,186,264 B2 | 3/2007 | Liddicoat et al. |
| 7,247,149 B2 | 7/2007 | Beyerlein |
| 7,364,567 B2 | 4/2008 | Beyerlein |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0027322 A1 | 10/2001 | Bowman |
| 2001/0044568 A1 | 11/2001 | Langberg et al. |
| 2002/0010483 A1 | 1/2002 | Follmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0049414 A1 | 4/2002 | Nobles et al. |
| 2002/0077647 A1 | 6/2002 | Snow et al. |
| 2002/0087169 A1 | 7/2002 | Brock et al. |
| 2002/0087173 A1 | 7/2002 | Alferness et al. |
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0169502 A1 | 11/2002 | Mathis |
| 2002/0169504 A1 | 11/2002 | Alferness et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183841 A1 | 12/2002 | Cohn et al. |
| 2002/0188170 A1 | 12/2002 | Santamore et al. |
| 2003/0050598 A1 | 3/2003 | Hayzelden |
| 2003/0069593 A1 | 4/2003 | Tremulis et al. |
| 2003/0078465 A1 | 4/2003 | Pai et al. |
| 2003/0083538 A1 | 5/2003 | Adams et al. |
| 2003/0093071 A1 | 5/2003 | Hauck et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130731 A1 | 7/2003 | Vidlund et al. |
| 2003/0144697 A1 | 7/2003 | Mathis |
| 2003/0144732 A1 | 7/2003 | Cosgrove et al. |
| 2003/0167071 A1 | 9/2003 | Martin et al. |
| 2003/0171776 A1 | 9/2003 | Adams et al. |
| 2003/0212453 A1 | 11/2003 | Mathis et al. |
| 2003/0216764 A1 | 11/2003 | Tu et al. |
| 2004/0002692 A1 | 1/2004 | Claude et al. |
| 2004/0010231 A1 | 1/2004 | Leonhardt et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0059314 A1 | 3/2004 | Schon et al. |
| 2004/0059531 A1 | 3/2004 | Eigler et al. |
| 2004/0064098 A1 | 4/2004 | Cuschieri et al. |
| 2004/0098092 A1 | 5/2004 | Butaric et al. |
| 2004/0122418 A1 | 6/2004 | Voorhees |
| 2004/0138683 A1 | 7/2004 | Shelton et al. |
| 2004/0138744 A1 | 7/2004 | Lashinski et al. |
| 2004/0148020 A1 | 7/2004 | Vidlund et al. |
| 2004/0153147 A1 | 8/2004 | Mathis |
| 2004/0167463 A1 | 8/2004 | Zawacki et al. |
| 2004/0204683 A1 | 10/2004 | McGuckin et al. |
| 2005/0045183 A1 | 3/2005 | Callister et al. |
| 2005/0055089 A1 | 3/2005 | Macoviak et al. |
| 2005/0085844 A1 | 4/2005 | Tremulis et al. |
| 2005/0096629 A1 | 5/2005 | Gerber et al. |
| 2005/0187519 A1 | 8/2005 | Harris et al. |
| 2005/0197635 A1 | 9/2005 | Greydanus et al. |
| 2005/0209633 A1 | 9/2005 | Callister et al. |
| 2005/0267571 A1 | 12/2005 | Spence et al. |
| 2005/0267573 A9 | 12/2005 | Macoviak et al. |
| 2006/0041306 A1 | 2/2006 | Vidlund et al. |
| 2006/0095025 A1 | 5/2006 | Levine et al. |
| 2006/0282161 A1 | 12/2006 | Huynh et al. |
| 2007/0078437 A1 | 4/2007 | Borden et al. |
| 2008/0021417 A1 | 1/2008 | Zawacki et al. |

FOREIGN PATENT DOCUMENTS

| | | |
|---|---|---|
| EP | 0377269 A1 | 7/1990 |
| EP | 0570102 | 11/1993 |
| WO | WO 98/29041 A1 | 7/1998 |
| WO | WO 99/00059 | 1/1999 |
| WO | WO 99/13777 | 3/1999 |
| WO | WO 99/30647 A1 | 6/1999 |
| WO | WO 99/44534 A1 | 9/1999 |
| WO | WO 00/03759 | 1/2000 |
| WO | WO 00/06026 A2 | 2/2000 |
| WO | WO 00/06027 A2 | 2/2000 |
| WO | WO 00/06028 A1 | 2/2000 |
| WO | WO 00/16700 A1 | 3/2000 |
| WO | WO 00/60995 | 10/2000 |
| WO | WO 01/00111 A1 | 1/2001 |
| WO | WO 01/00114 A1 | 1/2001 |
| WO | WO 01/54618 A1 | 1/2001 |
| WO | WO 01/26557 A1 | 4/2001 |
| WO | WO 01/28432 A1 | 4/2001 |
| WO | WO 01/28455 A1 | 4/2001 |
| WO | WO 01/49213 A2 | 7/2001 |
| WO | WO 01/49213 A3 | 7/2001 |
| WO | WO 02/62270 A1 | 9/2001 |

| | | | |
|---|---|---|---|
| WO | WO 01/89440 A2 | 11/2001 | |
| WO | WO 02/053206 A2 | 12/2001 | |
| WO | WO 02/00099 A2 | 1/2002 | |
| WO | WO 02/01999 A2 | 1/2002 | |
| WO | WO 02/60352 A1 | 1/2002 | |
| WO | WO 02/62263 A2 | 2/2002 | |
| WO | WO 02/62408 A2 | 2/2002 | |
| WO | WO 02/63533 A1 | 2/2002 | |
| WO | WO 02/078576 | 3/2002 | |
| WO | WO 02/34167 A2 | 5/2002 | |
| WO | WO 02/39925 A2 | 5/2002 | |
| WO | WO 03/049619 A2 | 6/2003 | |
| WO | WO 03/073913 A2 | 9/2003 | |
| WO | WO 2004/012789 A2 | 2/2004 | |
| WO | WO 2004/014282 A2 | 2/2004 | |
| WO | WO 2004/045463 A2 | 6/2004 | |

OTHER PUBLICATIONS

PCT Invitation to Pay Additional Fees for PCT International Appln. No. US2004/031403, mailed Feb. 15, 2005 (5 pages).

Messas, et al., "Chordal Cutting a New Therapeutic approach for Ischmic Mitral Regurgitation", 2001, *American heart Association Inc.*, pp. 1958-1963.

Bonow, Robert O., et al., "Guidelines for the Management of Patients with Valvular Health Disease", *Report of American College of Cardiology/American Heart Assoc. Task Force on Practice Guidelines*, (Committee on Management of Patients with Valvular Heart Disease), American College of Cardiology and American Heart Assoc., Inc., (1998), pp. 1949-1984.

PCT Invitation to Pay Additional Fees for PCT International Appln. No. PCT/US03/36633, mailed May 19, 2004 (5 pages).

PCT International Preliminary Report on Patentability and Written Opinion for PCT Appln No. US2004/031403, mailed Apr. 13, 2006 (8 pages).

PCT International Search Report and Written Opinion of the International Searching Authority for PCT Appln No. US2004/031403, mailed May 18, 2005 (14 pages).

Abbott Cardiovascular Systems, Final Office Action dated Apr. 15, 2009 for U.S. Appl. No. 10/676,616.

Abbott Cardiovascular Systems, Non final office action dated Jun. 12, 2009 for U.S. Appl. No. 11/240,569.

Abbott, Non Final Office Action dated Aug. 24, 2005; U.S. Appl. No. 10/739,554.

Abbott, Non Final Office Action dated Mar. 22, 2005; U.S. Appl. No. 10/739,554.

Abbott, Non Final Office Action dated 10/20/045; U.S. Appl. No. 10/739,554.

Abbott, Final Office Action dated Feb. 24, 2-06; U.S. Appl. No. 10/739,554.

Abbott, Non Final Office Action dated 02/30/10; U.S. Appl. No. 10/464,132.

Abbott, Non Final Office Action dated Dec. 2, 2008; U.S. Appl. No. 10/464,132.

Abbott, Non Final Office Action dated May 13, 2008; U.S. Appl. No. 10/464,132.

Abbott, Non Final Office Action dated Mar. 27, 2007; U.S. Appl. No. 10/464,132.

Abbott, Non Final Office Action dated Feb. 24, 2006; U.S. Appl. No. 10/464,132.

Abbott, Final Office Action dated Aug. 3, 2009; U.S. Appl. No. 10/464,132.

Abbott, Final Office Action dated Sep. 14, 2007; U.S. Appl. No. 10/464,132.

Abbott, Final Office Action dated Nov. 2, 2006; U.S. Appl. No. 10/464,132.

Abbott, Non Final Office Action dated Jan. 27, 2008; U.S. Appl. No. 10/295,714.

Abbott, Non Final Office Action dated Apr. 5, 2007; U.S. Appl. No. 10/295,714.

Abbott, Non Final Office Action dated Mar. 7, 2007; U.S. Appl. No. 10/295,714.

Abbott, Non Final Office Action dated May 12, 2006; U.S. Appl. No. 10/295,714.

Abbott, Final Office Action dated Jun. 30 2008; U.S. Appl. No. 10/295,714.

Abbott, Final Office Action dated Aug. 14, 2007; U.S. Appl. No. 10/295,714.

Abbott, Non Final Office Action dated Jan. 5, 2007; U.S. Appl. No. 10/298,133.

Abbott, Non Final Office Action dated Dec. 20, 2005; U.S. Appl. No. 10/298,133.

Abbott, Final Office Action dated May 1, 2007; U..S Appl. No. 10/298,133.

Abbott, Final Office Action dated Jun. 15, 2006; U.S. Appl. No. 10/298,133.

Abbott, Non Final Office Action dated Jan. 2, 2009; U.S. Appl. No. 11/008,902.

Abbott, Final Office Action dated Aug. 3, 2009; U.S. Appl. No. 11/008,902..

Abbott, Non Final Office Action dated Apr. 30, 2007; U.S. Appl. No. 10/712,553.

Abbott, Non Final Office Action dated Mar. 3, 3006; U.S. Appl. No. 10/712,553.

Abbott, Final Office Action dated Nov. 22, 2006; U.S. Appl. No. 10/712,553.

Abbott Cardiovascular Systems, First notice of reasons for refusal dated Apr. 26, 2011 for JP Appln. No. 2008-507728.

Advanced Cardiovascular Systems, International search report and written opinion dated Aug. 11, 2006 for PCT/US2006/013909.

Abbott Cardiovascular Systems, Non final office action dated Aug. 19, 2008 for U.S. Appl. No. 10/740,360, (Aug. 19, 2008), 8 pages.

Abbott Cardiovascular Systems, Final Office Action dated Mar. 24, 2009 for U.S. Appl. No. 10/740,360.

Abbott Cardiovascular Systems, Final office action dated Apr. 13, 2010 for U.S. Appl. No. 11/112,546.

Abbott Cardiovascular Systems, Final office action dated Aug. 3, 2010 for U.S. Appl. No. 10/464,132.

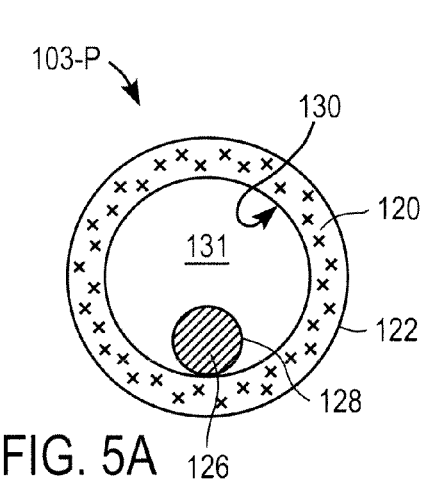
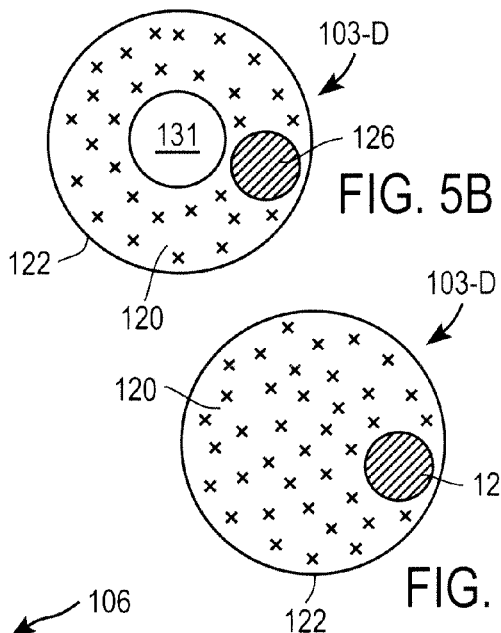
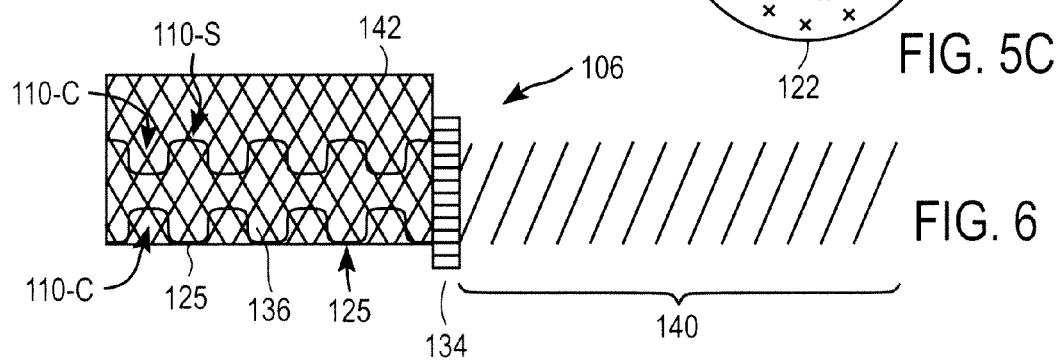
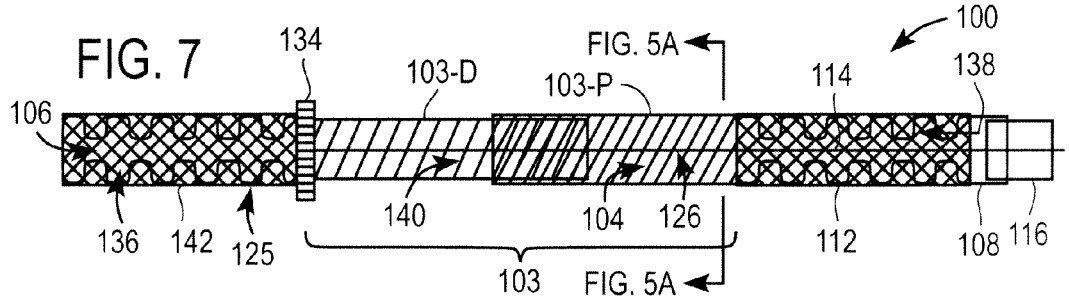
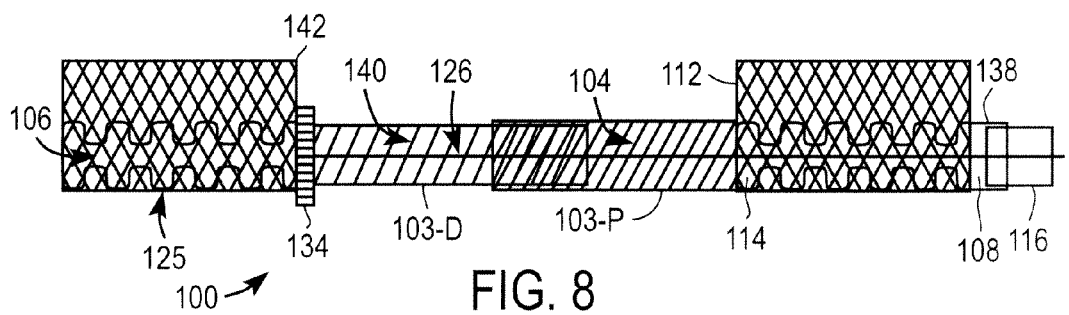

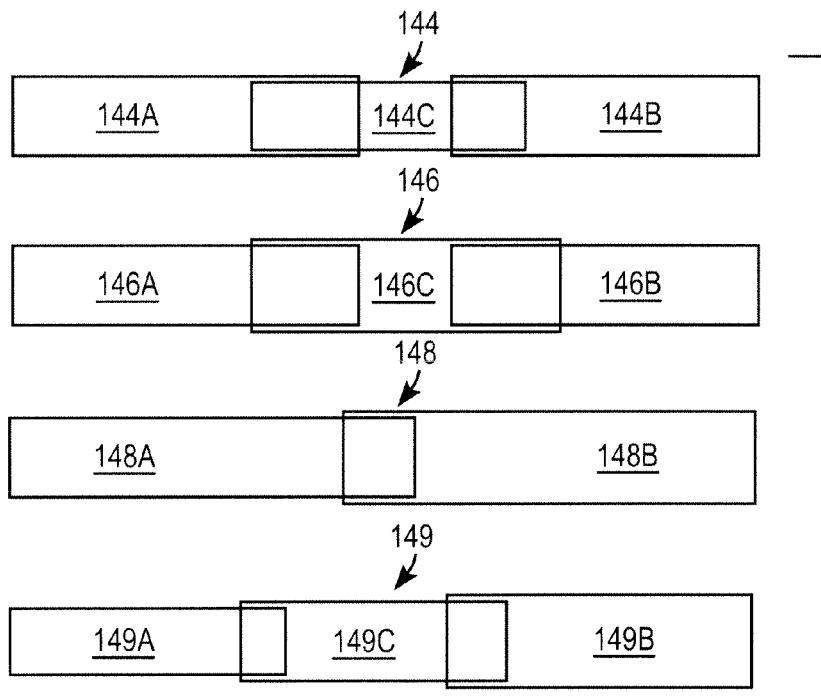
FIG. 10
FIG. 11A
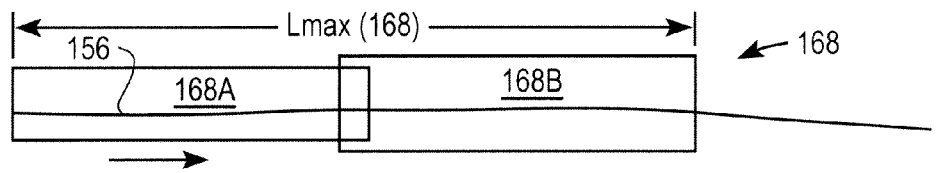
FIG. 11B
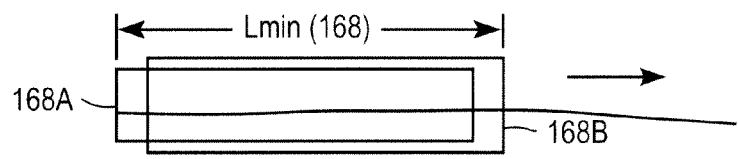
FIG. 11C
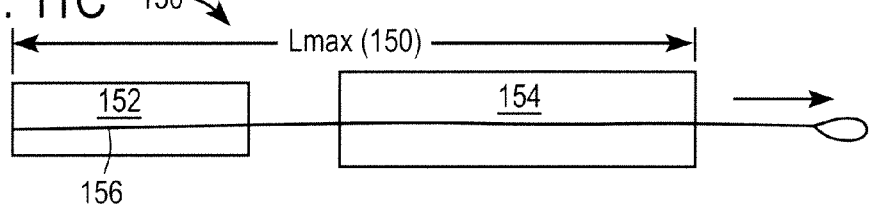
FIG. 11D
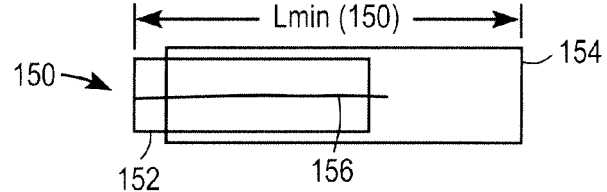

FIG. 12A
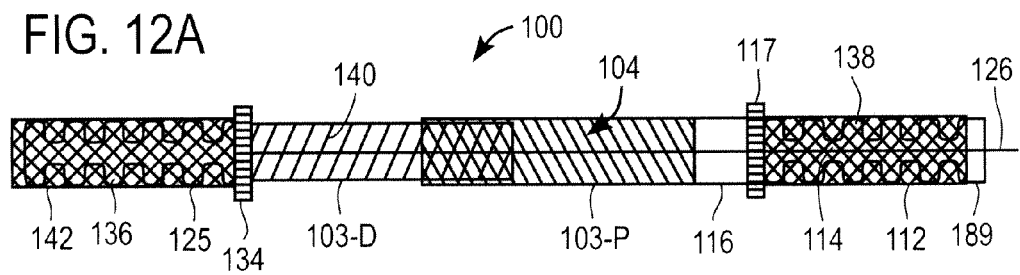
FIG. 12B
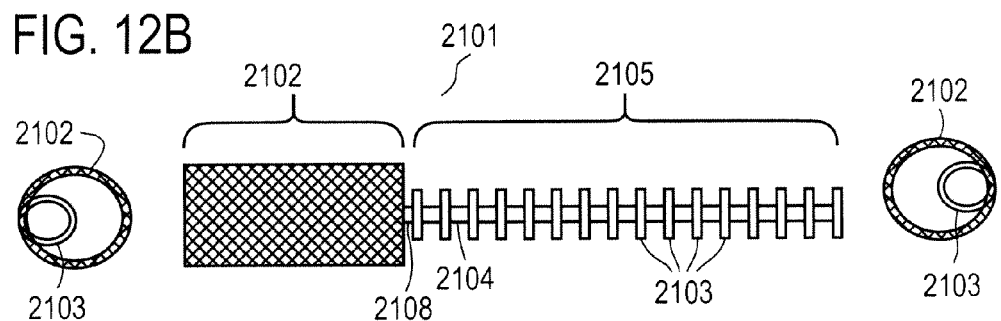
FIG. 12C
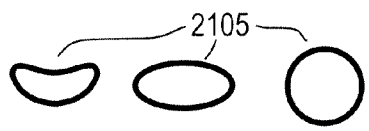
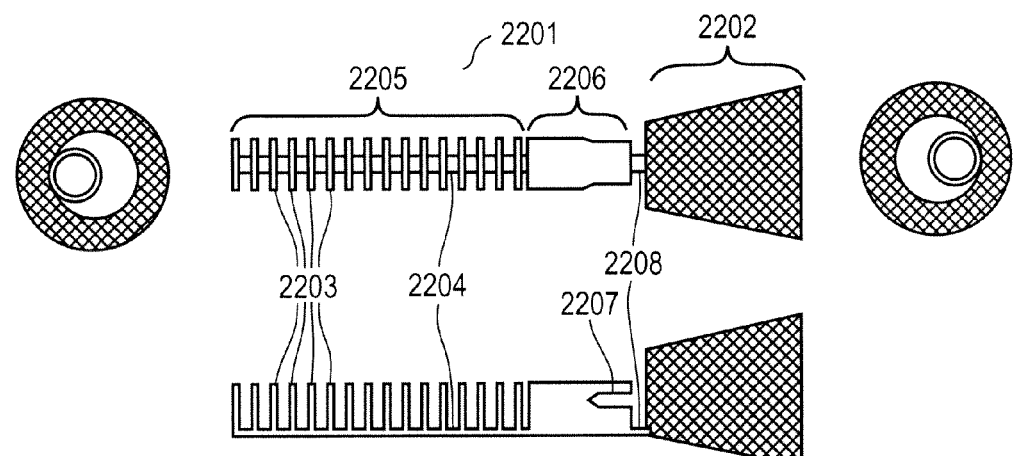
FIG. 12D

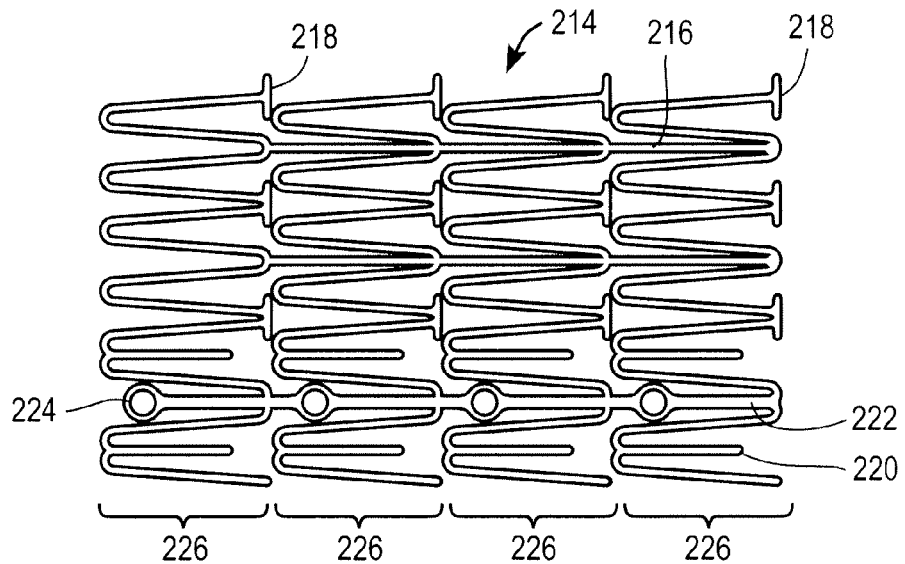
FIG. 19
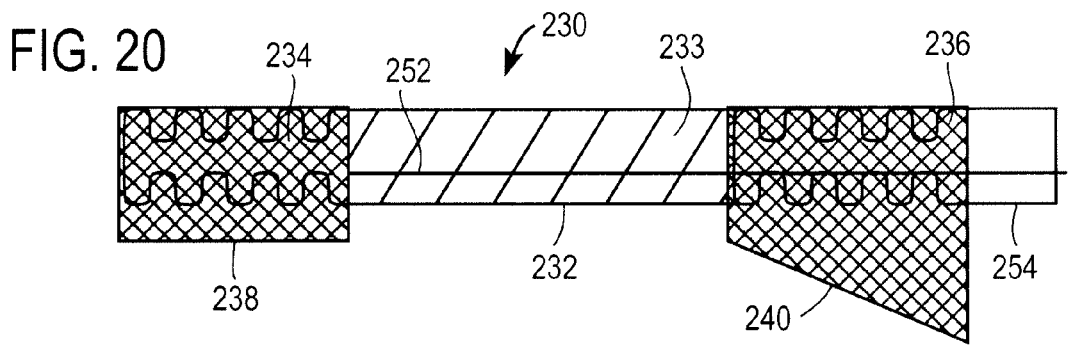
FIG. 20
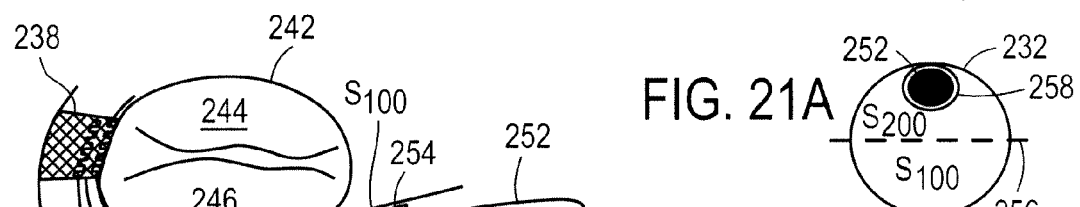
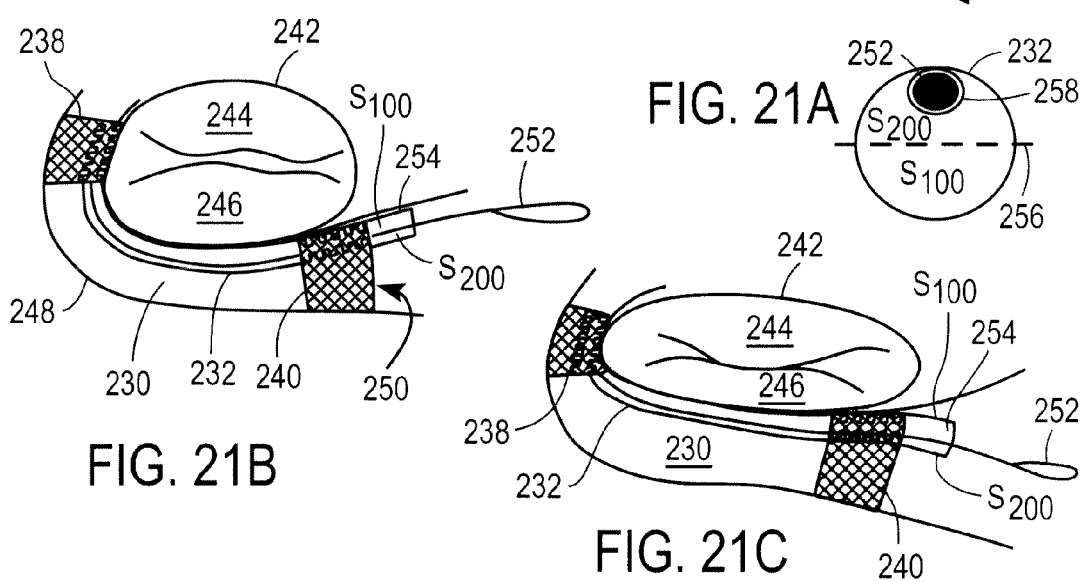
FIG. 21B
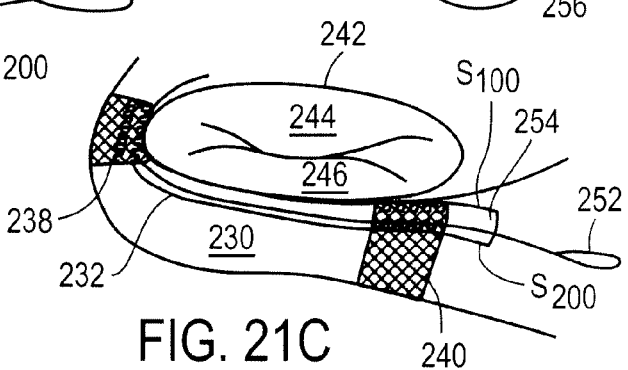
FIG. 21A
FIG. 21C

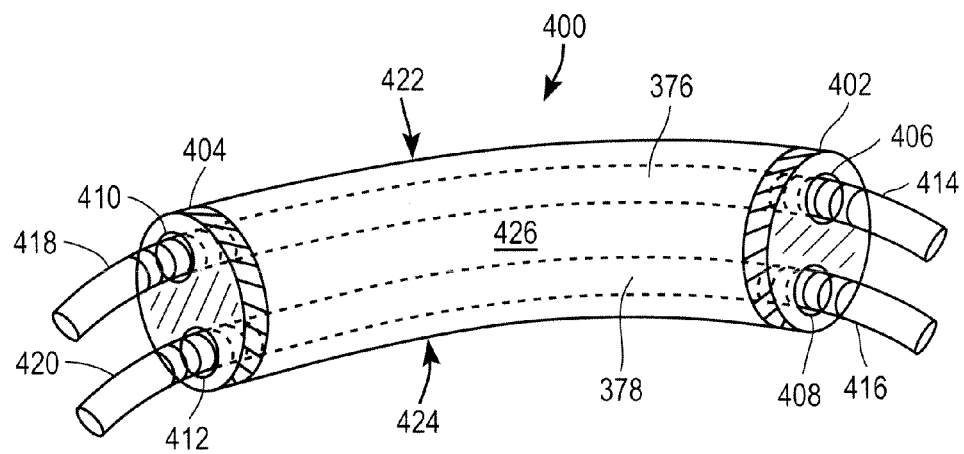
FIG. 31B-1
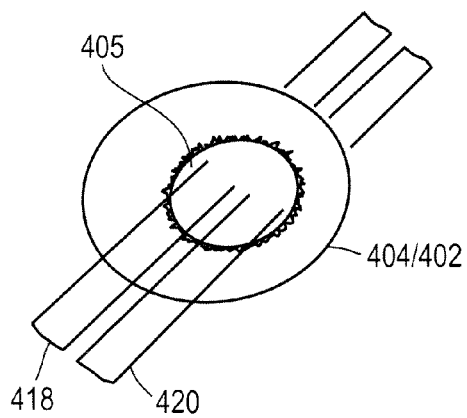 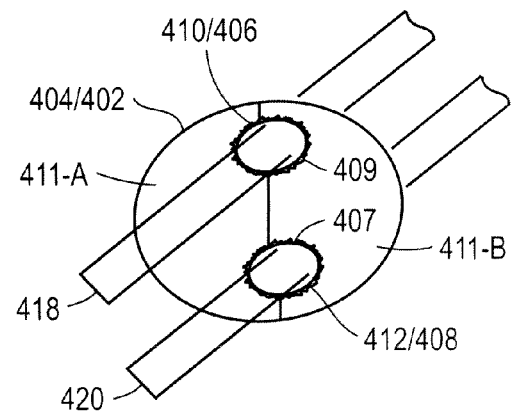
FIG. 31B-2  FIG. 31B-3

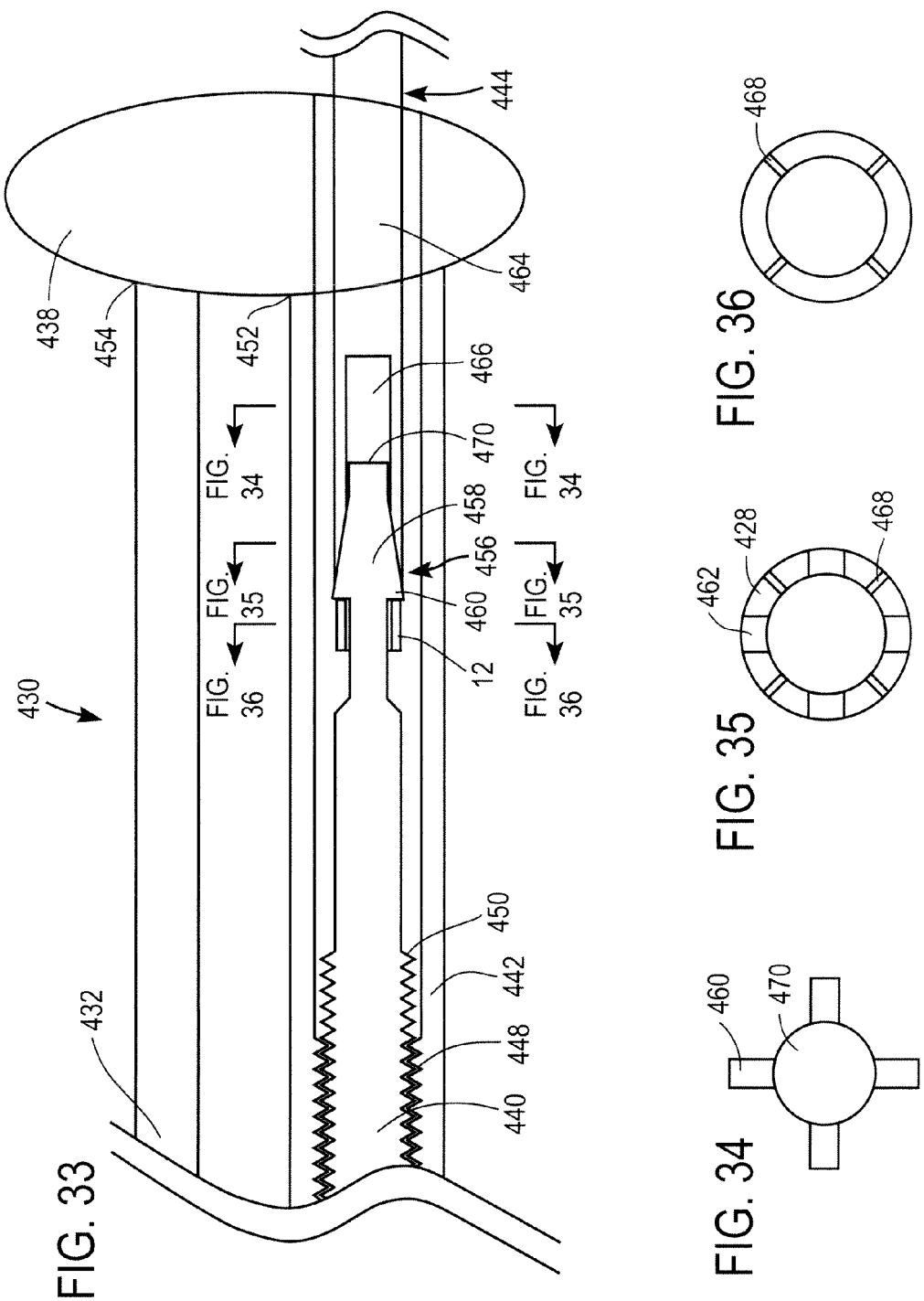

TELESCOPING APPARATUS FOR DELIVERING AND ADJUSTING A MEDICAL DEVICE IN A VESSEL

REFERENCE TO RELATED APPLICATION

This is a continuation-in-part of each of the following Patent Applications: Ser. No. 10/295,714 filed on Nov. 15, 2002 now U.S. Pat. No. 7,485,143; Ser. No. 10/464,132 filed on Jun. 17, 2003 now abandoned, which is a continuation in part of Ser. Nos. 10/295,714; 10/740,360 filed on Dec. 17, 2003 now U.S. Pat. No. 7,828,819, which is a continuation in part of Ser. Nos. 10/295,714; 11/008,902 filed on Dec. 10, 2004 now U.S. Pat. No. 7,981,152; and Ser. No. 11/112,546 filed on Apr. 22, 2005, all of which are hereby incorporated by reference in their entireties.

FIELD

Embodiments of the present invention pertain to apparatuses (medical devices) that can be deployed in a location in a patient, such as a vessel, vessels, onto a target tissue, and the like, for a particular therapeutic or diagnostic treatment. Embodiments of the present invention also pertain to methods to deployed apparatus (medical devices) in such locations for a particular therapeutic or diagnostic treatment.

BACKGROUND

Many devices have been developed that can be used to treat various heart conditions or other conditions. FIG. 55 illustrates a heart 10. There are four valves in the heart 10 that serve to direct the flow of blood through the two sides of the heart 10 in a forward direction. The four valves are a mitral valve 20, an aortic valve 18, a tricuspid valve 60, and a pulmonary valve 62 as illustrated in FIG. 55. The mitral valve 20 is located between the left atrium 12 and the left ventricle 14. The aortic valve 18 is located between the left ventricle 14 and the aorta 16. These two valves direct oxygenated blood coming from the lungs, through the left side of the heart, and into the aorta 16 for distribution to the body. The tricuspid valve 60 is located between the right atrium 22 and the right ventricle 24. The pulmonary valve 62 is located between the right ventricle 24 and the pulmonary artery 26. These two valves direct de-oxygenated blood coming from the body, through the right side of the heart, into the pulmonary artery 26 for distribution to the lungs, where it again becomes re-oxygenated and distributed to the mitral valve 20 and the aortic valve 18.

All of the heart valves are complex structures. Each valve consists of moveable "leaflets" that are designed to open and close. The mitral valve has two leaflets and the tricuspid valve has three. The aortic and pulmonary valves have leaflets that are more aptly termed "cusps" and are shaped somewhat like a half-moon. The aortic and pulmonary valves each have three cusps.

Blood flows into the left ventricle 14 through the mitral valve 20 that opens during diastole. Once the left ventricular cavity has filled, the left ventricle 14 contracts during systole. The mitral valve 20 closes (the leaflets of the mitral valve 20 re-approximate) while the aortic valve 18 opens during systole allowing the oxygenated blood to be ejected from the left ventricle 14 into the aorta 16. A normal mitral valve allows blood to flow into the left ventricle and does not allow leaking or regurgitating back into the left atrium and then into the lungs during systole. The aortic valve allows blood to flow into the aorta and does not allow leaking (or regurgitating) back into the left ventricle. The tricuspid valve 60 functions similarly to the mitral valve to allow deoxygenated blood to flow into the right ventricle 24. The pulmonary valve 62 functions in the same manner as the aortic valve 18 in response to relaxation and contraction of the right ventricle 24 in moving de-oxygenated blood into the pulmonary artery and thence to the lungs for re-oxygenation.

With relaxation and expansion of the ventricles (diastole), the mitral and tricuspid valves open, while the aortic and pulmonary valves close. When the ventricles contract (systole), the mitral and tricuspid valves close and the aortic and pulmonary valves open. In this manner, blood is propelled through both sides of the heart.

The anatomy of the heart and the structure and terminology of heart valves are described and illustrated in detail in numerous reference works on anatomy and cardiac surgery, including standard texts such as Surgery of the Chest (Sabiston and Spencer, eds., Saunders Publ., Philadelphia) and Cardiac Surgery by Kirklin and Barrett-Boyes.

In chronic heart failure (CHF), the size of the heart becomes enlarged. This enlargement can cause the annular size of the valves that separate the atria from the ventricles to also become enlarged. The mitral valve is generally the most affected and has the most serious effects on patient health. FIG. 55 illustrates a sectional view of the positions of the cardiac valves such as the mitral valve 20 present in the heart 10. The annular enlargements can become so pronounced that the leaflets of the valve(s) are unable to effectively close. The annular enlargement most profoundly affects the posterior leaflet 25 of the mitral valve 20. FIGS. 56-57 illustrate a sectional view of the expansion of the annulus 28 of the mitral valve 20. As shown, the annulus 28 expands from a cross-sectional size indicated by the number 21 to the expanded cross-sectional size indicated by the number 23. The expansion/enlargement typically affects the posterior leaflet 25 of the mitral valve 20. During systole, due to the annular enlargement, the valve leaflets do not meet (valve not fully closed, no coaptation), thus some amount of blood flows the wrong way back through the valve from the ventricle and back into the atrium (valve regurgitation) where it raises the pressure in the atrium. This is termed "Mitral Valve Regurgitation" or MVR. MVR reduces the amount of blood pumped by the heart to the body. This reduction in blood flow can be life threatening, especially in patients that have lost ventricular tissue (i.e. heart attack victims), have contraction synchronization problems and/or other problems that reduce the heart's ability to act as a pump.

Regurgitation is common, and is occurring in about 7% of the population. Mitral Valve Regurgitation is caused by a number of conditions, including genetic defects, infections, coronary artery disease (CAD), myocardial infarction (MD or congestive heart failure (CHF). Most cases are mild and if the symptoms are bothersome, they can usually be controlled with drugs.

In more serious cases, the faulty or defective valve can be repaired with a surgical procedure such as an annuloplasty. As illustrated in FIG. 58 illustrates an annuloplasty 30 used in a surgical procedure in which a synthetic ring 32 is placed around the valve rim (annulus) 34. Sutures 38 are put into the valve annulus 34 and the synthetic ring 32. This causes proper closing by shrinking the size of the valve opening 36. The synthetic ring 32 also reduces and reshapes the annulus 34 to move the posterior leaflet toward the anterior leaflet. FIG. 59 illustrates another surgical procedure in which a heart valve, such as the mitral valve 20, is repaired by reconstruction. First, at step A, a section P2 from the posterior leaflet 40 of the mitral valve 20 is excised. Then, sequentially at steps B, C, D, and E, sections P1 and P3 of the posterior leaflet 40 are sutured together. The reconstruction shrinks the size of the valve opening 36. In some instances, a faulty or defective valve must be surgically replaced with a new valve. Examples of new valves include homograft valves (valves harvested from human cadavers), artificial mitral valves, and mechanical valves. Similar procedures are currently used to repair a mitral valve.

All of the procedures above are typically major surgical procedures that require the opening of the chest by sternotomy or at best through small incisions in the chest wall, performing a heart lung bypass and stopping the heartbeat. While surgical procedures such as those mentioned can successfully reconstruct the valve back to a non-regurgitant state, this problem is often associated with Chronic Heart Failure (CHF) and/or other debilitating diseases and thus, the sufferers of the regurgitant valve are often unable to tolerate the required open heart surgery. In CHF patients, the heart is progressively less able to pump sufficient blood to meet the body's needs, usually due to the continuing enlargement of the left ventricle (and adjacent structures) in response to high blood pressure, high heart rate, ECG conduction/timing problems and/or insults to the ventricular tissue, such as Myocardial Infarct (MI). As the body's cardiac compensatory mechanisms act to maintain blood flow (cardiac output), the increased stress and metabolic impacts cause further cardiac enlargement and other detrimental changes. The onset of mitral valve regurgitation further reduces cardiac output and, thus accelerates the CHF process. Therefore, there is a need for a less invasive and traumatic way to treat mitral valve regurgitation (MVR).

SUMMARY

The exemplary embodiments of the present invention disclose apparatuses and methods for treating a valve such as a defective heart valve. Treating a defective heart valve is only one exemplary use of the exemplary embodiments of the present invention. Exemplary embodiments of the present invention can be used to treat other conditions without exceeding the scope of the invention.

Devices and methods of the present invention pertain to medical devices that employ a distal and proximal anchoring members coupled to a cinching device to repair a defective valve such as a defective mitral valve. An exemplary basic mitral device includes a distal anchoring member and a proximal anchoring member connected by a telescoping assembly controlled by a cord disposed therein and a cord locking mechanism included at a proximal end of the device. The distal anchoring member is deployed at a position within a vessel such as a coronary sinus or great cardiac vein. The proximal anchoring member is deployed at a position proximal to the distal anchoring member such as the coronary sinus ostium or entrance. The telescoping assembly is located between the distal and proximal anchoring members. The telescoping assembly contains two or more tubes or members that can slide into and/or over each other so as to shorten, lengthen, or adjust the distance between the two anchoring members. The cord is affixed to a distal point of the telescoping assembly or to the distal anchoring member and controls the sliding of the telescoping members. The cord may run the entire length of the telescoping assembly. The cord locking mechanism is mounted on a proximal portion of the telescoping assembly or on the proximal anchoring member and is provided to lock the telescoping assembly and/or the distance between the distal and proximal anchoring members at a desired maximum length.

Typically, the distal anchoring member is deployed first before the proximal anchoring member. The distal anchoring member fixes the distal end of the device in place relative to the vessel. Typically, the device is initially delivered into the vessel with its telescoping portions at or near their least amount of engagement with each other and, thus the device is at or near its longest length. When the telescoping portions are at their least engagement, the device is at its most flexible and therefore, is able to be the most easily positioned into the distal anatomy. Thus, it is anticipated that, in most cases, the device will require shortening to position the proximal anchoring member at its desired location for deployment. The cord is pulled relative to the proximal portion of the device such that the telescoping members slide into or over each other to a desired length, such that the proximal anchoring member is positioned at the desired location. This action reduces the distance between the distal and proximal anchoring members and reduces the length of the telescoping section. It is to be understood that in other instances, the device may begin in its shorter length and be lengthened during the placement process for the proximal anchoring member.

When the proximal anchoring member is deployed, the device is fixed in place relative to the vessel. The cord is pulled relative to the proximal portion of the device such that the telescoping portions slide into or over each other to a desired length, such that the desired shortening/cinching and/or re-shaping of the vessel and adjacent structures are obtained. Then, the cord locking mechanism is used to lock the cord and thus, the device is locked such that this new shortened length is the maximum length that the device can attain. In one example, as used in the coronary sinus, the cinching causes the device in the coronary sinus to push at least a portion of a leaflet of the mitral valve adjacent the coronary sinus, i.e. the posterior leaflet, closer to the other leaflet, i.e. the anterior leaflet, to repair regurgitation of the mitral valve. FIG. 60 illustrates an example of a device 11 having a proximal anchoring member 13 and a distal anchoring member 19 deployed in a coronary sinus 15. The proximal anchoring member 13 is deployed at the entrance of the coronary sinus 17 and the distal anchoring member 19 is deployed more distally into the coronary sinus or great cardiac vein 15. The device 11, once deployed, can reshape the mitral valve 20 and thus, can repair mitral valve regurgitation. Such a device can be delivered at or used for other location(s), vessel(s), or tissue(s).

A delivery system similar to that described in U.S. patent application Ser. No. 11/008,902 can be used to deliver a device such as the one described above into the coronary sinus or other vessel(s). A proximal handle is also provided herein that can be used to control the deployments of each of the anchoring members and control the cord of the particular device. In one embodiment, the proximal handle includes a body, an anchor control system, a constraint system, an actuator control system, and a cord tension and/or translation control system. The body is configured to constrain the longitudinal motion of an inner member of the delivery system and house the other components of the handle. The inner member is slidably accommodated within the delivery catheter and constrains the proximal motion of the proximal portion of the particular device within the delivery catheter. The anchor control is configured to control the longitudinal position of the delivery catheter relative to the inner member and is slideably contained by the body. The delivery catheter constrains the anchor or anchors (a part of the particular device) in their undeployed/unexpanded state. The anchor control engages the device catheter such that moving the anchor control causes the delivery catheter to move accordingly, such that the anchors may be unconstrained or deployed. A portion of the constraint system is configured to control a longitudinal movement of the anchor control. A set of lock member(s) removable from (or moveable on) the handle is contained by the body to provide such constraint system, wherein removing (or moving) one lock member enables the anchor control to move longitudinally. The cord tension and/or translation control is slidably contained by the body and is configured to place tension and/or a translation on a cord (a part of the particular device) to control the cinching and/or deformation of the particular device to be controlled by and releasably connected to the proximal handle. The cord tension and/or translation control system may also constrain the distal motion of the particular device within the delivery catheter. A portion of the constraint system is configured to control a longitudinal movement and/or tension applied to the cord of a particular device by the cord tension and/or translation control. A set of lock member(s) removable from (or moveable on) the handle is contained by the body to provide such constraint system, wherein removing (or moving) one lock member enables the cord tension and/or translation control to move longitudinally. The actuator control system provides an access path from outside the body, through the inner member attached to the body, and accommodates an actuator member for a locking device (a part of the particular device). A pusher engages the actuator member at the proximal end of the actuator access path to effectuate movement of the actuator member in a controlled manner.

Embodiments of the present invention build upon the basic components of the devices described.

One exemplary embodiment pertains to a longitudinally adjustable apparatus that comprises a distal portion, a proximal portion and a cord member. The distal portion comprises a distal anchoring member, a distal telescope, a telescope stop and a distal backbone. The proximal portion comprises a proximal anchoring member, a proximal telescope, a cord-locking member, and a proximal backbone. The distal anchoring member and the proximal anchoring member each is collapsible and expandable. The distal backbone has a proximal section, a distal section, and a middle section. The distal anchoring member couples to the distal section, and the telescope stop couples to or comprises the middle section. It is preferred that the distal end of the cord member be coupled to the proximal end of the distal section of the distal backbone. The proximal section of the distal backbone is flexible, may be covered with a polymer(s) or a weave(s) and forms the distal telescope. The telescope stop is configured to limit the amount of engagement of the two telescope portions. The proximal backbone has a proximal section, a distal section and a middle section. The proximal anchoring member may couple to either the middle or the proximal section and the cord locking member couples to the other section. The distal section of the proximal backbone is flexible, may be covered with a polymer(s) or a weave(s) and forms the proximal telescope. The cord member is disposed within the proximal and distal portions. The cord member is coupled to at least a portion of the distal portion and is slidable within the proximal portion of the device. The cord-locking member is configured to lock the proximal portion of the device to a desired position along the cord member. The backbones provide structural support to the distal and proximal portions and a protective layer within the distal and proximal portions from deformation and wear by the cord member. The backbones help prevent catastrophic damage to the distal and proximal portions caused by the cord member while still providing flexibility to the apparatus. The proximal and distal telescopes, which contain, at least, a portion of the proximal and distal backbones, distribute the forces resulting, at least, in part from the cinched cord over the vessel wall to prevent damage to the vessel wall.

Some embodiments of the present invention provide a flexibility of deploying a proximal anchoring member prior to deploying the distal anchoring member. One exemplary embodiment pertains to a method that places a delivery sheath within a vessel. An implantable device is moveably disposed within the delivery sheath, and an actuator is releasably coupled to the implantable device. The implantable device further comprises a distal anchoring member, a proximal anchoring member, and a connecting member coupled at a distal end to the distal anchoring member and at second end to the proximal anchoring member. The connecting member is a longitudinally adjustable member in many embodiments. The delivery sheath is retracted while the device is sufficiently actuated from the delivery sheath to deploy the proximal anchoring member. The device is advanced more distally into the vessel to deploy the connecting member along the inner wall of the vessel. An inflatable balloon is placed within the vessel proximate the connecting member and inflated to hold the connecting member in place. The delivery sheath is further retracted and the device actuated sufficiently from the delivery sheath to deploy the distal anchoring member while the connecting member is held in place. The balloon, actuator, and delivery sheath are removed completely when deployments of the proximal anchoring member, connecting member, and distal anchoring member are completed.

The methods of treating mitral valve using the exemplary embodiments of the present invention are also disclosed and other exemplary embodiments are disclosed.

BRIEF DESCRIPTION OF THE DRAWINGS

The present invention is illustrated by way of example and not limitation in the figures of the accompanying drawings, in which like references indicate similar elements and in which:

FIGS. 1-8 illustrate various views or sections of a device having a proximal anchoring member, a distal anchoring member, a telescoping assembly, and a backbone included with the telescoping assembly;

FIG. 10 illustrates exemplary telescoping assemblies;

FIGS. 11A-11D compare a telescoping assembly without using a cord to provide length extension to a telescoping assembly that uses a cord to provide length extension;

FIGS. 12A-12D illustrate other exemplary devices having a proximal anchoring member, a distal anchoring member, a telescoping assembly, and a backbone included with the telescoping assembly;

FIG. 19 illustrates an exemplary embodiment of an anchoring member having an attachment spine and anchors in according to embodiments of the present invention;

FIG. 20 illustrates an exemplary embodiment of a proximal anchoring member that is larger than a distal anchoring member connected by a flexural member;

FIGS. 21A-21C illustrate an exemplary embodiment of a device made in accordance to embodiments of the present invention deployed in a coronary sinus;

FIGS. 25A, 25B1-25B2, 25C1-25C2, 26-27, and 28A-28B illustrate various sections of an exemplary embodiment of a device having a proximal anchoring member, a distal anchoring member, a cinching member, and a backbone included with the cinching member;

FIGS. 30, 31A-1 to 31A-3, 31B-1 to 31B-3, and 32A-32B illustrate an exemplary embodiment of a device having a proximal anchoring member, a distal anchoring member, and a connecting member that can be adjusted by a turned-buckled assembly in according to embodiments of the present invention;

FIGS. 33-37 & 38A-38B illustrate in more details the device employing the turned-buckled assembly shown in FIG. 30;

DETAILED DESCRIPTION

Figure 1:
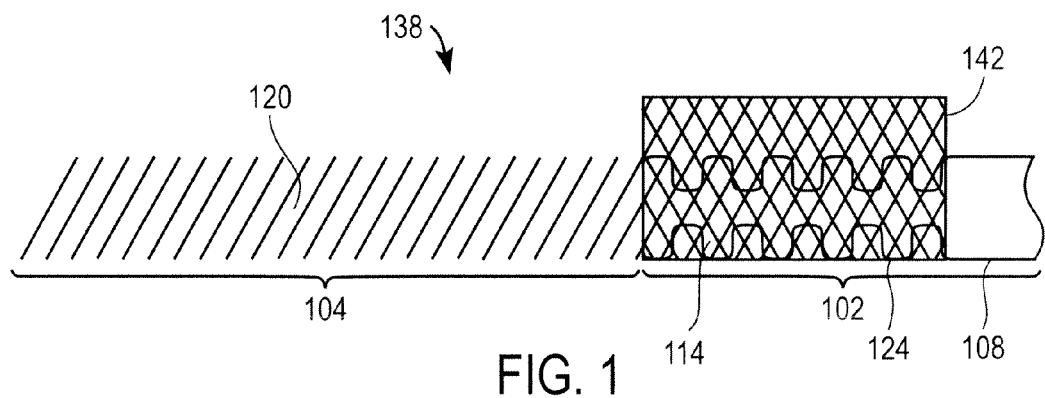

Exemplary embodiments of the present invention pertain to a novel medical device that can be used as an annuloplasty device to treat medical conditions such as defective or faulty heart valves. Exemplary embodiments of the invention also pertain to a method of using a medical device to treat such conditions. Devices of the embodiments of the present invention can also be used for other purposes in addition to being used as annuloplasty devices. The exemplary embodiments can be used to treat other conditions or for other purposes without exceeding the scope of the embodiments. In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

As mentioned, there is a need for a less invasive and traumatic way to treat mitral valve regurgitation (MVR). The exemplary embodiments discussed below provide for a less invasive and less traumatic way to treat not only a faulty mitral valve but also to change or modify the shape of other body structures adjacent to other blood vessels.

Exemplary devices of the present invention can perform many treatments. In one exemplary embodiment, the devices are used for treating a faulty heart valve such as those seen in MVR. A device of the embodiments of the present invention can also reshape a vessel, part of a vessel, an adjacent body structure (or part of the body structure) to the vessel having the device deployed therein, such as a valve or the annulus of a valve. Reshaping includes at least one of reducing, reforming, or adjusting of the vessel, a section of the vessel (e.g., coronary sinus/vein), a vessel or tissue adjacent the vessel(s) with the device deployed therein, and a valve (or the valve annulus) adjacent the vessel(s) with the device deployed therein. Reshaping may also include increasing the curvature (or reducing the radius along at least a portion of the curvature) of the vessel or the adjacent vessel. Reshaping may also include decreasing the curvature (or increasing the radius along at least a portion of the curvature) of the vessel or the adjacent vessel.

In many applications, a device is implanted in a flow path of the heart (e.g., a vessel, a coronary sinus, etc). The heart endures, experiences, and/or causes cyclic motions and in turn causes cyclic motions to the device. The cyclic motions subject the device to repetitive motions. In embodiments where the device includes a cord for particular control and/or adjustment as previously mentioned, the cyclic motions tend to cause damage and early wear-and-tear to the device or components of the device. For instance, a device includes a distal anchoring member and a proximal anchoring member connected by cinching devices (e.g., a telescoping assembly, a cord, and a cord lock). As previously discussed, the distal anchoring member and the proximal anchoring member position and fix the device in place and prevent the device from experiencing longitudinal position changes in the vessel. The cord and cord lock working in conjunction enables the telescoping assembly to be shortened and then to lock the device into a particular maximum length, as desired for the appropriate treatment. However, the force applied on the cord and movement of the cord relative to the telescoping assembly during cardiac motion may cause the cord to apply a frictional force substantially to one side of the telescoping assembly. Since the cord is disposed within the telescoping assembly and the telescoping assembly may further shorten, rotate and flex in response to the cyclic motions of the heart, at least some portions of the telescope assembly may move relative to the cord. This motion may cause a sawing-like and/or rubbing motions of the cord relative to the telescoping assembly. A sawing-like or rubbing motion of the cord may cause deformation and wear to the telescoping assembly or cause similar damage to the cord, causing the cord to break. The cord may also cause similar damage to the other areas that it runs through, such as a portion of the attachment areas of the distal and proximal anchoring members and may cause a failure of the device to perform as desired.

In one embodiment, a protective and supportive backbone is included with a device. As will be apparent from the below descriptions, the protective backbone minimizes and/or protects the device and components of the device from the potential damaging effects caused by the sawing-like or rubbing motion of a cord included in the device. FIGS. 1-8 illustrate various portions of a device 100 having a protective and supportive backbone. FIGS. 7-8 illustrate the device 100, which includes a distal anchoring member 142, a proximal anchoring member 112, a telescoping assembly 103, and a set of proximal and distal backbones (details follow). The telescoping assembly gives the device 100 its longitudinal adjustability capability.

Details of a distal anchoring member, a proximal anchoring member, and a telescoping assembly can be found in U.S. patent application Ser. No. 10/295,714 previously mentioned. FIG. 7 illustrates the anchoring members 112 and 142 in their compressed state and FIG. 8 illustrates the anchoring members 112 and 142 in their expanded state.

In one embodiment, the telescoping assembly includes two or more telescoping tubes or members configured to slide into and out of one another to shorten or lengthen the telescoping assembly. As shown in FIGS. 7-8, the telescoping assembly 103 includes a distal telescoping member 103-D and a proximal telescoping member 103-P, which are configured to slide into and out of one another. It is preferred that the distal telescoping member 103-D has a smaller outer diameter (OD) than the proximal telescoping member 103-P, as the distal telescoping member is positioned further into the vessel/anatomy where device flexibility is desired to aid in placement/negotiating the anatomy and a smaller OD telescope may be more easily made to be flexible than the preferred larger OD proximal telescoping member 103-P.

In one embodiment, the distal telescoping member 103-D includes as a part of its construction a portion of the distal backbone 106. As can be seen in FIGS. 6-8, the distal backbone 106 is comprised of a distal anchor attachment section 136 and a spring-like section 140. The distal backbone 106 may be a single structure (cut from a single tube) that may include an area for the distal anchoring member attachment section 136. The distal backbone 106 also includes an area for the attachment of the distal end of a cord 126 and a spring-like section 140 that supports/helps form the distal telescoping member 103-D.

In one embodiment, the spring-like section 140 and the distal anchor attachment section 136 of the distal backbone are made from a single tubing member and cut (e.g., laser cut) into the distal backbone 106. The cut patterns of these two sections of the distal backbone 106 may be the same or different, as desired to provide the desired flexural, support, attachment and protective characteristics to the distal portion of the device 100. Similarly, the portion of the distal backbone 106 where stop 134 is formed thereon or attached thereto may be cut in a pattern to aid the attachment process or remain uncut (e.g. if the stop 134 is a larger OD portion of a distal backbone tubing prior to its cutting or an uncut surface is suitable for the stop attachment process). Alternatively, the spring-like section 140, the stop 134 and the distal anchor attachment section 136 may be made of several tubes, wire forms or other materials of different configurations welded or otherwise joined together.

The proximal telescoping member 103-P includes as a part of its construction a portion of the proximal backbone 138 which is comprised of proximal anchor attachment section 114, a spring-like section 104 and an attachment section 108 (FIGS. 1-2 and 7-8). A cord locking mechanism 116 can be coupled to the section 108. The cord locking mechanism 116 (its outer housing) can be a part of the proximal backbone 138 as the section 108 or a separate attached device 116 coupled thereto as shown in FIGS. 7-8. The proximal backbone 138 may be a single structure (cut from a single tube) that may include the outer housing or other portion of a cord lock device, an area for proximal anchoring member attachment section 114, and a spring-like section 104 that supports/helps form the proximal telescope 103-P. The proximal anchoring member 112 is attached to the proximal backbone 138 at proximal anchor attachment section 114 and the distal anchoring member 142 is attached to the distal backbone 106 at distal anchor attachment section 136 as illustrated in FIGS. 7-8.

The spring-like section 104, the proximal anchor attachment section 114 and attachment section 108 (or the outer housing of the cord locking mechanism 116) of the proximal backbone 138 may be made from a single tubing member and cut (e.g., laser cut) into appropriate configurations for each component of the proximal portion of the device 100. Alternatively, the spring-like section 104, the proximal anchor attachment section 114 and the attachment section 108 (or the outer housing of the cord locking mechanism 116) may be made from several tubes, wire forms or other constructions of different configurations welded or otherwise joined together to form the proximal backbone 138.

Figure 2:
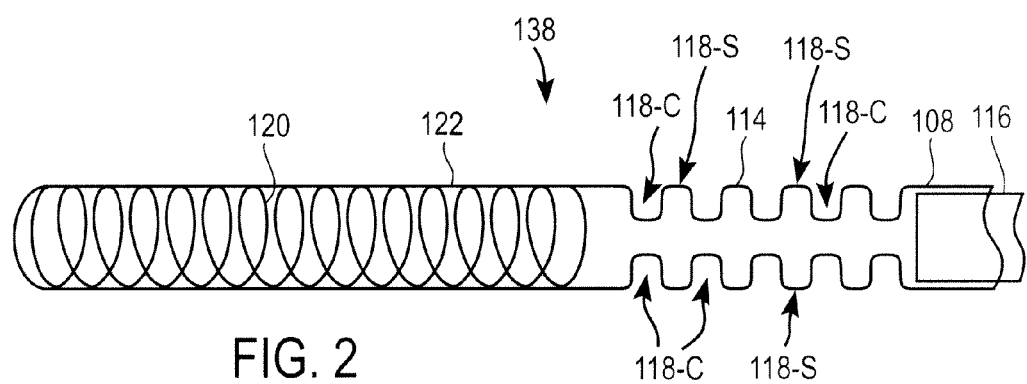

The spring-like sections 140 and 104 are positioned to be between the cord and the vessel wall when the device 100 is deployed and cinched in a vessel). Turning to FIGS. 1-2 and 6, the spring-like section 140 and the spring-like section 104, each includes a spring-like design 120 (similar to a slinky, a helical structure), a stent-like structure and/or a structure with a continuous portion (a spine) or discontinuous portions (links) that are positioned to be between the cord and the vessel wall when the device is deployed and cinched in a vessel. Each of the spring-like sections 104 and 140 is formed within, attached to or impregnated with a jacket 122 (FIGS. 1-2). The jacket 122 can be made of plastic materials, woven materials, porous materials or other suitable materials (e.g., polyurethanes, other polymers, a woven Dacron, silicone, or pacing lead coating materials and combinations of such materials). The jacket 122 is preferably made of a material into which tissue may grow. Such an ingrowth of tissue, incorporation of the device into the vessel wall and/or remodeling of the vessel wall and the surrounding tissues will provide support to the deployed and cinched device, and thus limit the forces applied to the cord and the motion applied to the device, increasing its life. In fact, such an ingrowth of tissue, incorporation of the device into the vessel wall and/or remodeling of the vessel wall and the surrounding tissues may maintain the vessel's cinched length and/or the valve's reshaping in the event of a cord break or other damage or wear to the device. Additionally, the ingrowth of tissue and/or incorporation of the device 100 into the vessel wall provides a superior anti-thrombogenic surface to the blood flow in the vessel, reducing the likelihood of thrombosis on the device generating a vessel occlusion or emboli.

In one embodiment, the jacket 122 includes an eluting bioactive substance(s)/coating(s) and/or a substance(s)/coating(s) that elutes a bioactive substance(s) during its (their) degradation, which, for example, limits clot formation and/or encourages appropriate tissue ingrowth and/or provides suitable scaffolds for tissue ingrowth or a therapeutic/diagnostic agent. In addition, the jackets 122 of the spring-like section 140 and the spring-like section 104 may include overlapping sections (not shown) of jackets 122 in the deployed and cinched device 100 to facilitate the joining of the distal telescoping member 103-D to the proximal telescoping member 103-P. In one embodiment, the proximal anchoring member 112 and/or the distal anchoring member 142 include an eluting bioactive substance(s)/coating(s) or substance(s)/coating(s) that elute a bioactive substance(s) during its (their) degradation, which, for example, limits clot formation and/or encourages appropriate tissue ingrowth and/or provide suitable scaffolds for tissue ingrowth. In one embodiment, the proximal and/or distal anchoring members (112, 142) may include a cover (similar to those on covered stents) and/or an expandable jacket similar to the previously described jacket 122.

In one embodiment, the spring-like design 120 provides a substantially round, elliptical, oval or other curved cross-sectional shape to the telescoping members so that forces applied to a vessel (not shown) by the device 100 can be distributed more evenly and over a sufficient surface area to prevent undesired tissue damage and/or compression/occlusion of vessels in adjacent tissues. In one embodiment, the spring-like design 120 provides a portion or portions that contact the cord and/or guide the cord within the device 100. Additionally, the spring-like design 120 also provides a flexible structure for the device 100 and yet is not easily crushable or deformed in its profile (e.g. round, elliptical or oval cross-section). The coil or cut-out shapes of the spring-like design 120 are designed to provide optimal telescope shape/profile support for the distribution of cinching forces to the vessel wall, provide a wear barrier between the cord and the vessel wall and still provide sufficient device flexibility to aid in the delivery of the device, for the device to conform to a curved vessel, and for the device to flex with cord cinching or in response to the motions of the heart.

Figure 4:
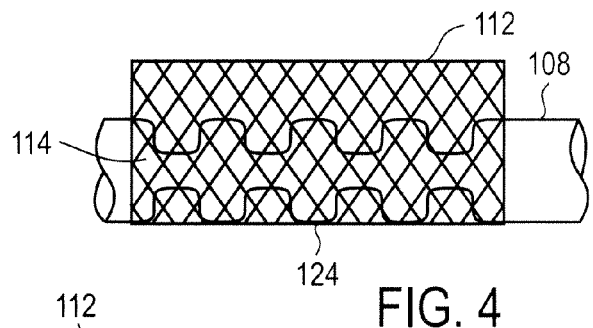
Figure 3:
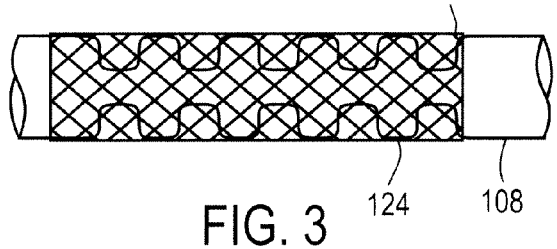

In one embodiment, the proximal anchor attachment section 114 includes a plurality of cutout sections, portions or grooves 118-C (FIG. 2). The cut out sections 118-C give the proximal anchor attachment section 114 some flexibility to allow it to better conform to the vessel wall in the deployed device. In addition, the non-cut out section(s) (as shown, generally referred to as ring-like sections with joining links or spines 118-S) provides a structural element (for example, links or spine(s)) to resist longitudinal deformation in response to cinching forces/distribute cinching forces to the proximal anchoring member 112. The spine(s) or the ring-like sections 118-S of the proximal anchor attachment section 114 provide attachment points 124 for the proximal anchoring member 112 to attach to the proximal anchor attachment section 114. FIGS. 3-4 show the proximal anchoring member 112 (in its collapse state and expanded state, respectively) being attached to the proximal anchor attachment 114 at the attachment points 124. There may be one or more attachment points 124.

In one embodiment, the proximal backbone includes an attachment section 108 with no cutout or no grooves. The section 108 may provide at attachment point to another device that needs to be coupled to the proximal portion of the device 100. In one embodiment a cord locking mechanism 116 (previously described e.g., in the U.S. patent application Ser. No. 10/740,360) is coupled to the proximal portion of the device via the section 108 of the proximal backbone. The proximal backbone 138 thus also provides an integration point for connecting the proximal anchoring member 112, which is flexible, to another component of the device 100 that is stiff, such as a cord locking mechanism 116. In other embodiments, section 108 may be configured to comprise the outer portions cord locking mechanism 116 and/or may be configured with slots or grooves to aid in its mating with a portion of a delivery system or other devices.

Although the embodiments above describe that the section 108 is provided at the proximal end of the device and proximal to the proximal anchoring attachment section 114 and provides an integration point for a locking mechanism 116 (or other devices) to be coupled to the device 100, it may be suitable to provide such similar section 108 between the proximal anchor attachment section 114 and the spring-like section 104. Thus, it is possible to provide a location for the locking mechanism 116 (or other devices) distal or just immediately distal to the proximal anchor attachment section 114 (FIG. 12A). In FIG. 12A, all components are similar to the device 100 described with a section 117 provided immediately distal to the proximal anchor attachment section 114 where the locking mechanism 116 is placed. A "mating section" 189 may be provided and configured to couple, cooperate or mate with a portion of the device delivery system, as will be described subsequently.

In one embodiment, the distal backbone 106 includes a plurality of cut out sections, portions or grooves 110-C (FIG. 6). The cut out sections 110-C give the distal anchor attachment section 136 some flexibility to allow it to better conform to the vessel wall in the deployed device. In addition, the non-cut out section(s) (rings and a spine(s) and/or links) 110-S provide a structural element to resist longitudinal deformation in response to cinching forces and to distribute cinching forces to the distal anchoring member 142. The spine(s) or the ring-like sections 110-S of the distal anchor attachment section 136 provide attachment points 125 for the distal anchoring member 142 to attach to the distal anchor attachment section 136. FIGS. 6-8 show the distal anchoring member 142 (in its collapsed state in FIG. 7 and in its expanded state in FIGS. 6 and 8) attached to the distal anchor attachment 136 at the attachment points 125. There may be one or more attachment points 125.

An adjustment of the length of the telescoping assembly 103 may occur after the deployment (and expansion) of the distal anchoring member 142 and prior to the deployment (and expansion) of the proximal anchoring member 112 to position the proximal anchoring member 112 in a vessel or vessel ostium at the desired position. The proximal anchoring member fixes the position of the proximal end of the device in the vessel. Once the distal and proximal ends of the device are fixed in the vessel (anchors expanded), the cord is pulled relative to the proximal portion of the device (cinched) to set the final maximum length of the device. During cinching, the length of the telescoping assembly 103 shortens.

The anchor attachment sections and the spring-like sections (140 or 104) of the respective proximal and distal backbones may be similar, identical, of different designs and/or rotated relative to each other. All that is required is that the proximal and distal backbones have some cut out or other sections (e.g. a coil-like section) that can provide enough flexibility to allow the anchoring members to be delivered into position in the anatomy and that the spring-like structures be able to support and distribute the forces of a cord disposed and cinched within the device 100. Furthermore, the backbone sections' configurations, while providing flexibility for delivery, also provides support and attachment points (e.g. welding, brazing, soldering, adhesive bonding) for the distal and proximal anchoring members and helps the anchoring members in resisting buckling and deformation that may be caused by the cinching of the cord disposed within the device 100.

In some embodiments, a true spring-like structure in the sections of the device 100, where the distal anchoring member 142 and the proximal anchoring member 112 are located/attached, may be optional. A spring-like structure tends to deform in the direction of a force such as forces caused by cinching the cord 126 of the deployed device 100. Thus, when the cord 126 is being pulled relative to the proximal portions of the device (cinched) to adjust the total length of the device 100, the distal anchoring member 142 and the proximal anchoring member 112 may be compressed or stretched if they are attached to a true spring-like section. On the other hand, an anchor attachment section with cut-out sections and, at least one spine, as previously discussed, will provide flexibility but little or no effective compressibility or stretchability. Thus, backbone sections with cut out sections or grooves (ring-like structures) and at least one spine section can provide flexibility and support desirable for the anchoring member attachments. The distal anchoring member 142 and the proximal anchoring member 112 can be attached to such sections for their flexibility (provides the ability for their attachment sections to more easily conform to the vessel wall when their anchors are deployed/expanded), but without their length being appreciably affected by the force of a cinched cord. Additionally, in some anchor member designs, the multiple attachment points provided by such an attachment section design may provide for the distribution of the cinching force over the anchor's length or a portion of its length. In addition, the anchor attachment sections and other sections of the backbones can be shaped into curves, thus providing a desired deployed device rotational orientation bias and greater ease of device delivery into curved vessels.

As mentioned, the distal anchoring member 142 is coupled to the distal anchor attachment section 136 of the distal backbone and the proximal anchoring member 112 is coupled to the proximal anchor attachment section 114 of the proximal backbone. Each of the anchoring members 142 and 112 are collapsed or compressed onto or nearer to the corresponding anchor attachment section 136 or 114 (FIG. 7) and/or over the proximal and distal portions of device 100. A delivery catheter, sheath and/or sheaths (not shown) may be used to keep the anchoring members 142 and 112 in their collapsed states (initial states) until deployment. Upon deployment, the anchoring members are expanded or allowed to expand similar to a self-expanding stent (e.g., by removing/withdrawing the delivery sheath) (FIG. 8).

In one embodiment, the distal anchoring member 142 and the proximal anchoring member 112 are made of a shaped-memory or super-elastic material such as Nitinol (or NiTi) and each is welded to the corresponding anchor attachment sections 136 and 114. The anchoring members 142 and 112 can also be made of other super-elastic materials or other materials used to make a conventional stent. In one embodiment, each of the proximal anchoring member 112 and the distal anchoring member 142 is a stent-like structure that includes struts. The anchoring members 112 and 142 are attached to their respective backbone anchor attachment sections 114 or 136 by the struts of the stent or the stent may be configured to have attachment pads, a spine(s), rings and links and/or other attachment facilitating configurations. The anchoring members 142 and 112 are attached to the respective backbone's anchor attachment section on one side of the anchoring members 142 and 112 so that they can expand as shown in FIG. 8. Both of the anchoring members and the backbone sections may be comprised of similar materials that may include metals or metal alloys, NiTi, or stainless steel. Thus, the anchoring members can be attached to the backbone sections using processes such as welding with little concern for bimetallic corrosion processes.

In one embodiment, the telescoping assembly 103 includes a stop 134. The stop 134 is placed on the distal telescoping member 103-D. The stop 134 sets the minimum possible length of the device 100. At this minimum length, the distal end of the proximal telescoping member 103-P hits or encounters the stop 134 and prevents the proximal telescoping member 103-P from moving further distally. The stop 134 also prevents the proximal telescoping member 103-P from interfering with the distal anchoring member 142. Additionally, at the minimum length, the proximal end of the distal telescoping member 140 may be near the distal end of the cord locking mechanism 116, but sufficiently far apart to not interfere with the operation of the locking mechanism.

Figure 9A:
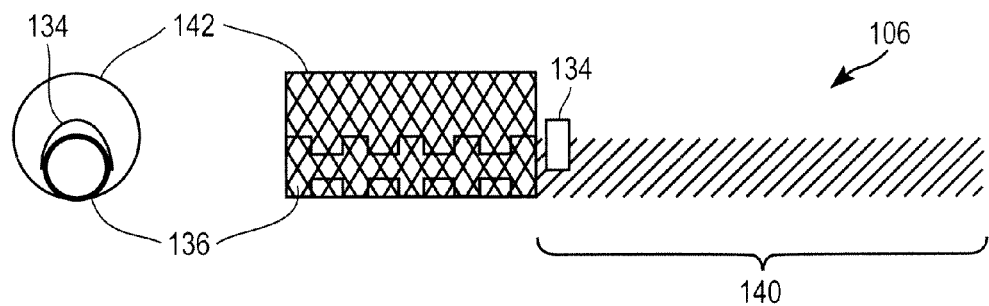
FIGS. 9A-9B illustrate exemplary configuration of a stop that can be used with the telescoping assemblies.
Figure 9B:
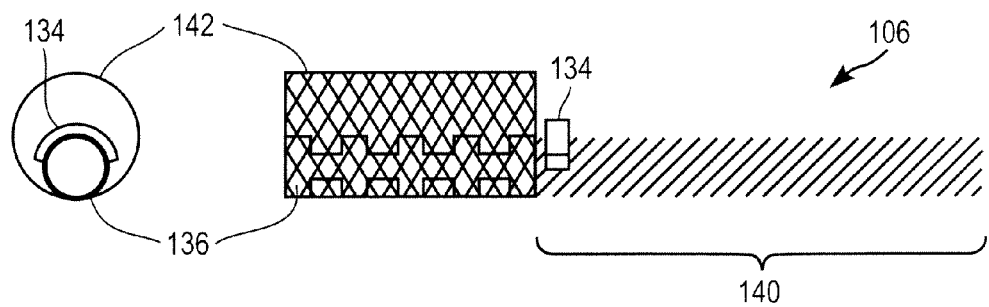

In one embodiment, the stop 134 is configured to not protrude beyond the maximum radial expansion of the device. The stop 134 is configured such that it will not have a raised portion (as illustrated in FIGS. 6-8 and 12A) that will press into the vessel wall when device 100 is deployed in the desired orientation in the vessel (FIGS. 9A-9B). If portions of stop 134 are pressed into the vessel wall, the vessel wall may be damaged or worn or adjacent structures, such as adjacent blood vessels, compressed to an unacceptable degree. FIGS. 9A-9B each shows a two-orthographic representation of the distal backbone 106 with the distal anchoring member 142 attached that are drawn similar to that of FIG. 6, but shows a stop 134 with a configuration and dimension that will not press into the vessel wall when the device is deployed.

In one embodiment, the distal end of a first sheath (or other device, such as a wire) engages at least a portion of the proximal side of the stop 134 and holds the distal end of the device fixed in position while a second sheath (or other device, such as a catheter, over the first sheath or other device) is withdrawn to deploy the distal anchoring member 142. Such an arrangement allows the telescope 103 to be held at or near its maximum length and, therefore, at its most flexible, during the positioning and deployment of the distal anchoring member 142 in the vessel. In other embodiments, where the ID of the proximal telescope 103-P engages the OD of the of the distal telescope 103-D, the stop 134 is mounted on/a part of the proximal telescope 103-P.

In one embodiment, a cord 126 is disposed within the telescoping assembly 103 (FIG. 5A). The cord 126 allows for adjustment, tightening, or cinching of the components of the device 100, as previously described. The cord 126 is affixed to a distal point in the device 100; for instance, the cord 126 is attached to a proximal location in the distal anchor attachment section 136 as shown in FIGS. 7-8. In other configurations, the cord 126 may be attached to the distal backbone at some point in the distal telescoping member 103-D (not illustrated). FIG. 5A illustrates a cross-sectional view with the cord 126 disposed in the device 100 cutting through the proximal telescoping member 103-P and the spring-like section 104 of the proximal backbone. The spring-like section 104 of the proximal backbone includes the spring-like design 120 and the outer jacket 122 as previously described. In addition, a lubricious lining 130 may be provided to line a lumen 131. The spring-like design 120 layer of the proximal backbone 138 is disposed between the outer jacket 122 and the lubricious lining 130. The cord 126 is confined within the lumen 131. The lumen 131 may extend longitudinally through the telescoping assembly 103 and to the cord attachment point on the distal backbone 106. The distal telescoping member 103-D in a cross-sectional view can be similar to that illustrated at FIG. 5A. In this embodiment, the inner diameter (ID) of lumen 131 in the distal telescoping member 103-D is smaller than in the proximal telescoping member 103-P.

Similar configurations to FIG. 5A can also be applied to all components of the device 100 that are exposed to the cord 126. For instance, in one embodiment, the spring-like structure 140, attachment section 108 and cord locking mechanism are lined with a lubricious lining similar to or the same as the lining 130. In the present embodiment, the cord 126 can move within the spring-like structure 104 and 140. In another instance, the distal backbone 106 is lined with a lubricious lining similar to or the same as the lining 130.

In one embodiment, the cord 126 may be provided with a lubricious coating 128. The lubricious properties of the cord coating 128 and/or the lining 130 reduce the friction between the cord 126 and the other portions of the device 100 that the cord 126 contacts and thus, reduces the rate of or delays the wear caused by cord 126 movement within the device 100 (FIG. 5A).

In one embodiment of the distal telescoping member 103-D, the cord 126 may be constrained within the ID of the distal telescoping member 103-D. For instance, the cord 126 can be impregnated or incorporated into a portion of jacket 122 that flows within the spring-like design 120 of the spring-like section 140 of the distal backbone 106 as shown in FIG. 5B. In these embodiments, lumen 131, lubricious lining 130 and lubricious coating 128 may be omitted in the distal telescoping member 103-D as shown in FIG. 5C. With the cord 126 constrained from appreciable movement within the distal telescoping member 103-D, the rate of wear caused by cord movement within it is much reduced.

In FIG. 10, several examples of a telescoping assembly are illustrated. Although the examples contain two and three telescoping members, the concepts may be easily generalized to the permutations available with greater numbers of telescoping members. A telescoping assembly 144 includes a distal telescoping member 144A, a proximal telescoping member 144B, and a middle telescoping member 144C. The middle telescoping member 144C slides into and out of each of the distal and proximal telescoping member 144A and 144B to adjust for the total length of the telescoping assembly 144. Alternatively, as shown in telescoping assembly 149 the telescoping members can be made so that the distal member 149A is smaller so that it can slide into and out of the middle member 149C. This configuration may be preferred, as it may be designed to shorten the greatest amount for any given assembly maximum length. A telescoping assembly 146 includes a distal telescoping member 146A, a proximal telescoping member 146B, and a middle telescoping member 146C. The telescoping members 146A and 146B slide into and out of the member 146C to adjust for the total length of the telescoping assembly 146. A telescoping assembly 148 includes a distal telescoping member 148A and a proximal telescoping member 148B, with the member 148A sliding into and out of the member 148B to adjust for the total length of the telescoping assembly 148. In any of the examples, the total length of the telescoping assembly and the amount of shortening possible is controlled by the actual lengths of each individual telescoping member. When the telescoping members slide out of each other, they may be configured to remain engaged with each other and not to separate, as is well known in the art, such as by ID/OD interferences (not shown), as used in the design of telescoping car antennas. In telescoping assemblies with three or more telescoping members, this configuration is preferred.

In one embodiment, the cord, such as the cord 126 of the device 100 is configured so that the cord 126 allows the device 100 to extend to a total length that is longer than the combination of the lengths of all the other components of the device. For instance, the cord 126 of the device 100 is configured to allow the telescoping members of the device 100 to slide completely out of each other such that there is a mid-section of the device 100 that includes just a portion of the cord 126 with no telescoping member. FIGS. 11A-11D illustrate and compare a device that has its total length extended by an exposed mid-section of cord to a conventional telescoping assembly.

FIGS. 11A-11D compare the range of adjustment allowed by having a portion of the cord 156 exposed between in the telescoping members prior to cinching. A telescoping assembly 168 is illustrated and includes a distal telescoping member 168A and a proximal telescoping member 168B. The maximum length $L_{max}(168)$ of the telescoping assembly 168 is achieved when the distal telescoping member 168A and the proximal telescoping member 168B slide out of one another, but still engage to one another (overlap) at a short portion of their length with no exposed cord between the telescoping members (FIG. 11A). The minimum length $L_{min}(168)$ of the telescoping assembly 168 is achieved when the distal telescoping member 168A and the proximal telescoping member 168B slide into one another almost completely or completely (FIG. 11B).

Comparing the telescoping assembly 150 to the telescoping assembly 168, the telescoping assembly 150 includes an exposed cord section. The maximum length $L_{max}(150)$ of the telescoping assembly 150 is achieved when the distal telescoping member 152 and the proximal telescoping member 154 slide out of one another with no portion engaging one another and a cord section is exposed between the two telescoping members (FIG. 11C). The minimum length $L_{min}(150)$ of the telescoping assembly 150 is achieved when the distal telescoping member 152 and the proximal telescoping member 154 slide into one another almost completely or completely (FIG. 11D). Comparing to the telescoping assembly 158, the individual telescoping members of the telescoping assembly 150 can have much shorter length and still achieve the same length prior to cinching as the telescoping assembly 168 ($L_{max}(150)=L_{max}(168)$). However, telescoping assembly 150 can have a greater cinching capability than the telescoping assembly 168 (e.g., $L_{min}(150)<L_{min}(168)$).

As can be seen, there is much more range of adjustment for the telescoping assembly 150 compared to the telescoping assembly 168. For instance, there can be much more shortening or cinching in the telescoping assembly 150. Thus, there is a greater cinching percentage or cinching ability for the telescoping assembly 150 even with shorter individual telescoping members. In some embodiments, it is desirable to have the device configured such that a portion of the cord is exposed between the telescoping members during device delivery and, in some cases, just prior to cinching (device shortening to change the length and/or shape of the vessel and/or adjacent structures, like a valve annulus). The advantage during delivery is that the telescoping members are not engaged with each other and, thus don't create a stiff portion (portion were two telescoping members overlap) that may impede the delivery of the device into tortuous vasculature. The advantage during cinching is that the telescoping members may be made shorter, thus the cinched device may be shortened to a shorter length than a similar device that was designed with longer telescoping members to ensure that the cord was never exposed to the vessel wall during cinching. The ability to shorten to a shorter device length increases the range of vessel lengths that may be treated by a single device design and increases the amount of shortening that may be applied by the device to a vessel/structures adjacent to a vessel.

The maximum amount of the portion of the cord that can be exposed in a device is limited to the forces/pressures that the wall of the vessel within which the device is deployed can accommodate during the cinching and the minimum amount of cinching that may be required. It is preferred that the cinched device doesn't expose a portion of the cord between the telescoping members. Thus, when cinched, it is preferred that the device be shortened by, at least, the length of the exposed cord between the telescoping members. Additionally, it is preferred that during the cinching (device shortening) that the vessel wall in contact with the cord is not significantly damaged. Thus, the exposed length of the cord between the telescoping members is preferred to be limited, such that the cinching forces are limited and thus, the pressure applied by the exposed cord to the vessel wall are limited and don't reach levels at which significant vessel wall damage will occur during the cinching and cinching removes any cord exposure to the wall of the vessel.

In many instances, several portions of the device can be made from one tube. FIG. 12B is a three-view orthographic representation of one embodiment of a finished distal backbone 2101 that can be used for the device 100 described above. The distal backbone 2101 is cut from one piece of tube and the backbone is a single piece after it is cut and the cutout pieces are removed. In this example, the tube is a NiTi tube or other superelastic material. The distal portion of the tube is cut in the configuration of the distal anchoring member 2102 and the proximal portion of the tube is cut in the configuration of a spring-like section 2105. A connecting portion 2108 shown between the proximal end of the distal anchoring member 2102 and the distal end of the spring-like section 2105 is shown at a length sufficient to show the separation of these components in this illustration, but it may be made any length or as small as the cutting width. In some embodiments, the connecting portion 2108 may have a complex shape, such as a shape with fingers radiating out to a portion of the OD of the proximal end of the distal anchoring member 2102 to distribute the cinching forces and/or a long and curved shape to allow the distal anchoring member 2102 to be placed in a more distal portion of the anatomy, such as the Great Cardiac Vein. Because the distal anchoring member 2102 is an integral part of the distal backbone 2101, no distal anchor attachment section is required.

In one embodiment, distal end of the spring-like section 2105 or the proximal end of distal anchoring member 2102 or connecting portion 2108 may include a feature (not shown), such as a welding pad(s), a slot(s), a hole(s) and/or a cut shape(s) to accommodate or assist in the attachment of the distal end of the cord to the distal backbone 2101 at its preferred attachment location. In embodiments where connecting portion 2108 is long, it is preferred that the distal end of the cord is attached to the distal end of the spring-like section 2105 or the proximal end of connecting portion 2108 so that connecting portion 2108 is placed in tension by cinching and, therefore, may have a relatively thin cross-section and be flexible (bend) during positioning and when deployed.

In one embodiment, distal end of the spring-like section 2105 may include a feature (not shown), such as a welding pad, a slot, a hole and/or a cut shape to accommodate or assist in the attachment of a stop (similar to the stop 134 previously shown). In other embodiments, the OD or part of the OD of the tube at or near the distal end of spring-like section 2105 may be increased and the stop cut from this portion. In another embodiment, distal end of the spring-like section 2105 may include a feature (not shown), that is expanded and heat set to form or help form, at least, a portion of a stop. As previously described, a stop is not always a necessary feature to be included in a device.

In this example, the design of the spring-like section 2105 is that of rings 2103 joined by a spine 2104, but a very large number of different designs and dimensional variations are possible, as previously discussed. The design of the distal anchoring member 2102 is as previously discussed. The design of the spring-like section 2105 is contiguous with the design of the connecting portion 2108 and the design of the connecting portion 2108 is contiguous with the design of the distal anchoring member 2102.

After the cutting, at least a portion of the backbone 2101 is held by a holding mechanism(s) that holds it in the desired finished shape(s) and it is heated to set its held shape(s), as is well known in the art. There may be several holding mechanisms and several heating/cooling steps to attain the desired final free (unconstrained) shape(s) of backbone 2101. At a minimum, in this example, the distal portion of the tube must be expanded and set to attain the desired free OD of the distal anchoring member 2102. If anchors, barbs, or hooks are included as a part of the design of distal anchoring member 2102, they will need to be heat set to protrude, as desired, from the OD of distal anchoring member 2102 and/or to shape them as desired (for example, a hook shape). If an oval, elliptical or other cross-sectional shape is desired for the distal telescope, then spring-like section 2105 may be heat set to that shape. Examples a few possible cross sections of the spring-like section 105 are shown in FIG. 12C. If a longitudinal curved shape is desired, spring-like section 105 and/or distal anchoring member 2102 may be heat set to the desired curvature(s).

FIG. 12B is a 4-view orthographic representation of one embodiment of a finished proximal backbone 2201 that can be used with the device 100. The proximal backbone 2201 is cut from one piece of tube and the backbone is a single piece after it is cut and the cutout pieces are removed. In this example, the tube is a NiTi tube or other superelastic material. In the preferred embodiment, as shown, the proximal portion of the tube is cut in the configuration of the proximal anchoring member 2202, the mid portion of the tube is cut in the configuration of the outer housing of the locking mechanism 2206 and the distal portion of the tube is cut in the configuration of a spring-like section 2205. In another embodiment, the positions of the proximal anchoring member 2202 and locking mechanism 2206 are reversed, as previously described for the device 100. Because the proximal anchoring member 2202 is an integral part of the proximal backbone 2201, no proximal anchor attachment section is required. In this example, the design of the spring-like section 2205 is that of rings 2203 joined by a spine 2204, which is the same configuration as spring-like section 2105, except that their dimensions are chosen such that the resulting proximal telescope from section 2205 will fit over the OD of the resulting distal telescope from section 2105, which is preferred. In another embodiment, their dimensions are chosen such that the resulting distal telescope from section 2105 will fit over the OD of the resulting proximal telescope from section 2205. It is probably worth noting that it is preferred that the cuts made in a backbone 2101 or 2102 include radiuses (not shown) and/or curves to avoid stress concentrations that may lead to early fatigue fractures or fractures related to the torturous path and bending of the finished device during its delivery and/or after deployment, as is well-known in the art of stent design. In this example, the locking mechanism 2206 is shown with alignment slots 2207 similar to the alignment slot or slots 328 of FIG. 26 (below) to mate with an inner member with a slightly different configuration on its distal end than shown in FIG. 26 (configuration of inner member engage section 322 is modified in the obvious manner). In this example, when the proximal anchoring member 2202 is held in a collapsed state by the delivery catheter or a sheath, it is collapsed over/near to the OD of the inner member. The connecting portion 2208 shown between the distal end of the proximal anchor 2202 and the proximal end of the outer housing of the locking mechanism 2206 is shown at a length sufficient to show the separation of these components in this illustration, but it may be made any length or as small as the cutting width. In some embodiments, the connecting portion 2208 may have a complex shape, such as a shape with fingers radiating out to a portion of the OD of the distal end of the proximal anchoring member 2202 to distribute the cinching forces and/or a long and curved shape to allow the proximal anchor to be placed in a more proximal portion of the anatomy, such as the Superior Vena Cava. In this embodiment, connecting portion 2208 is placed in tension by cinching and, therefore, may have a relatively thin cross-section and be flexible (bend) during positioning and when deployed. Thus, this relative positioning of the proximal anchoring member 2202 and locking mechanism 2206 is preferred in these embodiments. In a less preferred embodiment, where the proximal anchoring member 2202 and locking mechanism 2206 positions are reversed, the analogous connecting portion 2208 is placed in compression by cinching, requiring a thicker cross-section and/or larger shape to avoid buckling and/or being pulled into a highly bent/stressed state. As was previously described in relation to the distal backbone 2101, the shape of the various portions of the proximal backbone 2201, including the outer housing of the locking mechanism 2206, may be heat set to the desired shape(s) after cutting.

Figure 13A:
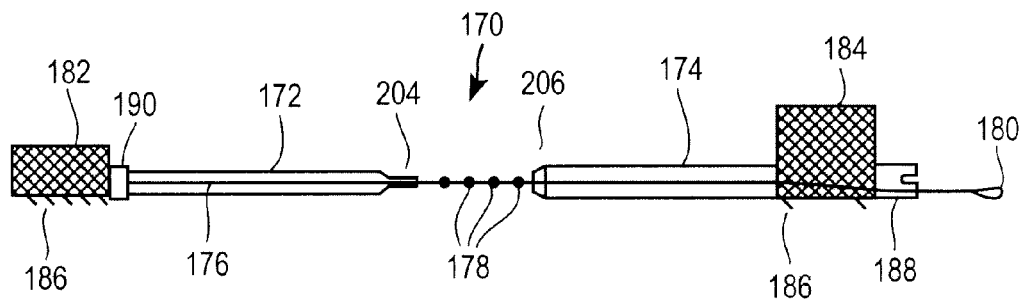
FIGS. 13A-13B and 14 illustrate a device having a proximal anchoring member, a distal anchoring member, a telescoping assembly, and a backbone included with the telescoping assembly, wherein a cord is used for length extension and/or flexibility.
Figure 13B:
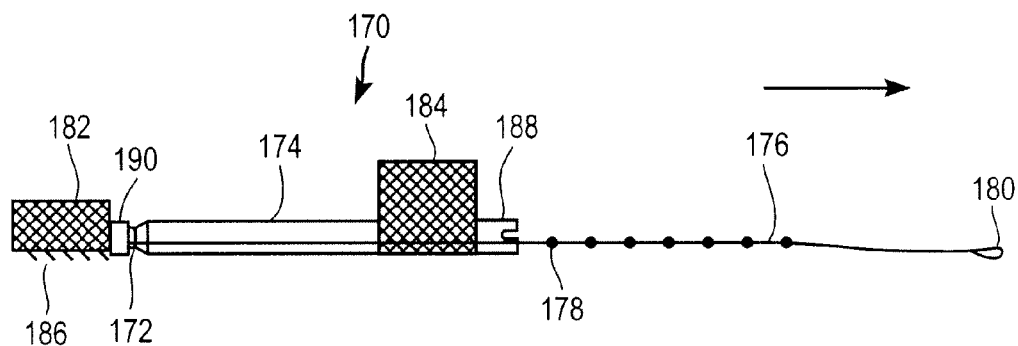

FIGS. 13A-13B illustrate an exemplary device 170 similar to the device 100 except the telescoping assembly and the cord for the device 170 is configured to provide a cord exposure for added capabilities discussed above. Additionally, the device 170 includes a distal telescoping member that is provided with a tapered proximal end so that the distal telescoping member can easily slide into the proximal telescoping member of the device 170. It is to be understood that features of the device 170 can be added to the device 100, and vice versa.

The device 170 includes a cord 176 disposed in a telescoping assembly which includes a distal telescoping member 172 and a proximal telescoping member 174 as illustrated in FIG. 13A. The cord 176 is attached at its distal end to the distal end of the distal telescoping member 172 and runs through a locking member 188. The cord 176 is configured to be exposed when the distal telescoping member 172 and the proximal telescoping member 174 disengage one another, such as when mounted in a delivery catheter or system (not shown). The device 170 includes a distal anchoring member 182 affixed to a distal portion of the distal telescoping member 172 similar to previously described for the device 100. A set of anchors, barbs, or hooks 186 can be included with the distal anchoring member 182 to help station or secure the distal anchoring member 182 within a vessel. The device 170 also includes a proximal anchoring member 184 affixed to a proximal portion of the proximal telescoping member 174 similar to previously described for the device 100. The proximal anchoring member 184 can also include hooks/barbs/anchors 186 similar to the distal anchoring member 182. A locking member 188 is also included. A cord loop 180 is also included at the proximal end of cord 176 to allow the cord 176 to be releasably connected to a pulling device (which can be a part of a delivery catheter or system, not shown) for cinching of the telescoping members 172 and 174. In one embodiment, the OD of the cord loop 180 is configured to not be able, (e.g., by being too large), to pass through the locking member 188, thus the proximal and distal portions of device 170 will not become disconnected from each other. The cord 176 can be configured so that it works cooperatively with the locking member 188 to prevent locking the device 170 at a cinched length that leaves a portion of the cord 176 exposed. In one embodiment, the OD of the cord 176 just distal to the cord loop 180 for a length at least equal to the length of the exposed cord 176 is small enough to pass through the locking member 188, (in the proximal direction) but too large and/or high modulus to allow the locking member 118 to be locked (restrict or prevent cord 176 motion relative to the locking member 188). Thus, it may be ensured that device 170 cannot be locked at a cinched length that leaves a portion of the cord 176 exposed. Bumps 178 are also provided on the cord 176. The bumps 178 are provided to provide locking points of the cord 176 similar to previously disclosed in U.S. patent application Ser. No. 10/740,360 incorporated herein. In other embodiments, other features similar to previously disclosed in U.S. patent application Ser. No. 10/740,360 may be incorporated into cord 176. A distal stop 190 is provided at the proximal end of the distal anchoring member 182 to prevent proximal telescoping member 174 interference with the distal anchoring member 182 and also to set the minimum length for the device 170 (FIG. 13B).

Figure 15:
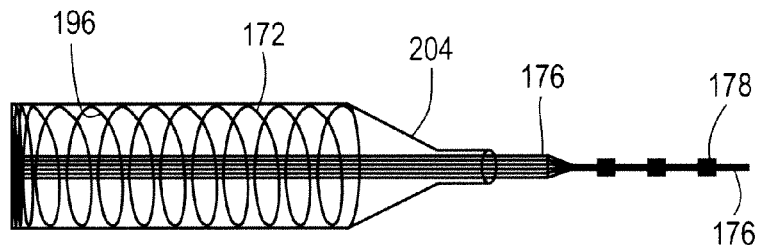
FIGS. 15-16 illustrate in more detail of exemplary components of a telescoping assembly.
Figure 16:
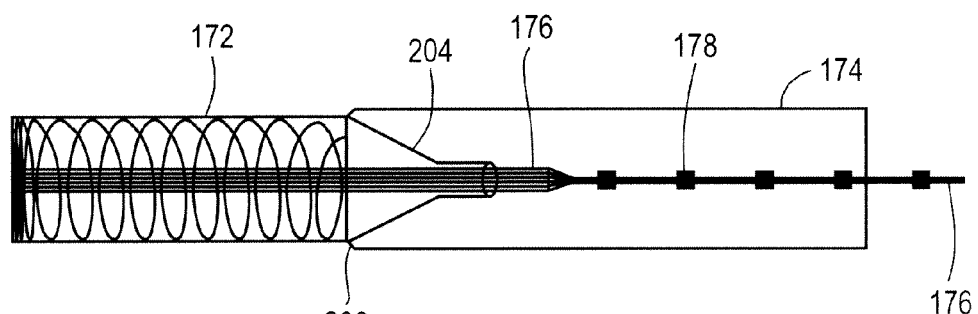

The distal telescoping member 172 includes a tapered proximal end 204 (FIG. 13A and larger view in FIG. 15). The tapered proximal end 204 has an ID that fits closely to the OD of the cord 176 such that the distal telescoping member 172 can be guided into the ID of the proximal telescoping member 174 during cinching. In some embodiments, the OD of cord 176 for a length proximal of the tapered proximal end 204 or the OD of the tapered proximal end 204 is too large to enter locking member 188. In this case, the lengths of the telescoping members 172 and 174 and/or the length of the cord too large in OD to enter locking member 188 may be chosen such that device 170 may not be cinched shorter than desired. Thus, the function of the stop 190 to limit the amount that the telescoping members may engage and thus, protect an anchor from contact with/damage from an outer telescoping member may be supplemented. In some embodiments, the proximal telescoping member 174 or an outer telescoping member also includes an atraumatic tapered, blunted and/or rounded distal end 206 that helps prevent significant damage to the vessel wall by the distal end 206 of the proximal telescoping member 174 during cinching (FIG. 13A).

Figure 14:
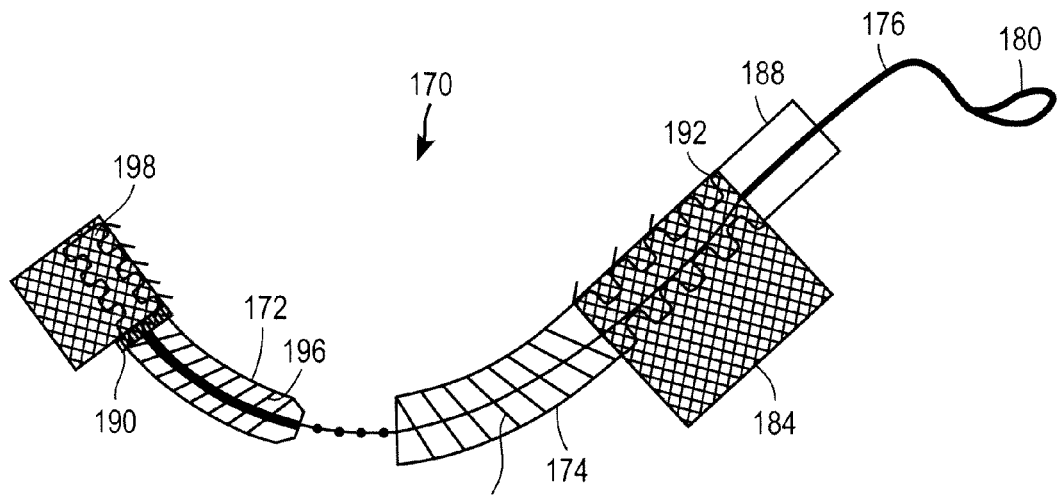

In one embodiment, the device 170 is preset to a bent or curved shape, for example, to resemble the curve of a coronary sinus or a vessel that the device 170 is delivered to. Presetting or pre-shaping a device can be done using various methods known in the art. The materials and material structures used to make the device 170 are chosen to allow for such shape setting or are designed to be fabricated with the desired shape or curvature as a part of their configuration. FIG. 14 illustrates the device 170 having been preset to have a curved shape. Similar to the device 100, the distal telescoping member 172 includes a spring-like structure 196 connected to an anchor attachment section 198. As before, the anchor attachment section 198 and the spring-like structure 196 can be referred to as the distal backbone of the device 170. The proximal telescoping member 174 includes a spring-like structure 194 connected to an anchor attachment section 192, which constitutes the proximal backbone for the device 170. These configurations provide flexibility, durability, and support for the device 170. Additionally, the design of spring-like structures 194 and 196 of the proximal and distal backbone minimize the potential problems associated with the sawing-like or rubbing motions of the cord 176, as previously described. The curvature of device 170 helps ensure that when device 170 is delivered into a curved vessel, such as the coronary sinus, that the orientation of delivered device 170 is controlled such that the curve direction of device 170 and the curve direction of the vessel are, at least roughly, aligned. Thus, the rotational orientation of device 170 and its features relative to the vessel and adjacent anatomy may be more easily controlled. The proper orientation of device features in the vessel and relative to the adjacent anatomy is often crucial to the safe and effective use of the device.

In many embodiments, the distal anchoring member and the proximal anchoring member are configured to provide resistance to dislodgement, longitudinal and/or rotational motion relative to a vessel or an adjacent anatomy when subjected to longitudinal or rotational forces after deployment. For instance, when deployed in a vessel, the distal anchoring member and the proximal anchoring member are essentially anchoring points so that the telescoping member disposed between the distal anchoring member and the proximal anchoring member can be adjusted, tightened, or cinched to produce an effect on the vessel or adjacent anatomy.

In many embodiments, it is desired to have the anchoring member to be able to withstand high forces and have the shortest length possible (e.g., about 15 mm or less). For instance, in the preferred two telescoping member design, the distal telescope moves into the ID of the proximal telescope during cinching. Thus, if the distal anchor were to be extended proximally over the distal telescope to increase its ability to withstand cinching forces, it could interfere with the motion of the proximal telescope over the distal telescope during cinching and limit the amount of cinching (shortening) that could be performed (for example, the stop must be placed more proximally). If the distal anchor were to be extended distally to increase its ability to withstand cinching forces, then the device length would be increased, making device delivery more difficult and limiting the anatomy into which the device may be placed (vessels often change size and direction rapidly, especially veins) or the amount that the device may be cinched (shortened). Experiments have been made with pressurized ex-vivo animal hearts to determine a range of longitudinal forces that the anchoring members may be subjected to. In many cases, it is desirable to have the anchoring members resist longitudinal forces from about 0.5 to about 2.0 lbs. A conventional small OD stent cannot reliably resist such high forces without being modified to have a much greater length than desirable. For instance, a conventional stent with a 10 mm free diameter and 30 mm length (e.g., self-expanding stent) can resist a longitudinal force less than 1 lb. when the stent is deployed in a blood vessel such as the distal coronary sinus or proximal great cardiac vein. Also, using a conventional self-expanding stent, such as the ACCU-LINK™, (ACCULINK is a trademark of Guidant Corporation) when the stent is deployed in the blood vessel and subjected to longitudinal forces sufficient to move it, the crowns of the stent penetrate/puncture the wall of the vessel, causing undesirable damage. Furthermore, it has been observed that the radial forces applied to the vein/sinus by the conventional 10 mm free diameter self-expanding stent tends to cause the vessel to be very distended, indicating that this is near the limit of the resistance to motion force that can be generated from the vessel wall by a conventional stent design of this length. Thus, it is unlikely that conventional stent designs at smaller OD's to prevent undue vessel distention/damage and shorter lengths can reliably function as anchors that can resist the required cinching forces in a desirable manner in the distal anchor position in the coronary sinus or great cardiac vein.

Figure 17:
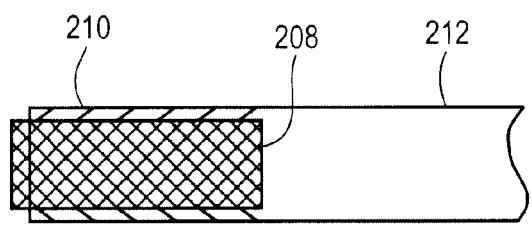
FIGS. 17-18 illustrate an exemplary embodiment of an anchoring member having anchors in according to embodiments of the present invention.
Figure 18:
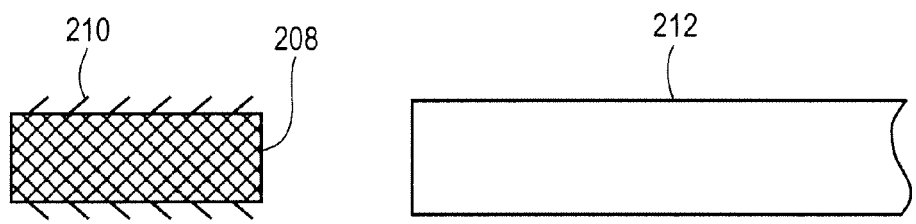

Exemplary embodiments of the present invention such as the device 100 or the device 170 or other devices herein may include anchoring members with hooks, barbs, or anchors to enhance their anchoring ability. FIGS. 17-18 illustrate an exemplary anchoring member 208 with a set of barbs, hooks, or anchors 210.

The anchoring member 208 can be the distal anchoring member or the proximal anchoring member previously described. The anchors 210 are compressible onto the top surface of the anchoring member 208. A retractable protective sheath 212, which can be a delivery sheath or catheter, is placed over the anchoring member 208 to keep the anchors 210 from protruding out during delivery. Upon deployment when the protective sheath 212 is removed proximally the anchors 210 move upward thus allowing the anchors to penetrate or puncture a vessel wall and adjacent tissue. The anchors 210 help the anchoring member 208 to resist dislodgement, longitudinal and/or rotational motion, thus stabilizing the anchoring member 208 within a vessel or at a particular location. The anchors 210 allow the anchoring member 208 to be short and small and yet provide greater longitudinal force resistance.

In one embodiment, the anchors 210 are placed only on one side of the anchoring member 208 (as opposed to at several locations around the anchoring member). This is because in certain applications, the anchors 210 only need to be or are desired to penetrate only on the certain side of the deployment site. In other embodiments, the anchors 21 are placed around the anchoring member 208 where needed.

FIG. 19 illustrates a view of an exemplary embodiment of an anchoring member such as a distal anchoring member 214 which has been cut at each ring connection to crowns 218 in a longitudinal line and laid out flat on the page. The distal anchoring member 214 includes anchors 220, crowns 218, rings 226 and spines (or links) 216 (a link connects two rings, a spine connects more than two rings). Additionally, the distal anchoring member 214 also includes one or more attachment spine 222. Each of the attachment spine 222 may include a set of attachment points 224. In one embodiment, the attachment points 224 are the locations where the distal anchoring member 214 attaches to a backbone section of a telescoping member (e.g., a distal anchor attachment section 125 of the distal backbone as previously described). The attachment points 224 can be pads, holes or openings where attachment materials (e.g., adhesive, solders, metals, strings, wires, pins, etc) are disposed therethrough or thereon or areas that provide anchoring member material for welds to couple the distal anchoring member to the backbone structure. In one embodiment, the attachment spine 222 design is indistinguishable from spine(s) 216. In other embodiments, the attachment spine 222, spines 216 and/or the proximal ring 226 may be contiguous or have contiguous portions with the backbone, as previously described relative to FIG. 12B and 12A.

In one embodiment, the anchors 220 are balancedly distributed on each side of the attachment spine 222. As mentioned, it may not be desirable to place the anchors 220 all around the distal anchoring member 214 especially when the distal anchoring member 214 is to be deployed in a vessel that has a free sidewall (e.g., a great cardiac vein or a coronary sinus), which, if punctured, could lead to tamponade, excessive bleeding or other adverse consequences. In such anatomy, the anchors 220 are placed on the side the distal anchoring member that faces the attached side of the vessel (the side of the vessel nearest the Mitral valve annulus) and/or the side of the vessel that the penetrating action of the anchors 220 does not cause undesired damage to adjacent vessels and anatomy.

The anchors 220 are configured with dimensions and projection angles (after the protective sheath is removed) so that the radial force generated by the distal anchoring member is sufficient to cause the anchors to press on the vessel wall but not to excessively distend the vessel wall. In one embodiment, each anchor 220 has a length of about 2 mm or less. The number of anchors 220 required by each particular anchoring member is such that the anchors can provide an optimal force distribution for the anchoring members. The length, projection, and angle of the anchors 220 are optimized so as to provide a sufficient anchoring force without requiring too much longitudinal motion to set the distal anchoring member (e.g., to cause the anchors to penetrate the vessel wall and, if desired, the adjacent anatomy). The width (and/or thickness) of the anchors 220 are optimized to reduce trauma to the vessel wall or tissue and yet still allowing sufficient anchoring force for the distal anchoring member. For most vessel applications (like in the coronary sinus or great cardiac vein) anchor widths (and/or thicknesses) from about 0.0002" to about 0.025" range are usable, but wider (and/or thicker) anchors may be required in larger vessels for other applications. As a practical matter, for most vessel applications, the width of an optimum anchor will be from about 0.008" to about 0.025" and its thickness will be from about 0.002" to about 0.012". In one embodiment, the anchoring member has a thickness greater at and/or near the anchors 220 and attachment spine 222 to provide support in the areas of the anchoring member that experience the greatest forces upon cinching. For instance, the anchoring member may be cut from a tube with an eccentric ID, such that the attachment spine 222 (or the attachment location) is cut from the greatest wall thickness.

In one embodiment, the unattached crowns 218 (unattached to a spine 216 or 222) or crowns 218 pointing in the direction of probable motion during cinching of anchoring member 214 may be configured to be larger or slightly larger in surface area and less pointed on their ends than the crowns of a conventional stent. The larger and less pointed design of crown 218 in FIG. 20 helps the distal anchoring member 214 to spread out the forces that are applied by the anchoring member 214 to the vessel wall or tissue. The larger and less pointed design of crown 218 thus also helps in minimizing trauma to the vessel or tissue when the anchor is set (during any longitudinal motion relative to the vessel in the direction that the crown points). Additionally, the design of crown 218 is such that has little influence on the expansion or compression characteristics of the anchoring member.

In one embodiment, the attachment spine 222 is configured similarly to the spine 216 except that the attachment spine 222 is slightly wider and/or thicker. In some embodiments, the anchor attachment section of the backbone structure can act as the attachment spine for the anchoring member 214, thus the attachment spine 222 on the anchoring member 214 can be eliminated or modified in design such that it is a link, a discontinuous spine and/or incorporates attachment points 224 directly into the ring 226 design. In one embodiment, the attachment spine 222 provides dimension stability to the distal anchoring member 214 and provides cinching force distribution to each ring 226 of the anchoring member 214.

The proximal anchoring members of the embodiments of the present invention are similar to the distal anchoring members previously discussed. In some embodiments, the proximal anchoring member is deployed in an ostium, a larger vessel and/or covers a larger area compared to where the distal anchoring member is deployed. Thus, the proximal anchoring member can be larger than the distal anchoring member (for example, as illustrated in FIG. 20 proximal anchoring member 240 is larger than distal anchoring member 238). Additionally, the proximal anchoring member may be deployed in a vessel or ostium that has more supporting adjacent anatomy. For instance, the vessel or ostium may not have a free wall. Due to these factors, in some embodiments, the proximal anchoring member is deployed in an area that does not require the anchors 220 to be present. For instance, the proximal anchoring member may be deployed at the entrance of a coronary sinus. The proximal anchoring member may include anchors located at different locations or fewer anchors (comparing to the distal anchoring member) depending on application. For instance, a proximal anchoring member placed in the ostium (entrance) of the coronary sinus may have anchors distributed around its proximal end, where they may engage supporting tissue at or near the interface of the right atrium and the coronary sinus. Additionally, in some embodiments, the proximal anchoring member has a tapered configuration similar to shown in FIG. 20 (proximal anchoring member 240). The tapered configuration of the proximal anchoring member allows the anchoring member to more easily conform to the rapidly changing ID's of some vascular structures, such as the ostium of the coronary sinus in the right atrium of the heart. Thus, the tapered configuration provides another stabilizing and anchoring capability for the proximal anchoring member.

FIG. 20 illustrates another exemplary device 230, which is similar to the device 100 and the device 170 previously discussed. The device 230 comprises a longitudinally adjustable member that is not a telescoping assembly. Instead, the device 230 comprises a flexural deflecting member. In one embodiment, the device 230 includes a distal anchoring member 238 and a proximal anchoring member 240 connected and spaced apart by a flexural deflecting tube 232. The flexural deflecting member 232 is a tube that is flexible, bendable, and compressible. In one embodiment, the flexural deflecting member 232 can be deflected on one side to cause a shape change in the flexural deflecting member 232. The material used to make the flexural tube 232 can be tailored to have different flexural characteristics at different sections or sides of the tube depending on the application. In one embodiment, the flexural deflecting member 232 includes a backbone composed of distal anchor attachment section 234, spring-supported section 233, and a proximal anchor attachment section 236. The spring-supported section 233 can be made of a material and/or design that can allow the section 233 compress on at least one side of the section 233.

Figure 24:
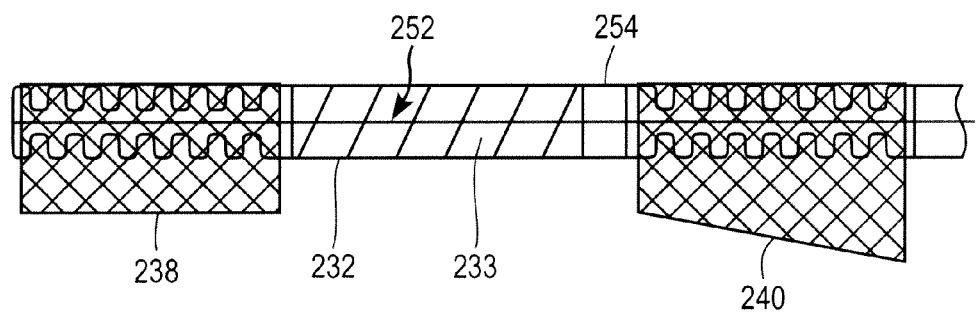
FIG. 24 illustrates yet another exemplary embodiment of a proximal anchoring member and a distal anchoring member connected by a flexural member with a locking mechanism immediately distal to the proximal anchoring member.

A cord 252 is disposed within the device 230 (FIGS. 20 and 21A-21C). In one embodiment, the cord 252's distal end is attached to a distal section of the device 230, e.g., to a proximal point of the distal anchor attachment section 234. The cord 252 is used to deflect, tighten, and/or shorten the flexural deflecting member 232. The cord 252 allows for adjusting, reshaping, or changing the curvature or radius of the flexural deflecting member 232. In one embodiment, the cord 252 is positioned within the device 230 so that when the cord 252 is pulled, the flexural deflecting member 232 preferentially compresses longitudinally on one side. In one embodiment, the cord 252 is positioned toward one side of the flexural deflecting member 232. In one embodiment, the flexural deflecting member 232 has a side S200 and S100, and a midline 256 (FIG. 21A). In the present embodiment, the cord 252 is confined to the side S200. The cord 252 may be disposed within a lumen 258 provided within the flexural deflecting member 232 on the side S200. In the present embodiment, when the cord 252 is pulled, the side S200 preferentially compresses, shortens, and/or bends relative to side S100, thus changing the shape, length, curvature, and/or radius of the flexural deflecting member 232. In one embodiment, the cord 252 is placed on the side of the flexural deflecting member 232 that compression or deflection is desired. A locking device 254 is coupled to the proximal end of the device 230 (FIG. 20, & 21A-21-C). In alternative embodiments, the cord locking device 254 is placed distal or immediately distal to the proximal anchoring member 24 or distal to the attachment section 236 (FIG. 24). The locking device 254 is configured to control the movement of the cord 252 and is configured to lock the cord 252 in place after adjustment to the flexural deflecting member 232 is completed. An example of a locking device 254 can be found in U.S. patent application Ser. No. 10/740,360 previously mentioned.

In one embodiment, the device 230 is deployed in a vessel that upon deployment the flexural deflecting member 232 compresses one side of the vessel and causes a shape change and/or a length change to the vessel or an adjacent feature. In one embodiment, the device 230 is deployed within a Coronary Sinus (CS) 248 as illustrated in FIGS. 21B and 21C. The device 230 is deployed in a way that limits (acute and chronic) distention of and damages to the free wall of the CS 248, as previously discussed. The proximal anchoring member 240 may be deployed at the entrance 250 of the CS 248. The distal anchoring member 238 is deployed in a location distal to the entrance 250. In the present embodiment, it is preferred that the distal anchoring member 238 and the proximal anchoring member 240 be longer than those included in the device 100 and 170 previously discussed, since more radial force may be required to flex or compress one side of the CS 248 and the anchoring members may be configured longer to distribute such force over the free wall of the coronary sinus or other vessel, as there is no telescoping action for them to interfere with.

Figure 22:
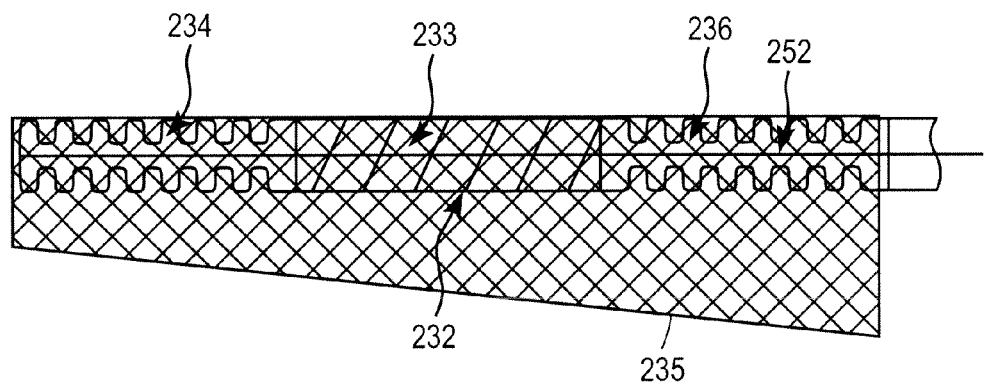
FIG. 22 illustrates another exemplary embodiment of one anchoring member supported by a flexural member.
Figure 23:
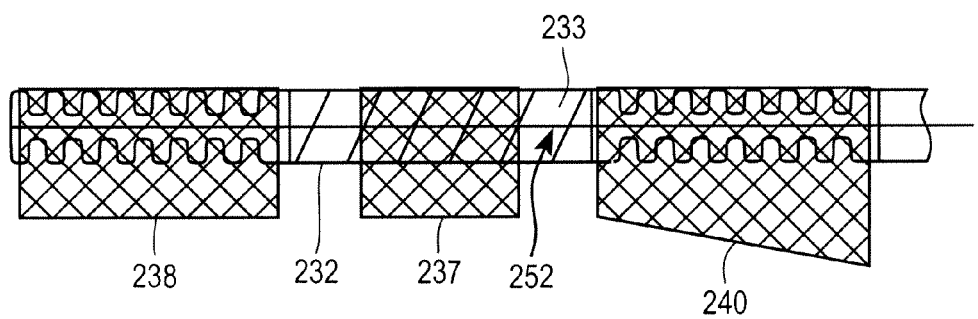
FIG. 23 illustrates another exemplary embodiment of a plurality of anchoring members connected by a flexural member.

In one embodiment, the proximal and distal anchoring members are joined as a single anchoring member 235 that is attached to the anchor attachment sections 234 and 236 (FIG. 22). In some other embodiments, one or more anchoring members 237, in addition to the distal and proximal anchoring members 238 and 240, are also attached to flexural deflecting member 232 and/or locking device 245 (for example, as shown in FIG. 23).

In one embodiment, the device 230 is deployed in the CS 248 in an orientation that has the cord 252 being placed more on the side that is away from the mitral Valve Annulus (MVA) 242 that is partially encircled by the CS 248. As shown in FIG. 21B, the cord 252 is placed away from the side of the CS 248 that is adjacent the MVA 242 (e.g., side S200). When the cord 252 is pulled (FIG. 21C), the flexural deflecting member 232 preferentially longitudinally compresses on the side (e.g., S200) and flattens the MVA 242, in effect, bringing together the leaflets 244 and 246 of the MV 248, and in turn, repairing MVR caused by excessive leaflet separation. In one embodiment, the lumen 258 keeps the cord 252 on the side away from the MVA. The flexural member will bend in the direction that cord 252 is on. To get the annulus to flatten, the flexural member bends away from the Mitral annulus with the assistance of the cord 252 being confined to the side of the flexural member that is away from the MVA. When the cord 252 is pulled, the flexural deflecting member 232 is being straightened or even being bent in curve opposite to the natural curve of the MVA 242 and CS 248 to press on a central region of the posterior portion of MVA 242 (adjacent to leaflet 246), flattening the MVA 242 in that portion, and bringing the leaflets 246 and 244 closer to each other. Additionally, the flexural deflecting member 232 may also be designed to experience a significant overall shortening (compression) in response to the cord forces required to effect the straightening (or reverse bending) of the flexural deflecting member 232. This shortening will also improve the bringing together of the leaflets 246 and 244 in much the same manner as cinching a device with telescoping members. The design of flexural deflecting members is well known in the art, although it is usually a design goal to minimize overall shortening, however; designing to control the overall shortening to larger values is a simple engineering extension of the current art.

In one embodiment, the distal anchoring member 238 and the proximal anchoring member 240 are configured to be longer (e.g., longer than 15 mm) than those anchoring members used in the device 100 or 170 previously discussed so that the distal anchoring member 238 and the proximal anchoring member 240 can distribute the forces on the flexural deflecting member 232 more evenly over the wall of the vessel. The forces on anchoring members 238 and 240 will have a radial force component (a force pushing against the vessel wall in a direction away from the MVA 242) much larger than with device 100 or 170. Additionally, the distal anchoring member 238 and the proximal anchoring member 240 are also configured so that they can resist rotational motion so that when the flexural deflecting member 232 deflects, bends and/or compresses due to the cord 252's pulling action, the distal anchoring member 238 and the proximal anchoring member 240 can resist rotation and keep the flexural deflecting member 232 against the side of the vessel toward the MVA 242 to more effectively compress and flatten the MVA 242.

In one embodiment, the distal anchoring member 238 and the proximal anchoring member 240 are delivered so that the attachment points of the distal anchoring member 238 and the proximal anchoring member 240 to the respective anchor attachment sections 234 and 236 are located, situated, or oriented toward the side of the CS 248 that faces the MVA 242 and not the vessel's free wall side (FIG. 21C) to prevent unnecessary damage to the vessel's free wall. In embodiments analogous to FIGS. 12B and 12D, where the anchor attachment sections 234 and/or 236 are omitted and the anchors 238 and/or 240 are contiguous with the backbone of device 230, the preferred orientation is such that the portions analogous to connecting members 2108 and 2208 are orientated toward the side of the CS 248 that faces the MVA 242 and not the vessel's free wall side.

Figure 25A:
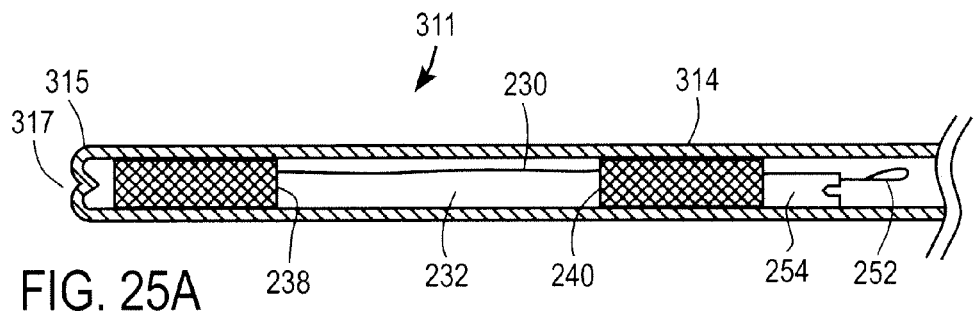

FIG. 25A illustrates an exemplary delivery device that can be configured to house one of the devices of the present invention and deliver the device to a vessel or location. For instance, the exemplary delivery device can be used to house and deliver the device 100, 170, or 230 previously discussed. The delivery device can be delivered percutaneously using methods or apparatuses described in U.S. patent application Ser. No. 11/008,902 incorporated herein.

FIG. 25A illustrates an assembly 311 that includes a device catheter 314 which can house one of the devices previously described (e.g., device 230, 100, or 170) and which can be used to deliver the device to a treatment site, (e.g., a vessel or a coronary sinus). The discussion related to FIGS. 25-29 refers to the device 230. However, it is to be understood the discussion applies similarly to other devices of the embodiments of the present invention. The device catheter 314 is shown in a partial sectional view in this figure. The device catheter 314 is made out of a polymeric material(s) or other suitable material to give the device catheter 314 flexibility. The device catheter 314 has a thin wall. In this figure, the distal anchoring member 238 and the proximal anchoring member 240 are compressed or collapsed within the device catheter 314. In one embodiment, the device catheter 314 constricts or compresses the anchoring members 238 and 240 prior to and during delivery into the anatomy. When the device catheter 314 is retracted/withdrawn, (e.g., retracted proximally) the anchoring members can be deployed (similar to how self-expanding stents are deployed). The device catheter 314 can be the delivery sheath or the delivery catheter previously mentioned. In other embodiments, another catheter or portion of a catheter, whose distal end butts up against the proximal side of a stop or other feature of the distal portion of a device, such as devices 100 and 170, may be included inside device catheter 314 to hold the device at or near it longest length (or at a length greater than its shortest cinched length) during device insertion and positioning in the anatomy and during deployment of the distal anchoring member, as previously described. In some embodiments, device catheter 314 and other catheters may have OD's/ID's that are larger in their distal portions relative to their proximal portions.

Figures 1, 2, 25B, 25C:
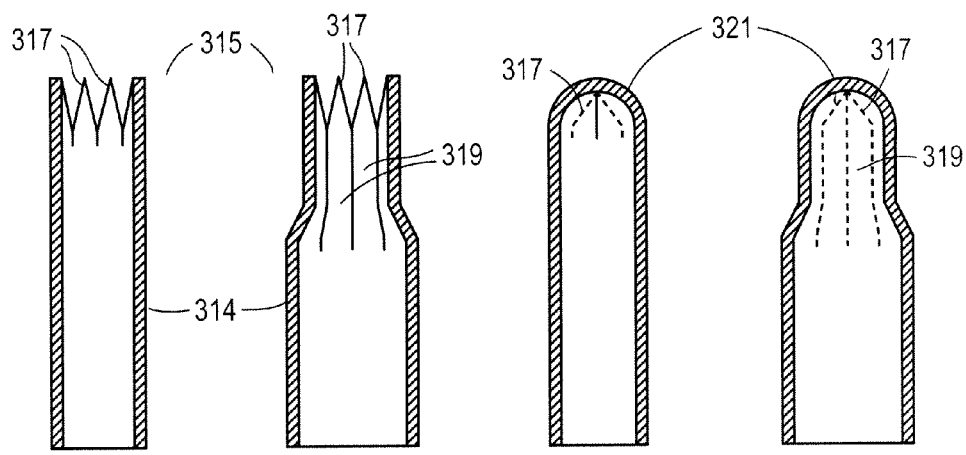

The distal end 315 of the catheter 314 can be configured so that it can temporarily form a blunt or rounded atraumatic distal tip 321 and it can open to allow retraction of the catheter 314. In one embodiment, a distal end 315 of the device catheter 314 has one or more tip section 317, which may have a triangular-like shape (may have two curved sides) end and is cut into the distal end of catheter 314 (FIG. 25B-1). The sections 317 may be cut to create tab-like configurations or sleeve-like sections 319 (FIG. 25B-2). Sections 317 can then be bent over using a forming die and/or a forming mandrel (or other devices/components) to heat set and/or partially re-melted them (and sleeve-like sections 319, if present) to form a blunt/rounded atraumatic distal tip 321 on the device catheter 314 (FIG. 25C-1 or 25C-2). In one embodiment, when the device catheter 314 is withdrawn, the tip sections 317 are bent back and the sleeve-like sections 319, if included, break apart as they pass over the device 230. Since the device catheter 314 is a relatively thin walled polymeric tube, the force required to bend the tip sections 317 or to separate the sleeve-like sections 319 is low.

Figure 26:
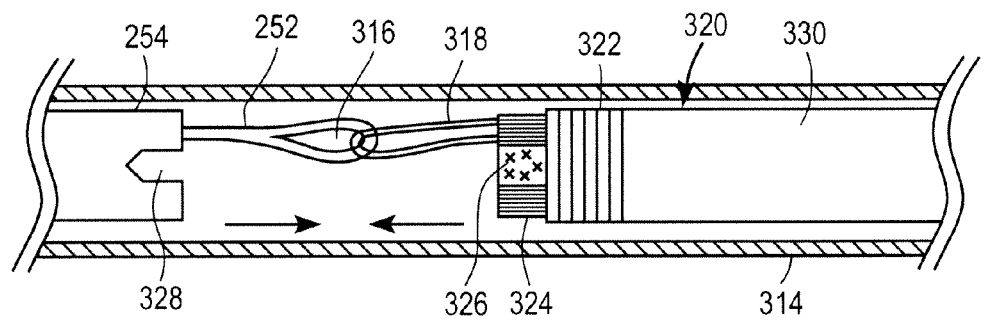

The assembly 311 further includes an inner member 320, which couples or mates to a locking device 254 (FIG. 26). The device catheter 314 houses the inner member 320. The device catheter 314 acts as an outer member for the delivery device. The mating of the inner member 320 and the locking device 254 enables the device 230 (or the proximal portion of device 100 or 170) to be held in position or constrained in its movement during device deployment and during cord 252 tightening and locking. In one embodiment, the inner member includes an inner member shaft 330, an inner member lumens 332 and 334 (shown in FIG. 28A), an inner member engage section 322, an inner member mating section 324, and one or more alignment projections 326 (FIG. 26). The inner member engage section 322 engages the proximal end of the locking device 254 with the inner member mating section 324 mating within the locking device 254. The alignment projection or projections 326 are aligned and mated into respective alignment slot or slots 328 provided on the proximal end of the locking device 254 and/or the proximal end of the device 230 (or the proximal end of device 100 or 170).

In one embodiment, the proximal end of the locking device 254 and/or the proximal end of the device 230 (or the proximal end of device 100 or 170) has a tubular configuration having a lumen (not shown) with the alignment slot 328 created in it (shown in a side view in FIG. 26). The distal end of the inner member shaft 330 has the inner member engagement sections 322 and the inner member mating section 324.

Figure 27:
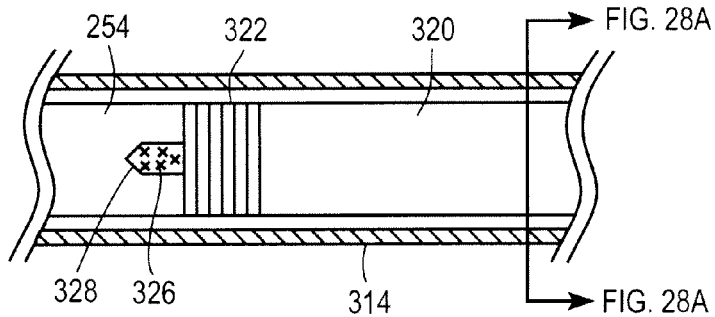

The inner member mating section 324 engages (e.g., slip fits into) the inner space (or inner diameter) of the proximal end of the locking device 254 and/or the proximal end of the device 230. In one embodiment, the inner member engagement section 322 is of a sufficient thickness that when the mating section 324 is advanced into the inner space of the locking device 254, the inner member engagement section 322 butts up against the end of the locking device 254 as illustrated in FIG. 27. Thus, the proximal end of the locking device 254 and/or the proximal end of the device 230 is constrained from proximal movement when the inner member 320 engages the locking device 254. In one embodiment, the inner member engagement section 322 includes one or more of the alignment projections 326 that engage the respective alignment slots 328 as shown in FIG. 27. Such engagement controls the relative rotational orientation of the distal end of the inner member 320 and the locking device 254 and/or the proximal end of the device 230.

Additionally, the mating of the inner member 320 and the locking device 254 and/or the proximal end of the device 230 further provides an alignment of the rotational orientations of the device 230 and the inner member 320. Such alignment also allows the cord 252 and cord loop 316 of the device 230 to align with the inner member lumen 332 of the inner member shaft 330 and a path for an actuator provided to control the locking and/or unlocking of the cord to align with a lock's actuating mechanism.

Figures 28A, 28B:
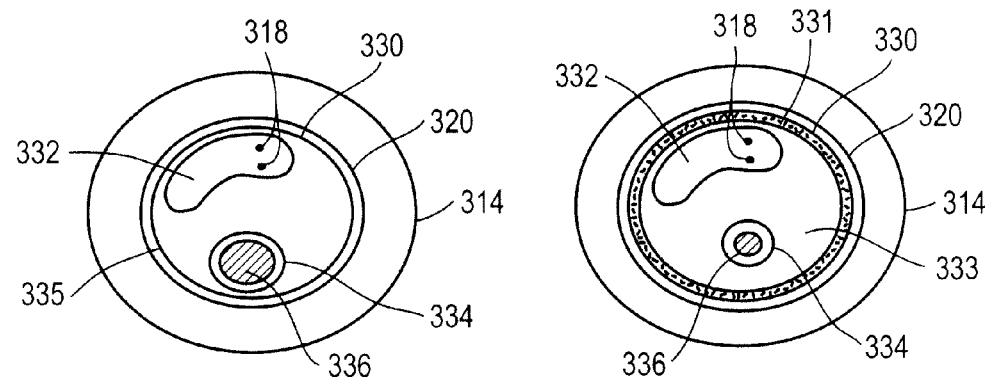

FIG. 28A illustrates a sectional view of the device catheter 314 and the inner member 320 taken through the inner member shaft 330 as shown in FIG. 27. The inner member 320 resides in the inner diameter of the device catheter 314. The inner member 320 can be configured to house an actuator member 336 that is used to control the locking and/or unlocking of the cord 252. The inner member 320 can also be configured to house the cord 252 or a cord pull-loop 318 releasably connected to the cord 252 in lumen 332.

In one embodiment, the actuator member 336 is positioned within a lumen 334 provided in the inner member shaft 330 (FIG. 28A). The actuator member 336 functions to unlock and/or lock the cord 252 in the device 230, which allows for the cord 252 adjustment of device 230 to be retained (locked) and/or released (unlocked). For instance, once the device 230 has been deployed in the vessel and the cord has been pulled relative to the locking device 254 to adjust the bending and/or length of the device 230 as desired, the actuator member 336 is advanced distally into the locking member 254, the cord 252 is locked and the adjustment to device 230 is fixed. In one embodiment, the lumen 334 in the inner member shaft 330 contains a lubricious lining (not labeled) (for example, PTFE, FEP, microglide® coating) to provide a low friction lumen for the actuator member 336. In some embodiments, the OD of the actuator member 336 may incorporate a similar lining.

It is preferred that the inner member shaft 330 be constructed in a manner such that its compression is minimized (high compression modulus) and its resistance to torsion be low (low torsion modulus). For example, in one embodiment, the inner member shaft 330 preferably includes a well-designed spring, braid, or backbone supporting member 331 and a filler material 333 forms the desired cross-section of the inner member shaft as shown in FIG. 28B. The supporting member 331 helps minimizing the compression of the inner member shaft 330 when device catheter 314 is withdrawn during device 230 deployment and when the cord 252 is pulled (via the cord loop 316) during adjustment of the device 230. In another embodiment, the supporting member 331 is formed from a spring, a metallic tube, a braided tube or other well-designed structure that functions as a supporting member and minimizes the compression of the inner member shaft 330, while providing a relatively low torsion modulus to inner member shaft 330. Filler material 333 is preferred to be a polymer or polymer blend that may impregnate or be present in the ID and on the OD of any supporting member 331 and/or help form or support a lumen such as lumen 332 or 334.

In one embodiment, the inner member shaft 330 includes a lumen 332, which may be formed in the filler material 333 and comprise the support member 331 as above for the shaft 330. The proximal portions of cord 252 (includes cord loop 316) and the cord pull loop 318 are contained within and longitudinally slideable within the lumen 332. The cord pull loop 318 is illustrated as two dots since there are two ends to the pull loop 318, and the two ends are visible from this cross-sectional view. Note that in the cross-sectional view shown in FIGS. 28A and 28B, the cord 252 is not visible and only the pull loop 318 is visible since the cord 252 (and cord loop 316) resides distally in the lumen 332 of inner member shaft 330.

In one embodiment, the inner member shaft 330 and the device catheter 314 have a relatively low torsion modulus to facilitate the alignment of preset curves that are incorporated in or near the distal end of the assembly 311 and/or device 230 with the curves of the anatomy. In certain applications, such preset curves are configured to accommodate the curves of the anatomy that the assembly 311 will travel through. In addition, such preset curves, when aligned with the curves of the anatomy during device 230 deployment, provide for device 230 to be deployed in the vessel in the desired orientation relative to the vessel and/or adjacent anatomy. Such an alignment of curves will occur naturally, because the lowest energy state of the curved portions of the device 230, inner member shaft 330 and/or the device catheter 314 is when those curves align with the curves of the vessel/anatomy that they are constrained by and thus, those curves experience the least change in their curvature.

Figure 29:
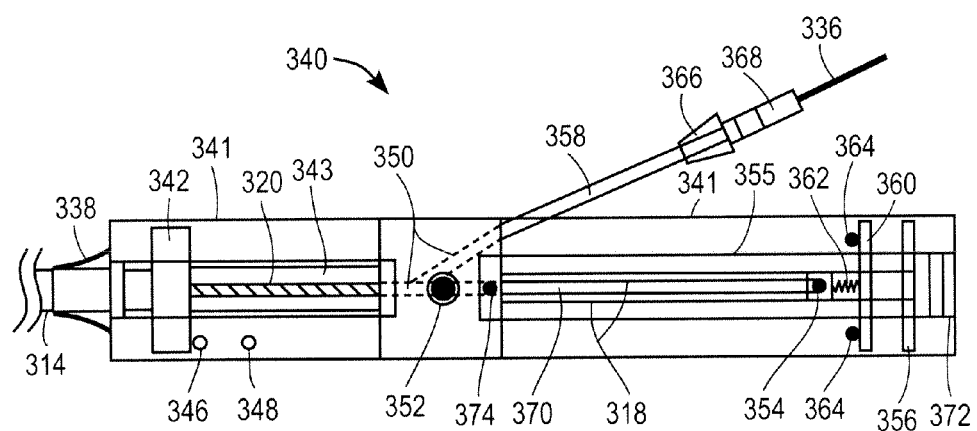
FIG. 29 illustrates an exemplary embodiment of a proximal handle that can be used with a device of the present invention such as the device shown in previous FIGS. 25-28.

FIG. 29 illustrates an exemplary embodiment of a novel proximal adapter or handle that can be used to deliver and control any one of the devices previously described especially devices that have deployment. The assembly 311 is but one example of such a device that can benefit from the proximal adapter described herein. The proximal adapter is configured to move the device catheter 314 relative to the inner member 320 in order to deploy the device 230 carried by the assembly 311. In this figure, a proximal adapter 340 is illustrated. In one embodiment, the proximal adapter (or handle 340) is attached to or cooperates with the device catheter 314, the actuator member 336, cord pull loop 318 and the inner member 320 therein. In one embodiment, the proximal portions or ends of device catheter 314 and inner member 320 are coupled to a portion of handle 340 and a portion of the device catheter 314 is covered by a strain relief member 338. Since the handle 340 is a relatively rigid structure and the proximal portions of the delivery system (device catheter 314, inner member 320, cord pull loop 318, and actuator 336) is a relatively flexible structure, the strain relief member 338 is provided as a transition length. The strain relief member 388 provides a transitional flexural length for this portion of the delivery system where it enters the handle 340 to help prevent kinking of the delivery system components at the distal end of handle 340. In one embodiment, the strain relief member 338 is attached to the handle 340 and has an inner diameter that is sized to allow the device catheter 314 to be slidably close fitted thereto.

The handle 340 includes a handle body 341. The handle body 341 is configured to house a plurality of components of the handle 340. The handle body 341 houses and longitudinally fixes a proximal portion and/or end of inner member 320 (previously described) relative to itself, houses an anchor control 342 to control the device catheter 314, an internal lumen 350 for the actuator member 336 to travel through and allow inner member 320 lumens to be flushed, and a cord control mechanism 355 to control the cord 252 coupled thereto via cord loop 316 and cord pull loop 318.

The proximal portion of the inner member 320 is coupled to a portion (a distal portion) of the handle 340. In one embodiment, the proximal portion of the inner member 320 is placed in an inner space (inner diameter) 343 of the handle body 341 and its proximal end is sealed to communicate with internal lumen 350. The internal lumen 350 provides a path for the actuator member 336 from outside of the handle 340 into the handle body 341, through the inner member 320, and into the locking member 254 of device 230 (e.g., locking member 254 of the device 230, not shown here, but see FIGS. 25A and 26). There is thus a path that runs from outside the handle 340, through the handle 340 and is communicable with assembly 311 so that the actuator member 336 can effectuate locking and unlocking of the locking member 254 of the device 230. Details of locking and unlocking using an actuator member can be found in the U.S. patent application Ser. No. 10/740,360 incorporated herein.

The anchor control 342 is longitudinally slidably contained within the handle body 341. In one embodiment, the anchor control 342 is constrained within inner space 343 of handle body 341. The anchor control 342 is configured to engage the proximal end of device catheter 314 such that moving the anchor control 342 proximally can cause the device catheter 314 to retract (move proximally) relative to the inner member 320. The anchor control 342 functions to cause the device catheter 314 to retract relative to the inner member 320. In one embodiment, the anchor control 342 attaches to a proximal portion of the device catheter 314 so that moving the anchor control 342 also moves the device catheter 314. When the device catheter 314 is retracted, e.g., proximally, relative to the inner member 320, the distal anchoring member 238 and then the proximal anchoring member 240 of the device 230 are deployed. In one embodiment, the anchor control 342 is configured so that when it is moved proximally relative to the body 341, the device catheter 314 is also moved proximally relative to the inner member 320. The distal anchoring member 238 and the proximal anchoring member 240 can then be deployed. In another embodiment, a single anchoring member may be deployed (see FIG. 22). In another embodiment, more than two anchoring members may be deployed (see FIG. 23). In other embodiments, where a sheath or other device, as previously described, is included inside device catheter 314 and outside or inside inner member 320, a second anchor control for it may be included in handle 340 proximal of anchor control 342.

The handle 340 is configured to control or constrain the movement of the anchor control 342. In one embodiment, a plurality of lock members or pins is provided to constrain the anchor control 342's movement. In one embodiment, one or more first lock pins 346 are placed in the handle body 341 to constrain the anchor control 342 until deployment is desired. The first pins 346 control the deployment for the distal anchoring member 238. In one embodiment, the first pins 346 constrains the anchor control 342 from longitudinal movement relative to the handle body 341. When the first pins 346 is removed, anchor control 342 may be moved proximally relative to the handle body 341 until its proximal motion is constrained by second lock pins 348. In one embodiment, this proximal movement is sufficient to cause the device catheter 314 to move proximally relative to the inner member 320 enough to deploy distal anchor 238. One or more second lock pins 348 are also included in the handle body 341 to constrain the anchor control 342. The second lock pins 348 are placed proximally to the lock pins 346. The second lock pins 348 control the deployment for the proximal anchoring member 240. When the second lock pins 348 is removed, anchor control 342 may be moved proximally relative to the handle body 341 until its proximal motion is constrained by the handle body 341 construction (for example, termination of inner space 343). In one embodiment, this second proximal movement is sufficient to cause the device catheter 314 to move proximally relative to the inner member 330 enough to deploy proximal anchor 240. In one embodiment, the handle body 341 includes openings (not shown) and/or the pins 346 and 348 are constructed so that the pins 346 and 348 can be removed from the handle body 341 when desired. The construction of removable pins and their associated holes (for example, ring grip quick release self-locking pins) are well known in the art. Thus, when the pins 346 is removed from the body 341, the anchor control 342 may be retracted proximally causing the device catheter 314 to retract proximally and the distal anchoring member 238 deployed. The pins 348 prevent the anchor control 342 from being retracted further until it is desired to deploy the proximal anchoring member 240. When ready, the pins 348 are removed from the body 341 allowing the anchor control 342 to be retracted further, the device catheter 314 to retract further proximally, and thus, causing the proximal anchoring member 240 to deploy. There are many mechanisms that can be used instead of the pins to control a longitudinal movement of a member disposed in a handle body, e.g., latches or screws, detented sliders or rotation knobs.

The attachment of the inner member 320 to the handle body 341 is such that the lumens of the inner member 320 communicate with the internal lumens 350 housed by the handle body 341. For instance, the lumen 332 communicates with a connector (e.g., a Luer) 352 via the internal lumen 350 and provides a way for flushing of the lumen 332 and/or lumen 334 when necessary, such as prior to assembly 311 insertion into the body/anatomy.

In one embodiment, the pull-loop 318 exits the internal lumen 350 proximally via a seal or seals (not shown) so that the flush flow out of lumen 350 around the pull loop 318 is minimized or limited. The pull-loop 318 engages a post 354 of the cord control 356. Thus, moving the cord control 356 proximally causes the pull-loop 318 to be pulled proximally. In one embodiment, the proximal ends of pull-loop 318 are constrained by post 354. In one embodiment, the proximal ends of pull-loop 318 are joined together and constrained by post 354.

In one embodiment, the cord 252 provided in the device 230 is controlled via a cord control mechanism 355 provided in the proximal handle 340. The cord 252 has at its proximal end a cord loop 316 and the cord pull-loop 318 engages the loop 316 to allow for the pull-loop 318 to pull on the cord 252 and to release from the cord 252 once adjustment and locking are achieved as previously described. The handle 340 houses the cord control mechanism 355 that includes a cord control 356 which is configured to allow for control of the cord pull-loop 318, and hence, the cord 252. The cord control 356 is longitudinally slidably contained within the handle body 341. In one embodiment, the cord control mechanism 355 is placed proximal to the anchor control 342 and proximal to the device catheter 314. In one embodiment, the cord control 356 works cooperatively with a tension handle 360, which is longitudinally slidably contained within the handle body 341. The cord control 356 is attached to a spring 362. The other end of the spring 362 is connected to tension handle 360. The cord control mechanism 355 further includes a tension lock pin or pins 364 provided on the handle body 341. The pins 364 engage the tension control handle 360 in a manner that extends the spring 362, which in turn applies a tensioning force on the cord pull-loop 318 via cord control 356 and post 354. In one embodiment, this tension helps keep the device 230 and the inner member 320 engaged during shipping, prior to delivery into a vessel, and/or prior to adjustment of the device 230. In one embodiment, where a device similar to device 230 is to be delivered in a deflected and/or compressed state, the sliding assembly, consisting of the cord control 356, the tension handle 360, the spring 362 and the post 354, is held in a proximal position on the handle 340 by the engagement of the pins 364 with the tension handle 360 such that the required deflection and/or compression tension is placed on the pull-loop 318, as shown in FIG. 29. In one embodiment, where a device similar to device 230 is to be delivered in a deflected and/or compressed state, the sliding assembly, consisting of the cord control 356, the tension handle 360, the spring 362 and the post 354, is held in a proximal position on the handle 340 by the engagement of the pins 364 with the tension handle 360 such that the required deflection and/or compression tension is placed on the pull-loop 318 when the locking device 254 is transitioned to the unlock position and cord 252's longitudinal motion is unconstrained, as shown in FIG. 29. Alternately, the pins 364 may engage the cord control 356 such that the required deflection cord translation is placed on the pull-loop 318 and the spring 362 and the tension handle 360 may be omitted. In one embodiment, where a device similar to device 230 is to be delivered in a deflected and/or compressed state and no adjustment of the device 230 is required after locking device 254 is unlocked, the cord control mechanism 355 may be eliminated from handle 340. In another embodiment, where the device 230 is replaced with a device similar to device 100 or 170 and the chosen delivery method is to begin the deliver of the device with its telescopes fully or substantially engaged, the sliding assembly is held in a proximal position on handle 340 by the engagement of the pins 364 with the tension handle 360 such that a small tension is placed on the pull-loop 318. In other embodiments, with a device similar to device 230 is to be initially delivered in a relatively unflexed/uncompressed state or with a device similar to the device 100 or 170 and the chosen delivery method is to begin the deliver of the device with its telescopes disengaged or substantially disengaged, the sliding assembly is initially held in a more distal position on the handle 340 by the pins 364 than shown in FIG. 29 and with the pull-loop under a small tension. In the preferred embodiments, prior to device deployment, the sliding assembly is positioned distally on the handle 340, the device 230 (or devices similar to the devices 100 and 170) is in a fully or substantially undeflected, uncompressed (longitudinally) and/or uncinched state and the pull-loop 318 is under a small tensile force. In the preferred embodiments with devices similar to the devices 100 and 170, prior to device deployment, the sliding assembly is positioned distally on the handle 340, the device 100 or 170 is in a fully or substantially uncinched state, the pull-loop 318 is under a small tensile force and the distal portion of device 100 or 170 is held in position by a sheath or other device, as previously described. It is preferred that the longitudinal translation distance of the sliding assembly allowed by the cord control mechanism 355 of the handle 340 be equal to or greater than the pull distance required by the pull-loop 318 to cause the device 230 (or the device 100 or 170) to fully transition the device over its full range of cord adjustment.

There are many mechanisms known in the art that allow a longitudinally sliding member's position to be easily locked and unlocked. For instance, a thumbscrew could be screwed into the cord control 356 through a slot on cover 370 provided on the handle body 341. When the thumbscrew is tightened, the thumbscrew pinches the cover between the cord control 356 and itself and the position of the cord control 356 is locked; when the thumbscrew is loosened, the cord control 356 may be translated longitudinally. Alternately, the thumbscrew or other locking/unlocking mechanism may engage tension handle 360 and operate in a similar manner to lock and unlock the tension applied to pull-loop 318.

In an undeployed state/prior to device 230 deployment, the cord control 356 is preferably positioned distally on the handle 340. In one embodiment, in the undeployed state, the anchoring members 238 and 240 are not deployed or one of the anchoring members 238 or 240 are not deployed. In preferred embodiments, when the cord control 356 is in a more proximal position, the device 230 is in the delivered state, the anchoring members 238 and 240 have been deployed at desired location and the connecting member (or telescopes) is deflected, shortened and/or cinched, or the cord 252 within the device 230 (or within devices similar to devices 100 and 170) is at the shortest length to effectuate the desired deflecting, shortening, compressing, or cinching of the device 230 (or devices similar to devices 100 and 170).

The handle body 341 or cover 370 may contain marks/numerals/indicators relative to the cord control 256 that indicate the longitudinal translation applied to the cord pull-loop 318. Alternatively or in addition, the sliding assembly, consisting of a cord control 356, a tension handle 360, a spring 362 and a post 354, may include marks/numerals/indicators that indicate the tensile force applied to the cord pull-loop 318 by the translation of the tension handle 360. For instance, in FIG. 29, marks/numerals to indicate the cord pull-loop 318 tensile force may be placed on the cord control 356 and indicated by the position of the tension handle 360 relative to the cord control 356. Alternately or in addition, the design of the sliding assembly constrains the motion of the tension handle 360 such that the tensile force applied to the cord pull-loop 318 is limited to a desired maximum. For instance, in FIG. 29, the tension handle 360 may only translate proximally until it butts up against the cord control 356. Thus, during cord pulling, if the operator were to only translate the tension handle 360 close to, but not against the cord control 356, then the tensile force applied to the cord pull-loop 318 would not exceed a maximum value controlled by the extension of the spring 362. Controlling the tensile forces applied to the cord pull-loop 318 controls the cinching force applied during cinching devices similar to the devices 100 and 170. Controlling the applied cinching forces during device adjustment is desirable to prevent applying cinching forces capable of dislodging or translating a distal and/or proximal anchor deployed in a vessel. Such dislodging or translating of a distal and/or proximal anchor may cause undesirable vessel damage and failure of the device to achieve the desired amount of shortening. There are many mechanisms/devices know in the art that control and indicate forces and position that may be substituted for or made a part of the cord control mechanism 355 and/or the handle 340.

In one preferred embodiment, the locking device 254 is actuated, via the actuator member 336 to lock the cord 252 relative to the locking device 254 once the cord 252 has been adjusted as desired. Once deployment and adjustment, if any, of the device 230 (and its components) is achieved, its connection portions to the handle 340 are released from the device 230 and the device catheter 314 and the inner member 320, which are coupled to the handle 340, are withdrawn from the body. To release the device 230, prior to withdrawal, the cord pull-loop 318 can be pulled on one of its proximal ends (after release from post 354) to disengage it from the cord loop 316 of the cord 252, once the cord 252 is locked (or unlocked) in place. In one embodiment, the handle body 340 includes a cover 370, which can be opened by an operator to cut or release the pull-loop 318. The cord pull-loop 318 can be cut or the cord pull-loop 318 released from post 354 (by opening the cover 370 to access the pull-loop 318) and one side of the pull-loop 318 pulled, until the pull-loop 318 is free of the cord loop 316. In one embodiment, the cover 370 is coupled onto the handle body 341 at one end by a rotating member (e.g., a hinge) 372 such that the rotating the member 372 allows the cover 370 to be lifted from over the cord pull loop 318, once the locking pin 374 is removed. The locking pin 374 couples the other end of the cover 370 to the handle body 341 and prevents the cover 370 from inadvertently opening until it is removed. In other embodiments, the locking pin 374 and/or the rotating member 372 are replaced with other latch, release and/or access mechanisms known in the art.

In one embodiment, the actuator member 336 is longitudinally constrained by the handle 340. In one embodiment, the actuator member 336 accesses lumens 350 via an extension tube 358 connected to the proximal handle 340. In the present embodiment, the actuator member 336 is disposed within the extension tube 358 and through the internal lumen 350 and into lumen 334 of inner member 320. The actuator member 336 can enter and/or engage the locking device 254 via the lumen 334 as previously described (FIG. 28). Moving the actuator member 336 (longitudinally advancing distally or proximally) causes unlocking or locking of the cord 252 as discussed in U.S. patent application Ser. No. 10/740,360. Until deployment, the actuator member 336 is locked in place so that the locking device 254 will not be actuated (thus, not locking or unlocking cord 252) during shipping or prior to the device delivery and the desired adjustment of the cord 252. The extension tube 358 includes an attachment device 366. In one embodiment, attachment device 366 contains a seal or seal mechanism (for example, an o-ring, a diaphragm or a Touhy-Borst mechanism) that seals around actuator mechanism 336 to prevent or minimize leakage when the inner member 320 is flushed via lumens 350, as previously described. In one embodiment, the attachment device 366 can accommodate a pusher 368 that provides a convenient access to the actuator member 336. In one embodiment, the distal end of the pusher 368 is releasably engaged to the proximal end of the attachment device 366 similar to a Luer locking mechanism or thread mating mechanism. In many instances, the actuator member 336 is a small rod, tube or wire. Thus, having the pusher 368 provides a handle for an operator to hold and move the actuator member 336. The actuator member 336 may be releasably engaged to the pusher 368 which may be accomplished by a construction similar to that of a conventional guidewire torquing device. When the actuator member 336 is engaged to the pusher 368 and the pusher 368 is engaged with the attachment device 366, the position of the distal end of the actuator member 336 within the lumen 334 (FIG. 28) is fixed. Fixing this position, such that the distal end of the actuator member 336 will not actuate the locking member 254 during shipping and initial device use, prevents accidental locking (or unlocking) of the cord. The actuator member 336 is moved, in one embodiment, via the pusher 368 when it is desired to actuate the locking components in the locking member 254 as previously discussed. In one embodiment, to accomplish actuation of the locking member 254, the pusher 368 is disengaged from the actuator member 336 and the attachment device 366, the pusher 368 is moved proximally over a length of the actuator member 336, the pusher 368 is re-engaged with the actuator member 336 and then the pusher 368 is moved distally. In another embodiment, to accomplish actuation of the locking member 254, the pusher 368 is disengaged from the attachment device 366 and the pusher 368 is moved proximally. In other embodiments, to actuate the locking member 254, the pusher 368 is disengaged from the actuator member 336 and the actuator member 336 moved distally or proximally. After the actuation of the locking member 254 is accomplished, the actuator member 336 is fixed back into a position such that its distal end is locked back within the lumen 334, proximal of the distal end of lumen 334 or removed entirely from handle 340. In some embodiments, the actuator member 336 must be disengaged (such as by rotation) from locking member 254 prior to fixing it safely into a more proximal position or removing it, as is described previously in U.S. patent application Ser. No. 10/740,360. This prevents any accidental actuations of the locking member 254 during the later disengagement of cord loop 318 on cord 252 from the pull-loop 318 (previously described) and prevents accidental engagement of the distal end of the actuator member 336 with the anatomy, causing undesired tissue damage, during the subsequent withdrawal of the device catheter 314 and the inner member 320 from the anatomy. Many mechanisms to control the longitudinal position of a component like actuator member 336 within a lumen from a proximal location are know to the art and may be used instead of the previously described mechanisms. Such mechanisms may be permanently connected to actuator member 336 and handle 340.

Many variations of the handle 340 are possible. All that is required is that the handle can control the retraction of the device catheter 314 over the inner member 320, can control the movement and/or tension applied to the cord 252, has provision to allow the release of device 230 (or 100 or 170) and can control the movement of the actuator member 336. Additionally, in some preferred embodiments, a control for the retraction of a sheath or other device (previously described) used to keep the telescopes of a device similar to 100 or 170 substantially disengaged during at least a portion of device 100 or 170 delivery and/or deployment into the anatomy is required. In some less preferred embodiments (previously described), all that is required is that the handle can control the retraction of the device catheter 314 over the inner member 320, has provision to allow the release of device 230 and can control the movement of the actuator member 336.

Figure 30:
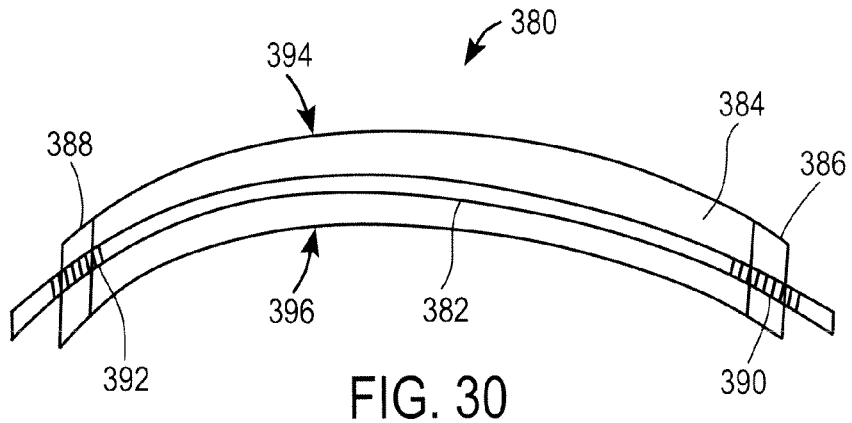
Figures 1, 31A:
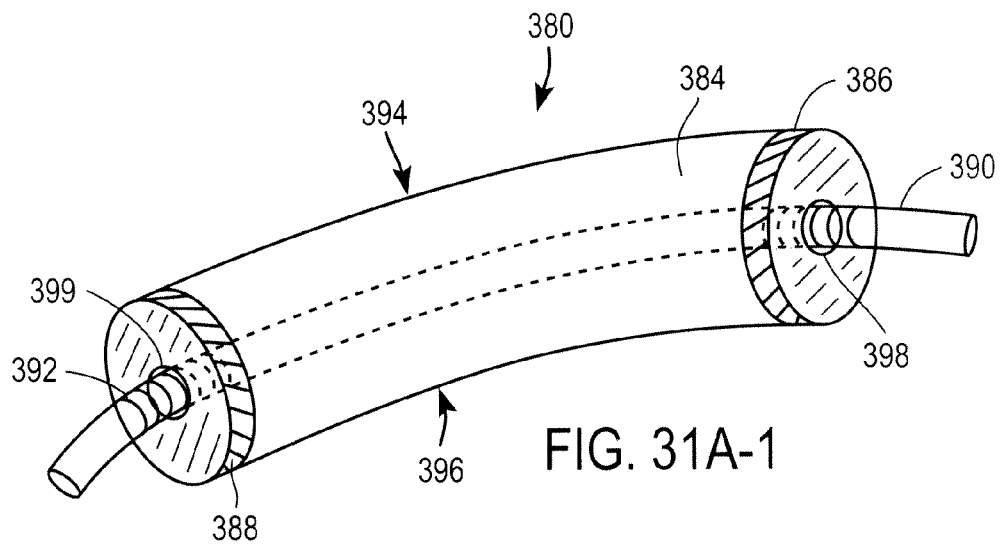
Figures 2, 31A:
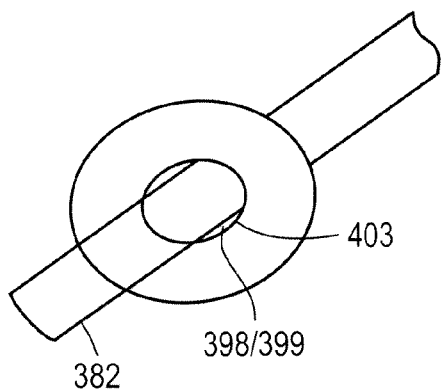
Figures 3, 31A:
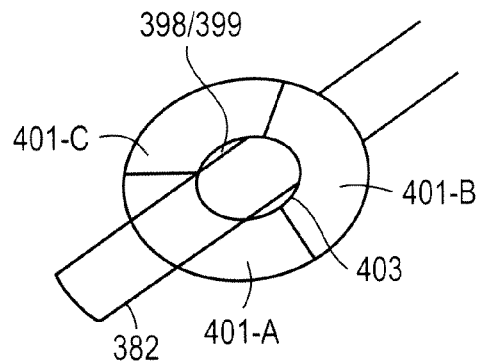

FIGS. 30 and 31A-1 illustrate an exemplary embodiment of a device 380 that can be used to reshape a vessel, deploy a vessel, deploy in a vessel, deploy across more than one vessels, deploy at a target location, etc., similar to previously described. For instance the device 380 can be used to change a radius of a curved vessel. In another instance, the device 380 can be deployed in a coronary sinus that is adjacent a mitral valve. After deployment, the device 380 can reshape or change the radius of the mitral valve annulus similar to devices previously described. It will be understood that the device 380 can be deployed in other vessel location for other treatment purposes. The device 380 utilizes a turnbuckle concept to adjust the length and/or curve/shape of the device 380 to effectuate similar changes upon the vessel or an adjacent vessel or tissue. The device 380 is thus longitudinally adjustable and also curve adjustable.

The device 380 includes a turnbuckle member 382 disposed within a device body or shaft 384, which includes therein a distal spacer 388 and a proximal spacer 386. The device shaft 384 can be analogous to the flexural tube previously described. The device shaft 384 includes at least one longitudinal lumen extending the entire length of the shaft 384 for the turnbuckle member 382 to be disposed therethrough. More lumens may be provided so that the fully deployed device 380 does not distract the flow of the fluid through the vessel that has the device 380 deployed therein. The turnbuckle member 382, the proximal spacer 386, and the distal spacer 388 work cooperatively as a turnbuckle assembly to control the length and shape of the device body/shaft 384. The turnbuckle member 382 includes a distal threaded section 392 and a proximal threaded section 390. The threaded section 392 allows the turnbuckle member 382 to be controllably turned within the distal spacer 388 and the threaded section 390 allows the turnbuckle member 382 to be controllably turned within the proximal spacer 386.

The device shaft 384 includes sides of different flexibilities (similar to the flexural member described above) such that adjustment can be made in a way to reshape the radius, curvature, and/or length of the device shaft 384. The device shaft 384 includes a side 394, which may be the side that needs to maintain a relatively fixed length, shape, curvature or radius. The side 394 may be configured to resist compression. The device shaft 384 also includes a side 396, which may be the side that allows length change, shape change, or radius change by being made more flexible, compressible, and bendable than the side 394. Thus, when the turnbuckle member 382 is turned, the length of the member 382 changes (e.g., shortens), the side 396 being more flexible, bendable, or compressible is adjusted (e.g., compressed). In one embodiment, when the device shaft 384 is changed in length and because of the difference in flexibility in the sides of the shaft 384, the curvature or radius of the shaft 384 is accordingly changed due to the movement of the turnbuckle member 382. The radius of the vessel having the device 380 changes accordingly. FIG. 31A-1 illustrates a three dimensional view of the device 380.

Figure 32A:
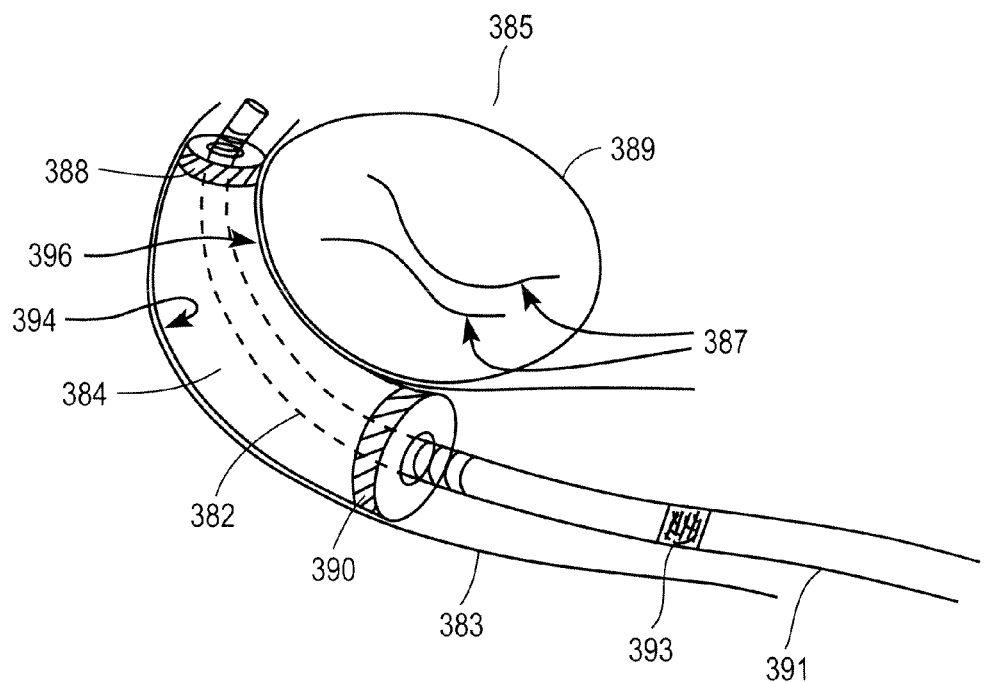
Figure 32B:
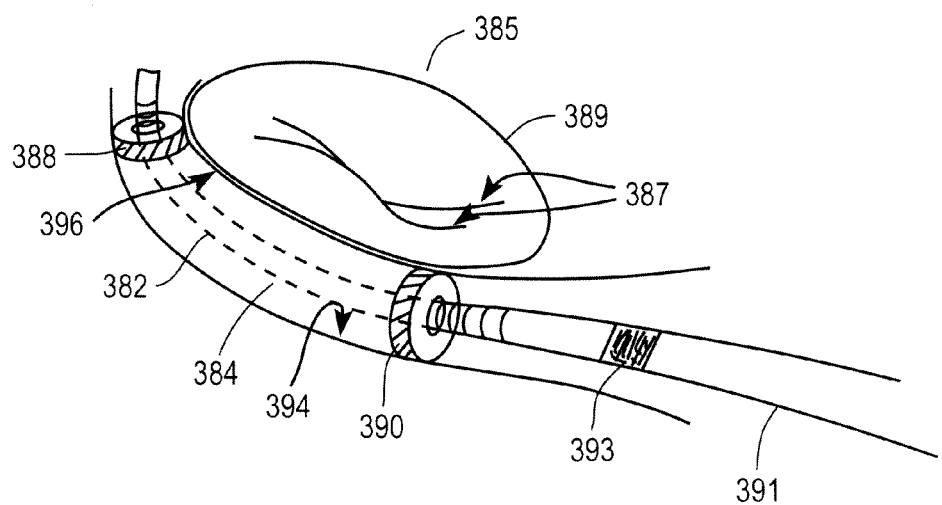

The device 380 can be deployed in the coronary sinus similarly to previously described for the flexural member (or device 230). By rotating the turnbuckle member 382, the threaded sections 390 and 392 work cooperatively with the threaded spacers 386 and 388 to tighten the turnbuckle member 382 within the device shaft 384. One side of the shaft 384 is compressed due to this tightening action. The shape, radius, or the curvature of the coronary sinus is changed accordingly. In the present embodiment, the device 380 can reshape a mitral valve annulus that is encircled by the coronary sinus. The device 380 can be deployed in the coronary sinus with the side 396 being deployed on the side of the coronary sinus that is adjacent the mitral valve. Thus, when the side 396 is compressed due to the tightening of the turnbuckle member 382, the device 380 can place a force on the mitral valve to change the curvature of the mitral valve or the mitral valve annulus. FIG. 32A-32B illustrate an exemplary deployment of the device 380 in a coronary sinus 383. The coronary sinus 383 encircles a portion of a mitral valve 385. Reshaping the device 380 within the coronary sinus 383 also reshapes the mitral valve 385 and/or the mitral value annulus 389. For instance, in FIG. 32A, the device 380 has not been tightened. In FIG. 32B, the device 380 is tightened by having the turnbuckle member 382 rotated with respect to the proximal spacer 388. The more flexible, bendable, or compressible side 396 is placed on the side of the coronary sinus 383 that is away from the mitral valve 385. Where the device 380 is tightened, the side 396 changes its length, or compresses, causing the mitral valve annulus 389 to reshape as shown in FIG. 32B. For example, as shown in the figure, the leaflets 387 of mitral valve are brought closer to each other fixing a condition called mitral valve regurgitation as previously described.

In an alternative embodiment, the device 380 is deployed in a coronary sinus in the opposite orientation to that just described. In such example, the side 396 of the device 380 may be deployed so that it is adjacent to the mitral valve. Thus, when the device 380 is tightened, the side 396 shortens and causes the curvature of the device 380 to curve in the opposite direction forcing the leaflets 387 to be close to each other. This configuration is most effective when the spacers can encircle greater than half the circumference of the mitral valve The turnbuckle member 382 is typically made of a durable material. In one embodiment, the turnbuckle member 382 is made of stainless steel or titanium (or Nitinol). The device shaft 384 can be made of silicone, polyurethane, polyester, or other polymer.

Each of the distal space 388 and the proximal spacer 386 includes a threaded section such that the turnbuckle member 382 can be controllably rotated within the spacers. The spacers can be O-ring members with openings 398 and 399 with threaded inner wall 403 for the turnbuckle member 382 to be threaded therethrough (FIG. 31A-1). FIG. 31A-2 illustrates a cross-sectional view of the spacers.

Additional openings (or additional lumens 401A-401C) may be provided so that the fully deployed device 380 against the inner wall of the vessel would not obstruct the blood flow through the vessel (FIG. 31A-3). The turnbuckle member 382 can be a rod or a wire with screw ends that work cooperatively with the spacers 388 and 386. In one embodiment after the turnbuckle member is inserted through the device shaft 384, the distal end of the turnbuckle member 382 is fixed in place. This is used when there is no need to tighten or adjust the distal end of the device 380. A cap (not shown) can be placed over the distal end of the threaded section 392. An actuator (FIG. 32A-32B) 391 can be removably/releasably coupled to the turnbuckle member 382 in order to allow an operator to turn or adjust the turnbuckle 382. The actuator 391 can be releasably coupled to the turnbuckle 382 via a junction 393 that allows the actuator 391 to be released when all adjustment for the device 380 is completed.

In one embodiment, the device shaft 384 is configured with a lumen for the turnbuckle member 382 to be disposed therethrough. The turnbuckle member 382 needs not be constrained to a particular longitudinal side of the inner space of the device shaft 384. In one embodiment, the turnbuckle is constrained to one side to provide added stability to the device 380.

In an alternative embodiment, a device 400 similar to the device 380 includes two turnbuckle assemblies to provide additional adjustment flexibility (FIG. 31B-1). The device 400 is similar to the device 380 in all aspects except two turnbuckle assemblies are provided. As illustrated in FIG. 31B-1, the device 400 includes a device shaft 426 having a turnbuckle member 376 and a turnbuckle member 378 disposed therethrough. The device shaft 426 is constructed with sides of different flexibilities. In one embodiment, the side 422 of the shaft 426 has less flexibility than the side 424 of the shaft 426. In this embodiment, the variation in flexibility from the side 422 to the side 424 can be smaller since the two turnbuckles can be used to adjust the curvature. The turnbuckles 376 and 378 can be disposed within one lumen provided within the device shaft 426. Each of the turnbuckles 376 and 378 can also be individually confined to a longitudinal side of the device shaft 426 as illustrated in FIG. 31B-1. The device 400 includes a distal spacer 404 and a proximal spacer 402. The spacers 402 and 404 each has at least one opening 405 where the turnbuckle members 376 and 378 can be threaded through as shown in FIG. 31B-2. As illustrated, the distal spacer 402 includes openings 410 and 412. Openings 410 and 412 have threaded sections 407 so that the turnbuckle members 376 and 378 can be controllably threaded therethrough. Similarly, the proximal spacer 402 includes openings 406 and 408, both of which have threaded sections 409 to allow the turnbuckle members 376 and 378 to be controllably threaded therethrough. In a preferred embodiment, the spacers 402 and 404 each includes two separate openings for the two turn buckles members 376 and 378 to be threaded therethrough (FIGS. 31B-3). As before, multiple openings (or lumens) (411A-B) may be provided in the spacers 402 and 404 so that blood flow will not be obstructed when the device 400 is deployed. The threaded sections 414 and 416 of the turnbuckle members 376 and 378, respectively, work cooperatively with the openings 406 and 408 to move the turnbuckle members 376 and 378. Similarly, the threaded sections 418 and 420 of the turnbuckle members 376 and 378, respectively, work cooperatively with the openings 410 and 412 to move the turnbuckle member 376 and 378. The distal sides of the turnbuckle members 376 and 378 can be fixed so that only the proximal ends of the turnbuckle members are moved or adjusted. Providing two or more individually adjusted turnbuckle members such as those provided in the device 400 provides more fine tuning in the device and, thus, provides for more adjustment or reshaping of a vessel.

To use a device 400 and 380, an operator can deliver or place the device within a vessel (or other suitable location) using a catheter. In one embodiment, a delivery device such as those described in U.S. patent application Ser. No. 11/008, 902 is used to deliver the device to the appropriate vessel. In another embodiment, a delivery device and proximal handle such as those described herein are used. The device can be delivered to the vessel via a percutaneous route as described in the mentioned patent application. A conventional delivery method can also be used. The device is deployed in its initial stage. The actuator that is connected to the turnbuckle member extends sufficiently so that the operator can turn the actuator to rotate and tighten the corresponding turnbuckle member deployed within the vessel. In one embodiment, the device is deployed in the initial stage as shown in FIG. 32A. Then once the device is positioned at the proper location within the vessel (an imaging device can be used to monitor the position of the device), the actuator is used to adjust the turnbuckle member(s) to achieve the desired shape for the device (e.g., FIG. 32B). Once the adjustment is complete, the actuator is removed then the delivery device is removed.

FIGS. 33-38A-38B illustrate an exemplary device 430 that utilizes a turnbuckle assembly as previously described to adjust, reshape, or modify a shape of a vessel. The device 430 utilizes one fixed member 432 and one adjustable member 434 to control the adjustment of the device. The fixed member 432 does not allow for a length change whereas the adjustable member 434 does. This feature allows for one side of the device to be compressed while the other side remains fixed. The compressed side thus is able to effectuate a change to the vessel and/or adjacent feature. In one embodiment, as the length of the adjustable member 434 is reduced, the device 430 forms into a curve with the adjustable member 434 having an arc length that is less than the arc length of the member 432.

Figure 37:
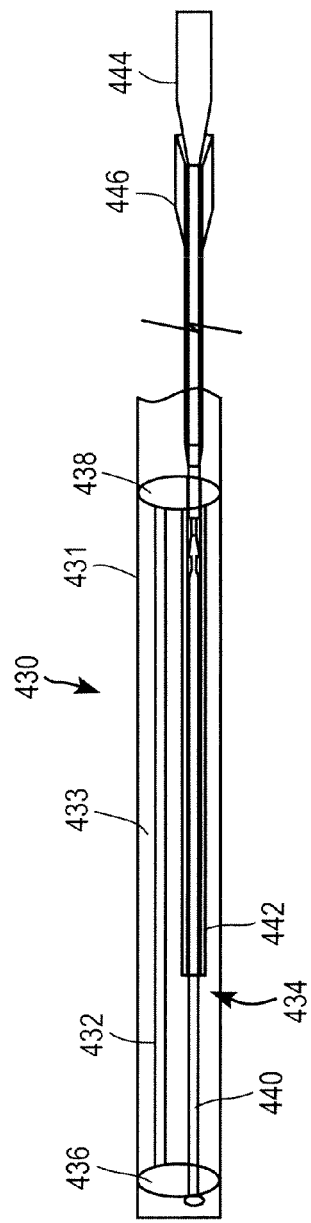

FIG. 37 shows the device 430 to include a distal spacer 436 and a proximal spacer 438. The fixed member 432 and the adjustable member 434 are fixed at both ends into or onto the distal spacer 436 and the proximal spacer 438. In more details, as shown in FIG. 33, the fixed member 432 is fixed to the spacer 438 at location 454 and the adjustable member 434 at location 452. The distal spacer 436 and the proximal spacer 438 are also configured so that the fixed member 432 and the adjustable member 434 are provided with sufficient distance between the members 432 and 434 to allow for a curve to form as the adjustable member 434 is shortened.

As shown in FIG. 37, a device shaft 431 is also provided to house the fixed member 432, the adjustable member 434, and the spacers 436 and 438. The device shaft 431 includes at least one lumen 433 for components of the device to be disposed therethrough such that the blood flow through the vessel is not obstructed.

As illustrated in FIG. 37, the adjustable member 434 comprises two parts, a distal adjustable member 440 and a proximal adjustable member 442 that are configured to engage each other. In one embodiment, the distal adjustable member 440 is controlled by an actuator 444. The adjustable member 434 is stabilized by a stability actuator 446. The distal adjustable member 440 and proximal adjustable member 442 are configured so that the distal adjustable member 440 is turned or retracted within the proximal adjustable member 442, and the length of the adjustable member 434 is controlled by the distal and proximal adjustable members 440 and 442 engaging one another. For instance, a certain turning direction will move the distal adjustable member 442 in and out of the proximal adjustable member 442.

As shown in FIG. 33, in one embodiment, the proximal adjustable member 442 includes a female threaded section 448. The distal adjustable member 440 includes a male threaded section 450, which fits into or over the female threaded section 448. This fitting configuration allows the distal adjustable member 440 and the proximal adjustable member 442 to be turned into and out of each other to shorten or lengthen the adjustable member 434.

In one embodiment, the distal adjustable member 440 is rotated by the actuator 444 releasably connected thereto at a junction 456. In one embodiment, the junction 456 provides a section where pulling and rotating of the distal adjustable member 440 enables detachment of the actuator 444 from the distal adjustable member 440 at the end of a deployment procedure (FIGS. 33-36). The distal end 464 of the actuator 444 has an opening or a blind hole 466 in the end. FIG. 34 shows a cross-section of the distal adjustable member 440 at the blind hole 466. Protrusions 460 are provided at the proximal end 470 of the distal adjustable member 440. The proximal end 470 of the distal adjustable member 440 has a circular cross-section 470. The protrusions 460 fit into slots or openings 462 provided at the distal end of the actuator 444. FIG. 35 shows a cross-section of the slots 462 at the distal end of the actuator 444. The perpendicular side of the protrusions 460 allows the distal adjustable member 440 to be pulled while the sides of the slots 462 allow torque transmission. In FIG. 36, it is shown additional slots 468 may be provided into the inner wall 428 of the actuator 444. At the distal end of the actuator 444 the slots 468 may extend back near the blind hole 466. The slots 468 allow the distal end of the actuator 444 to increase in diameter to fit over the protrusions 460.

In the initial state, the protrusions 460 engage the slots 462. This engagement allows the actuator 444 to rotate the distal adjustable member 440. After all adjustments are completed, the actuator 444 is disengaged from the adjustable member 434 by disengaging the distal adjustable member 440. To disengage the actuator 444, the actuator 444 is advanced distally so that the slots 462 are extended past the protrusions 460. The slots 468 expand to allow this. The actuator 444 is then rotated slightly to place the slots 468 out of alignment with the protrusions 460. The actuator 444 is then retracted and disengaged from the distal adjustable member 440.

It is to be noted that the engagement and disengagement of the actuator 444 from the distal adjustable member 444 can be accomplished by other suitable technique or mechanical features.

Figure 38A:
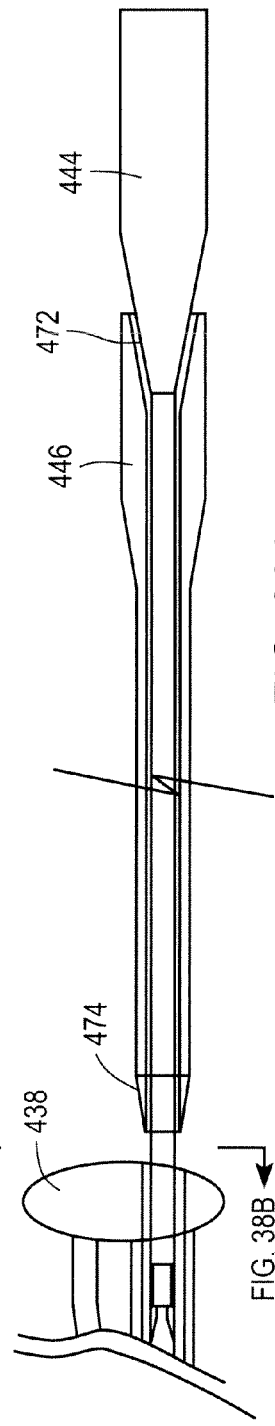
Figure 38B:
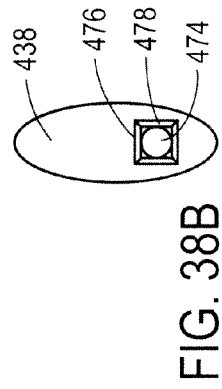

In FIGS. 38A-38B, the stabilizing actuator 446 is shown to be fixed to the proximal spacer 438. In one embodiment, the stabilizing actuator 446 is pushed distally to engage and stabilize the spacer 438 to prevent free rotation of the spacer 438 while the actuator 444 is turned for a particular adjustment. FIG. 38B shows the proximal spacer 438 with more details. The spacer 438 may include an opening 476 configured to prevent rotation. The opening can be square (or rectangular) and may taper distally into a tapered section 478. The distal end of the stabilizing actuator 446 is similarly shaped to fit into such opening. The distal end 474 thus engages a complimentary shaped opening 476. The engagement allows the stabilizing actuator 444 to prevent rotations in the spacer 438 while the actuator 444 is rotated to perform an adjustment.

At the start of a procedure, the actuator 444 can be configured to be fully engaged and touching at mating end 472 as well as engaged into the spacer 438. As the actuator 444 is turned/rotated while the stabilizing actuator 446 is held stationary, the actuator will move proximally while shortening the adjustable member 434. A change in curvature occurs since only the adjustable member 434 is changing in length. In one embodiment, the device 430 is deployed in the coronary sinus similar to previously described. The change in curvature applies a force to the mitral valve annulus that is encircled by the coronary sinus which then may repair the MVR as previously described. In the present embodiment, the amount of force applied to the mitral valve annulus is limited by the column strength of the fixed member 432 and the forces need to torque the adjustable member 434 to change the radius or curvature of the device 430.

In many embodiments, a device similar to the device 380 or 430 is incorporated into a device that includes a distal anchoring member and a proximal anchoring member such as the devices 100, 170, 230, and 311 previously described. The device 380 and 430 can replace or function as a connecting member, connecting the proximal anchoring member to the distal anchoring member. The device 380 and 430 can also replace a telescoping assembly or a flexural member previously described to connect the proximal anchoring member to the distal anchoring member. FIGS. 39A-39D illustrate the device 380 or 430 coupled to the distal and proximal anchoring members.

Figure 39A:
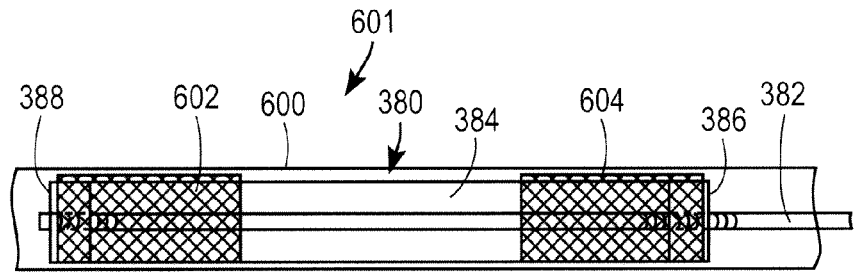
FIGS. 39A-39D illustrate another exemplary embodiment of a device having a proximal anchoring member, a distal anchoring member, and a connecting member that can be adjusted by a turned-buckled assembly in according to embodiments of the present invention.
Figure 39B:
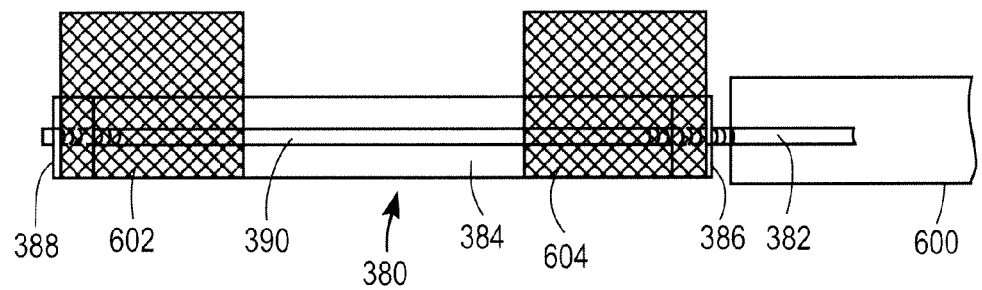

In FIGS. 39A-39B, a device 601 includes the device 380 previously described having a distal anchoring member 602 and a proximal anchoring member 604 coupled thereto. In one embodiment they are placed on or attached to the outer member shaft 384 of the device 380. Conventional methods can be used to achieve the attachments. In one embodiment, a retractable sheath 600 is placed over the distal anchoring member 602 and the proximal anchoring member 604. In many embodiments, the anchoring members 602 and 604 are expandable and compressed during delivery. The retractable sheath 600 confines the anchoring members 602 and 604 in their compressed states until deployment (FIG. 39B). When the retractable sheath 600 is retracted over the anchoring members 602 and 604, the anchoring members 602 and 604 are expanded and deployed. In one embodiment, the distal anchoring member 602 is deployed first. The turnbuckle member 382 is turned so that the outer member shaft 384 is tightened or adjusted as previously discussed. After a particular desired tension is achieved for the outer member shaft 384, the proximal anchoring member 604 is deployed.

Figure 39C:
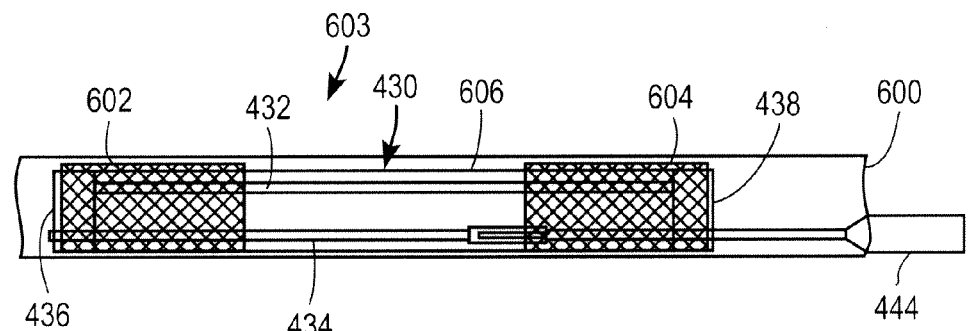
Figure 39D:
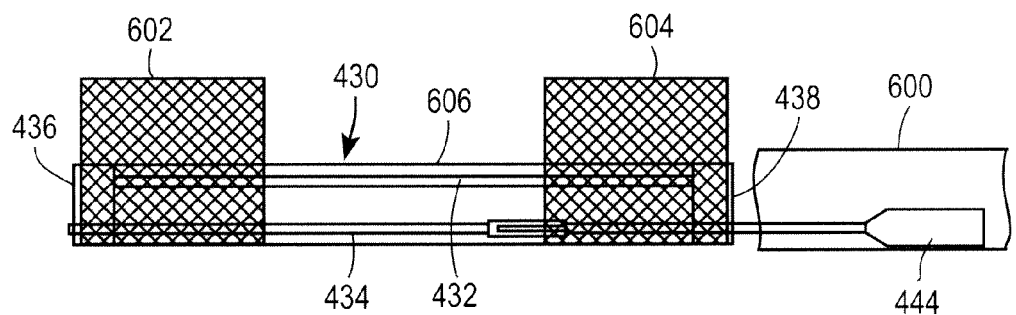

In FIGS. 39C-39D, a device 603 includes the device 430 previously described having a distal anchoring member 602 and a proximal anchoring member 604 coupled thereto. In one embodiment, they are attached to or placed on an outer member shaft 606 of the device 430. Conventional methods can be used to achieve the attachments. In one embodiment, a retractable sheath 600 is placed over the distal anchoring member 602 and the proximal anchoring member 604. In many embodiments, the anchoring members 602 and 604 are expandable and compressed during delivery. The retractable sheath 600 confines the anchoring members 602 and 604 in their compressed states until deployment (FIG. 39D). When the retractable sheath 600 is retracted over the anchoring members 602 and 604, the anchoring members 602 and 604 are expanded and deployed. In one embodiment, the distal anchoring member 602 is deployed first. The adjustable member 434 is turned while the fixed member 432 is maintained static so that the outer member shaft 606 is tightened or adjusted into a particular curve. After a particular desired tension is achieved for the outer member shaft 606, the proximal anchoring member 604 is deployed.

Figure 40:
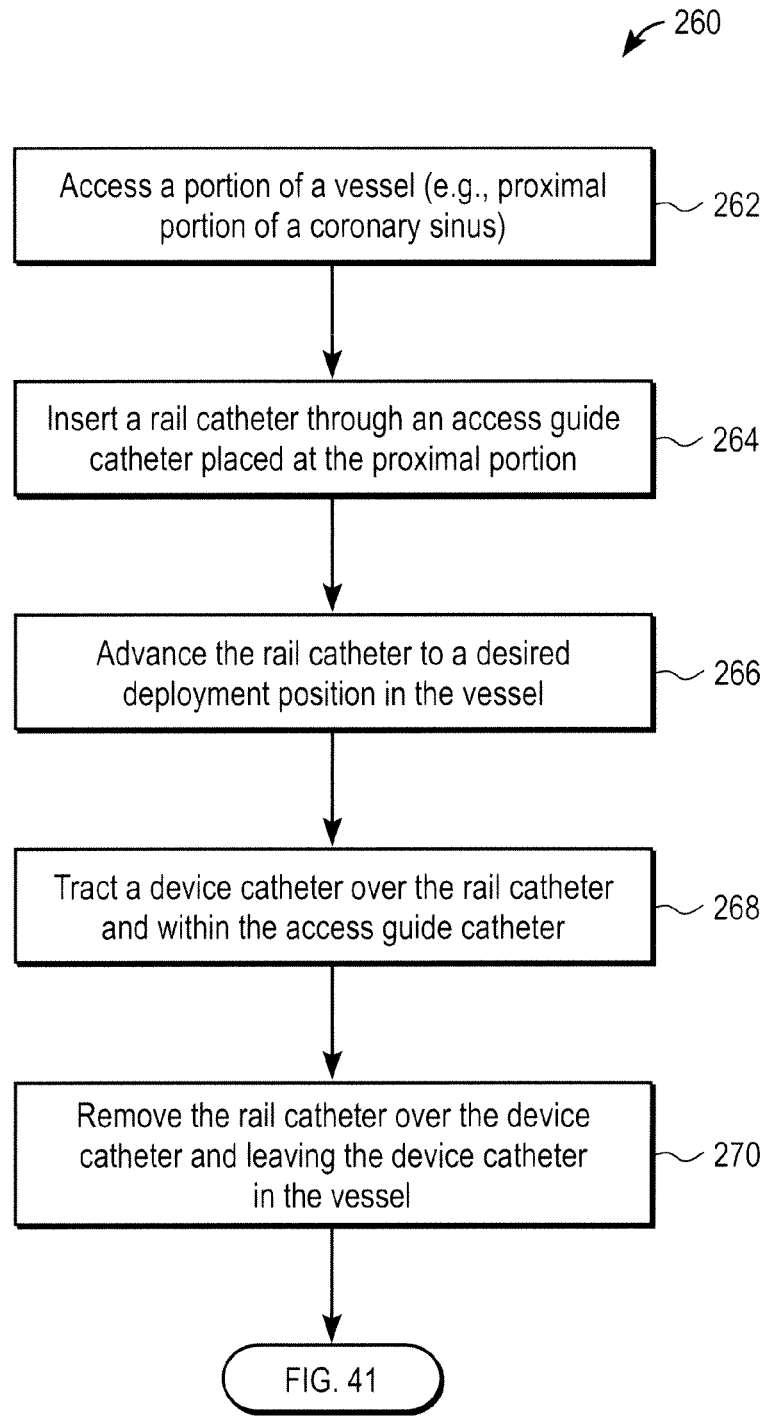
FIGS. 40-41 illustrate exemplary methods of delivering a medical device into a vessel in according to embodiments of the present invention.
Figure 41:
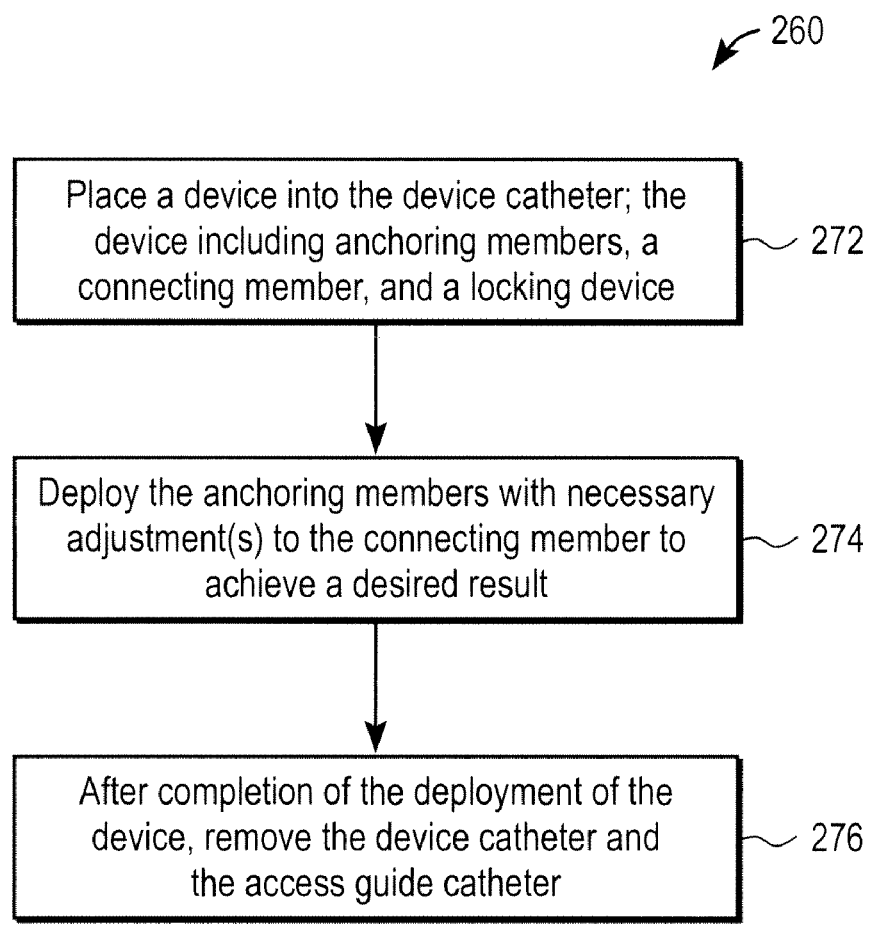

There are several methods that can be used to deliver an exemplary device of the present invention. Examples of apparatuses and methods can be found in U.S. patent application Nos. 10/295,714 and 11/008,902 incorporated herein. FIGS. 40-41 illustrate an exemplary method 260 of delivering a device such as device 100, 170, 230, 380, or 400 to a target location or target vessel of a patient. At operation 262, access to a target location such as a blood vessel is made. In one embodiment, access is made to a proximal portion of a blood vessel such as a portion of a Coronary Sinus (CS). In one embodiment, access to the vessel is accomplished using an introducer sheath and an access guide catheter. At operation 264, a rail catheter is placed through the access guide catheter. The access guide catheter is placed at a proximal portion in the vessel. On the other hand, the rail catheter is placed more distally into the vessel than the access guide catheter. At operation 266, the rail catheter is advanced to a desired deployment position in the vessel. In the example where the vessel is the CS, the rail catheter may be placed more distally into the CS.

Next, at operation 268, a device catheter is advanced over the rail catheter and within the access guide catheter. The device catheter is advanced to the desired deployment position for any of the exemplary devices of the present invention. At operation 270, the rail catheter is removed over the device catheter leaving the device catheter in the vessel. The device catheter provides a conduit for a device to be delivered through.

Next, at operation 272 (FIG. 41), a device is placed into the device catheter. In one embodiment, the device is similar to the assembly 311 (FIG. 25) previously described. In one embodiment, the device is similar to the device 100 (FIG. 7), device 170 (FIG. 12), device 230 (FIG. 21), or device 601/603 (FIGS. 39A-39D) previously described. The device includes a distal anchoring member and a proximal anchoring member connected to one another by a connecting member, which can be a telescoping assembly or a deflectable flexural member. The connecting member is adjustable, in length, in shape, or both. In one embodiment, the device includes a cord that allows for the tightening, lengthening, or adjusting of the connecting member. In one embodiment, the connecting member is a telescoping assembly previously described and the cord is used to telescope the assembly and adjust the length of the telescoping assembly as previously described. In one embodiment, the connecting member is a flexural tube that is compressible on one side and the cord is used to compress the tube adjust the length/shape of the tube as previously described. In one embodiment, the connecting member is a shaft with one or more turnbuckle assembly that is compressible on one side as previously described. The anchoring members are used to anchor the device in the vessel so that the device can cause a change or changes to the vessel as previously discussed. Any of the devices may be placed in a retractable sheath as described for the assembly 311. The device also includes a locking device as previously described. Typically, a proximal adapter is coupled to the proximal end of the device in order to allow an operator to control or actuate the device. The proximal adapter remains proximal to the device catheter and outside of the patient so that the operator can access the adapter.

At operation 274, the anchoring members and the connecting member are deployed. In one embodiment, the distal anchoring member is deployed first. Then, the connecting member is deployed and adjusted (e.g., telescoped, cinched, compressed, tightened, or flexed). Following that, the proximal anchoring member is deployed to hold the connecting member in place after the adjustment. A desired result may include reshaping the vessel, shortening the vessel or a portion of the vessel, or changing the radius or curvature of the vessel. In some applications, reshaping the vessel causes a change to a feature that is adjacent the vessel such as when the device is deployed in a CS to cause a change to a mitral valve annulus encircled by the CS.

The proximal anchoring member and the distal anchoring member are delivered in their compressed states. In one embodiment, to begin deploying the distal anchoring member, a retractable sheath or catheter is retracted proximally while an inner member is used to station the device. An exemplary assembly 311 that can be used for such delivery is described above with reference to FIGS. 25-29. After the distal anchoring member is deployed, the retractable sheath or catheter is retracted further proximally to allow the connecting member to be deployed. A cord may be included in the device to allow for adjustment, compressing, telescoping, or cinching the connecting member at least on one side of the connecting member. After a desired adjustment is accomplished, the cord is locked in place. The retractable sheath is then retracted further proximally to allow the proximal anchoring member to deploy. After the device is deployed successfully, the retractable sheath, the parts of the device that are to be detached after deployment (e.g., the proximal adapter), the device catheter, the access guide catheter, and the introducer sheath are removed from the patient.

One advantage of tracking the device within the device catheter as previously described is that the device catheter has a flexible distal end and may be bent at the distal end allowing the device catheter to conform to the curve of the vessel (e.g., the curve of the CS). Being delivered to the deployment location by traveling through the device catheter, the device can be delivered with less trauma and possible injury to the vessel wall during the delivery since the device travels within the conduit provided by the device catheter. One advantage for using the rail catheter and tracking the device catheter to position using the rail catheter is that a more distal end of the vessel can be selected and then protected (by the device catheter) for the delivery of the device to the location.

Similar delivery method to the method 260 can be used to deliver a device that is similar to the device 380 (FIG. 31A-1), or device 400 (FIG. 31B-1) previously described.

In one exemplary embodiment, the distal end of the device catheter used in a method similar to method 260 is pre-shaped or bent prior to being advanced over the rail catheter (e.g., prior to operation 268). In one exemplary embodiment, the device itself is also bent or pre-shaped prior to being placed into the device catheter (e.g., at operation 272 in method 260). The chosen shape is one that resembles the desired final shape of the device, or one that conforms to the shape of the vessel that the device is delivered into. Additionally, the chosen shape is one that allows optimized orientation control of the device (and its components such as distal and proximal anchoring members and connecting member) once the device is delivered into the vessel. For instance, in some embodiments, the anchoring members include anchors, hooks, or barbs and as such when the device is delivered into the CS, the device is preferably oriented toward the inside of curve of the CS (toward the mitral valve) so that when the anchoring members are deployed, the anchors can penetrate a thicker or stronger tissue side.

Any part of the delivery system, such as the rail catheter, the access guide catheter, the device catheter, or the outer sheath of the device can be pre-shaped or bent to many potential curves or configurations to facilitate the orientation of the device (and its components) once the device is delivered and deployed into a vessel.

Figure 42A:
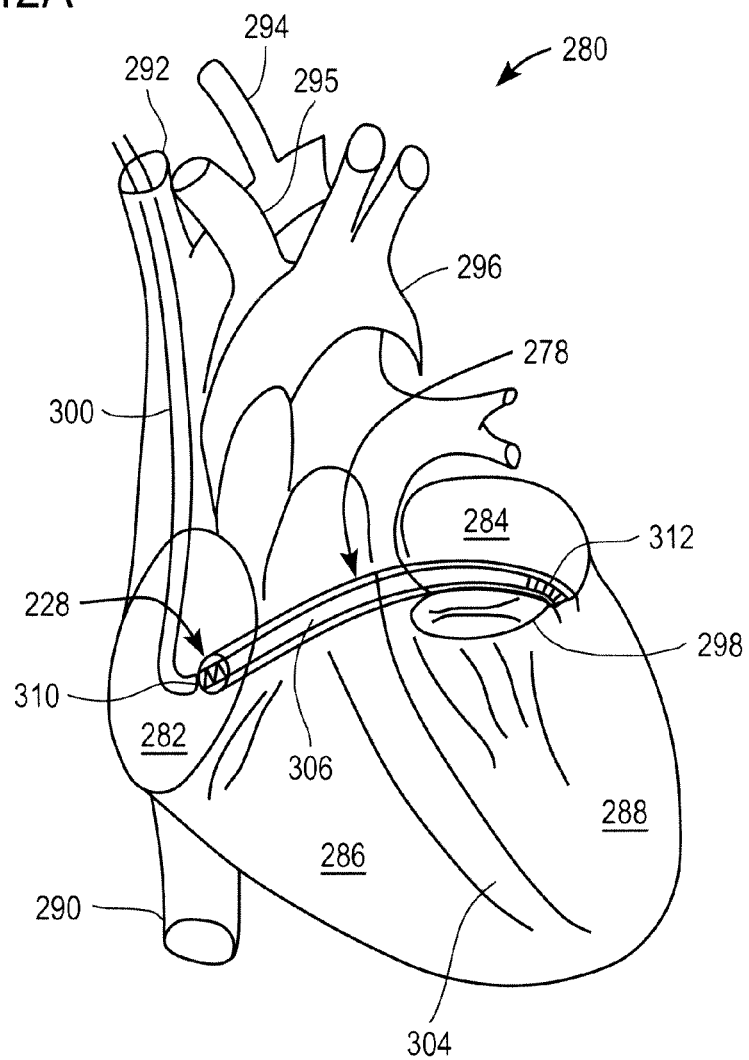
FIGS. 42A-42B illustrate an exemplary method of delivering a medical device into a vessel(s) to repair a heart valve such as a Mitral valve in according to embodiments of the present invention.
Figure 42B:
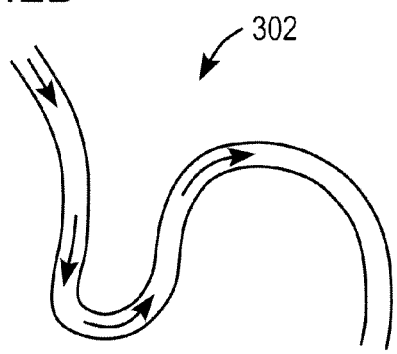

FIGS. 42A-42B illustrate an exemplary embodiment of a device 300 that is delivered with a pre-set curve. In the present embodiment, the device 300 can be any of the devices or assemblies previously described (e.g., device 100, 170, 230, 311, 380, or 400). In the present embodiment, the device 300 is delivered into a heart 280. The heart 280 includes the right atrium (RA) 282, the left atrium (LA) 284, the right ventricle (RV) 286, the left ventricle (LV) 288, and the interventricular septum 304. The superior vena cava (SVC) 292, inferior vena cava (IVC) 290, jugular vein (JV) 294, brachiocephalic trunk 295, and aorta 296 are also shown. The device 300 is delivered into the heart 280 through the SVC 292, and into the CS 278 at a location where the CS 278 encircles the mitral valve (MV) 298.

In one embodiment, the device 300 includes a distal anchoring member 312 and a proximal anchoring member 312 as previously described. The device 300 includes a connecting member 306. In one embodiment, the distal anchoring member 312 is oriented or orientated so that the distal anchoring member 312 is facing the MV 298 as the device 300 is entering the CS 278. In one embodiment, the distal anchoring member 312 and the proximal anchoring member 310 are attached to the device 300 via an attachment spine (e.g., the attachment spine 222 shown in FIG. 19) provided in the anchoring members. The device 300 is orientated so that the attachment spine of the distal anchoring member 312 is facing the MV 298. In one embodiment, the distal anchoring member 312 and the proximal anchoring member 310 include anchors (e.g., the anchors 210 shown in FIGS. 17-18). The device 300 is orientated so that the anchors of the distal anchoring member 312 are facing the MV 298.

During delivery, in the present embodiment, the proximal anchoring member 312 is orientated so that the proximal anchoring member 310 offsets the distal anchoring member 312 by a certain degree (e.g., by about 90-degrees). Thus, in the embodiment where the proximal anchoring member 310 includes the attachment spine, the proximal anchoring member 310 is orientated so that the attachment spine of the proximal anchoring member 310 offsets (e.g., about 90-degrees) the attachment spine in the distal anchoring member 312. In the embodiment where the proximal anchoring member 310 includes anchors, the proximal anchoring member 310 is orientated so that the anchors of the proximal anchoring member 310 offset (e.g., about 90-degrees) the anchors in the distal anchoring member 312. FIG. 42B illustrates an exemplary delivery path 302 where the device 300 travels through. Since there is a bent or change in direction in the path 302 by about 90-degrees, it is optimal to offset the orientation of the anchoring members to one another by about the same degree.

In the embodiment where the device 300 is delivered through the SVC 292, the proximal anchoring member 320's attachment spine is offset by 90-degrees clockwise to the attachment spine of the distal anchoring member 312. In an alternative embodiment, the device 300 is delivered through the IVC 290, and in such embodiment, the proximal anchoring member 310's attachment spine is offset by about 90-degrees counter-clockwise to the attachment spine of the distal anchoring member 320. Thus, certain sections of the device that is delivered into a vessel such as the CS 278 and that is delivered through a curved pathway can be pre-shaped to have a certain curve to facilitate the movement and orientation of the components of the device.

In one embodiment, the proximal anchoring member and the distal anchoring member's attachment spines are not oriented similarly to each other during delivery even though once both of the anchoring members are deployed inside the vessel (e.g., the CS 278), both of the anchoring members are facing toward the same orientation, such as both facing the MV 298. In the present embodiment, the anchoring members also include attachment spines and/or anchors. As can be seen in FIG. 42A, when the device 300 is delivered into the SVC 292 or the IVC 290, it would be difficult to get the proximal and distal anchoring members to face the same direction with respect to their attachment spines and/or anchors due to the different curve directions and turns present in the delivery path. For instance, the distal end of the device with the distal anchoring member enters the RA 282 via the SVC 292 and is positioned distally into the CS 278 via the CS ostium 228. The lowest energy state of the curved portion of the device 300 is with the curve in alignment with the CS 278 curve. Thus, when the outer sheath of the device 300 is retracted to deliver the distal anchoring member 312, the desired orientation of the distal anchoring member is obtained (e.g., to have the attachment spine and/or anchors orientating toward the MV 298).

However, to deliver and deploy the proximal anchoring member 310 so that its attachment spine will be orientated toward the MV 298, the proximal anchoring member 310 is rotated approximately 90-degrees because as the outer sheath of the device 300 is retracted proximally to deliver the proximal anchoring member 310, the device 300 tends to rotate due to the change in the curvature in the path of delivery. In one embodiment, when the connecting member of the device 300 is a telescoping assembly, a proximal telescoping member and a distal telescoping member included in the telescoping assembly are also free to rotate relative to each other. Thus, when the device 300 is retracted more proximally to deploy the proximal anchoring member at the ostium 228 of the CS 278, the proximal telescoping member tends to rotate due to the change in the delivery path from the CS distal portion to the CS ostium 228. By presetting the curve of the proximal section of the device with about a 90-degree offset with respect to the distal section of the device, the rotation caused to the device due to the change of the curve or direction in the delivery path would orientate the proximal section to the same direction as the distal section. Other degree of offsets of certain sections of the devices are entirely possible depending on the curvature or direction change in the delivery path the device travels through to reach the deployment location.

Figure 43A:
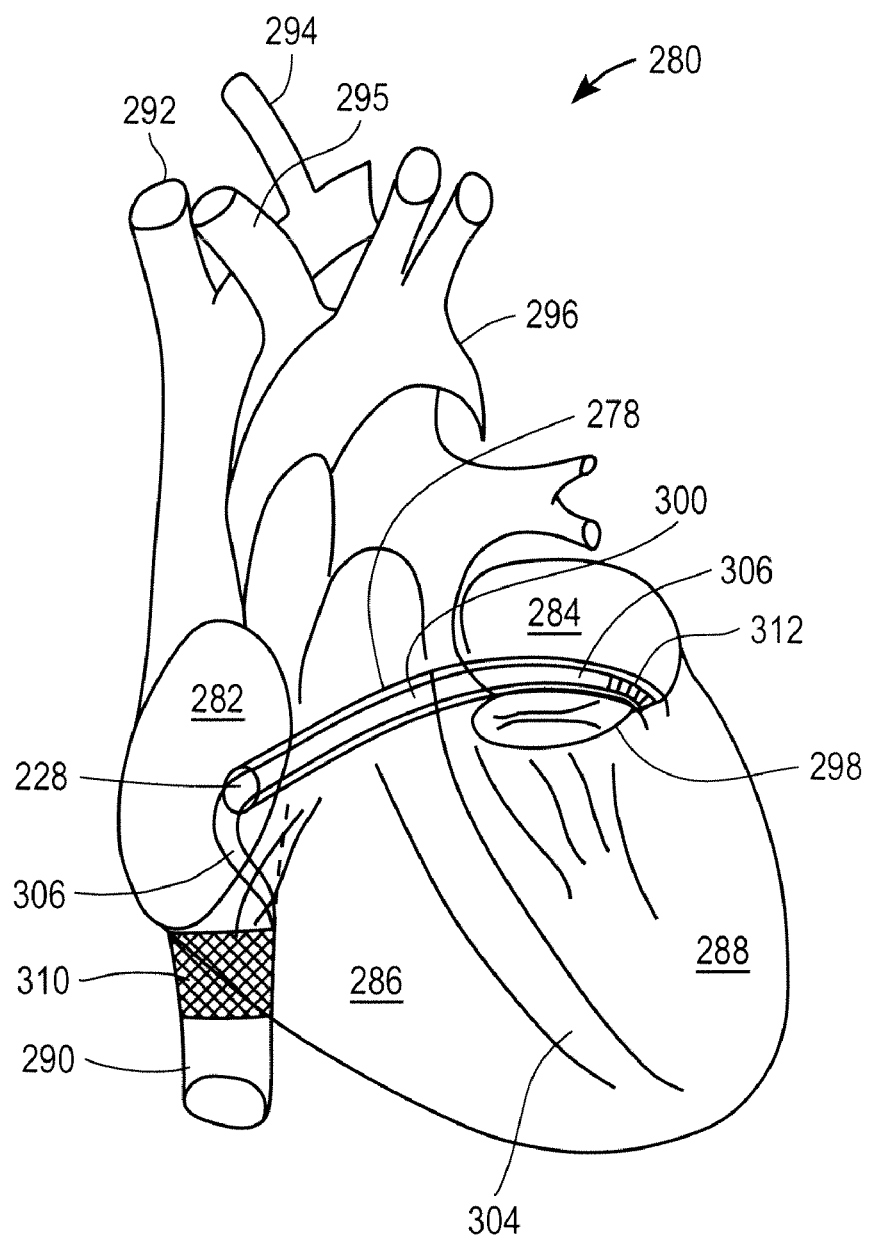
FIGS. 43A-43C illustrate exemplary methods of delivering a medical device into a vessel(s) to repair a heart valve such as a mitral valve in according to embodiments of the present invention.

FIG. 43A illustrates an exemplary embodiment of the device 300 delivered the heart 280 with the proximal anchoring member 310 being deployed in the IVC 290 and the distal anchoring member 312 being deployed in the CS 278. The device 300 can also be pre-set to have a particular curve or shape and the distal section of the device 300 being offset by the proximal section of the device (e.g., by 90-degrees) as previously described. The IVC 290 can be a preferred deployment site for the proximal anchoring member 310 because the IVC 290 ostium into the RA 282 is located very close to the CS ostium 228. Positioning the proximal anchoring member 310 in the IVC 290 may prevent or minimize possible deformation to the RA 282. The IVC 290 is also a bigger vessel of thicker vessel wall as well as having a lot of connective tissue.

Figure 43B:
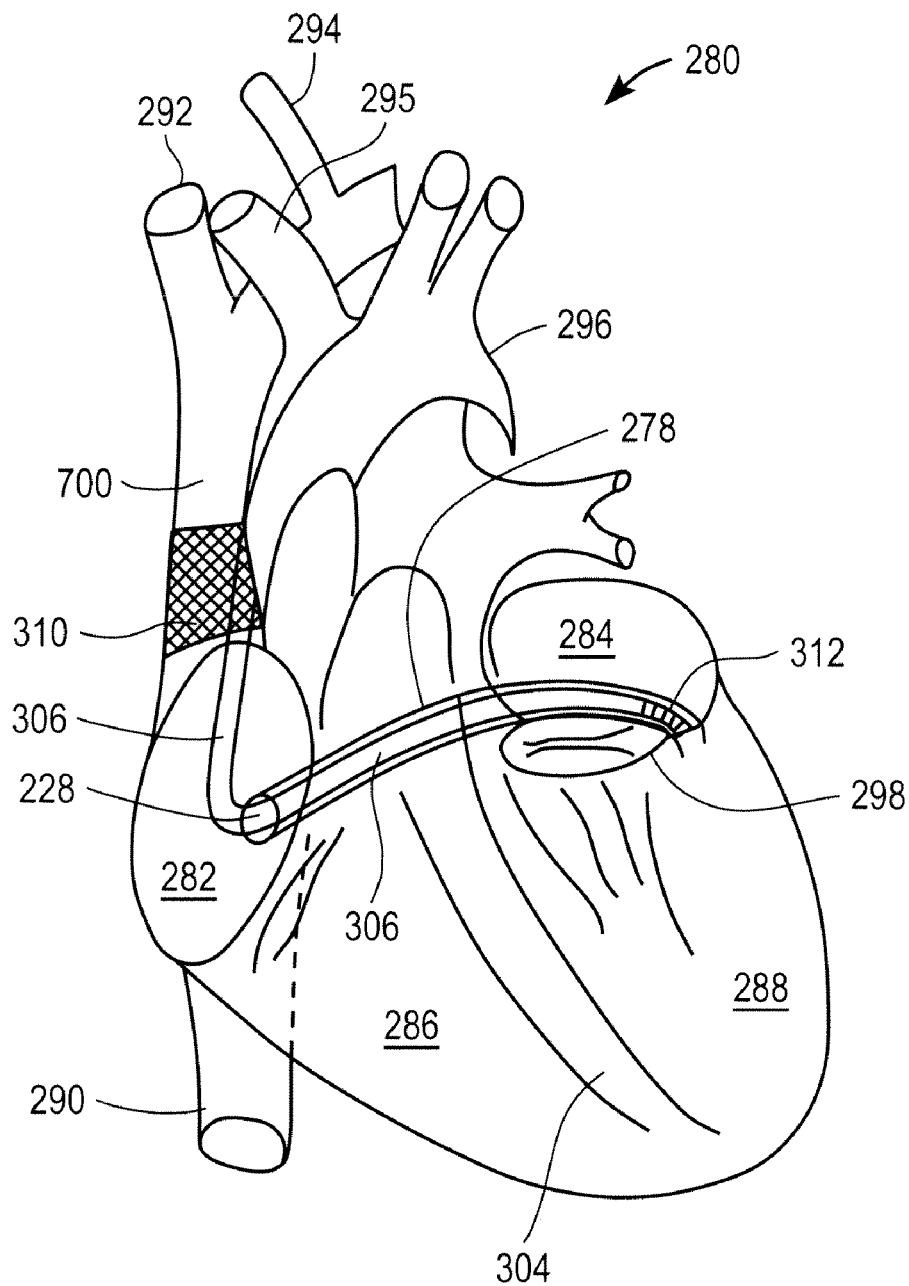

FIG. 43B illustrates an exemplary embodiment of the device 300 delivered the heart 280 with the proximal anchoring member 310 being deployed in the SVC 292 and the distal anchoring member 312 being deployed in the CS 278. The device 300 can also be pre-set to have a particular curve or shape and the distal section of the device 300 being offset by the proximal section of the device (e.g., by 90-degrees) as previously described.

Figure 43C:
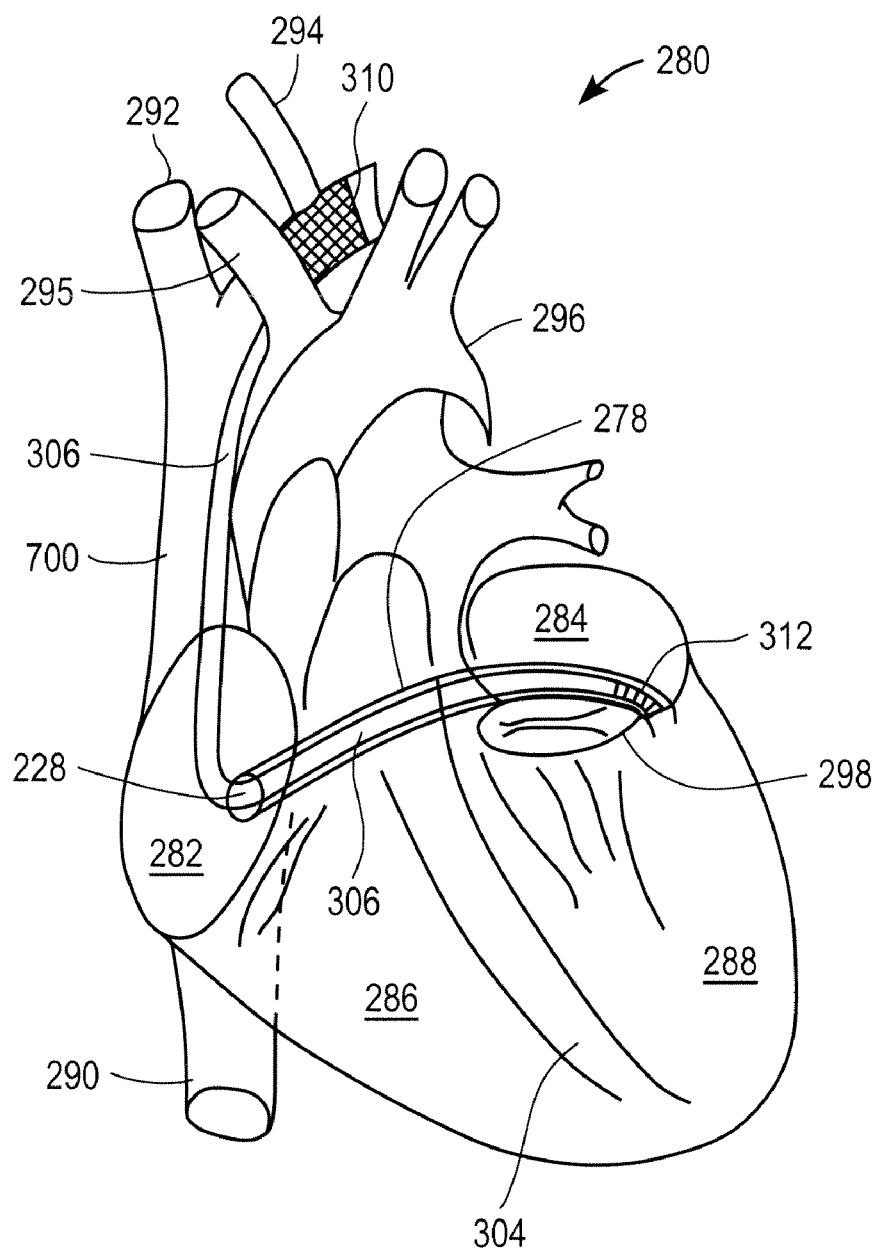

FIG. 43C illustrates yet another exemplary embodiment of the device 300 delivered the heart 280 and in this embodiment, the proximal anchoring member 310 is deployed in the JV 294 and the distal anchoring member 312 being deployed in the CS 278. The device 300 can also be pre-set to have a particular curve or shape and the distal section of the device 300 being offset by the proximal section of the device (e.g., by 90-degrees) as previously described.

In another embodiment (not shown), the proximal anchoring member 310 is deployed in the brachiocephalic trunk 295 and the distal anchoring member 312 being deployed in the CS 278. The device 300 can also be pre-set to have a particular curve or shape and the distal section of the device 300 being offset by the proximal section of the device (e.g., by 90-degrees) as previously described.

In many embodiments, the distal anchoring member is typically deployed prior to the proximal anchoring member being deployed. The following exemplary embodiments discuss methods and apparatuses that can be used to deploy the proximal anchoring member prior to deploying the distal anchoring member. Example of the device described below can be found in U.S. patent application Ser. No. 10/464,132 incorporated herein.

Figure 44:
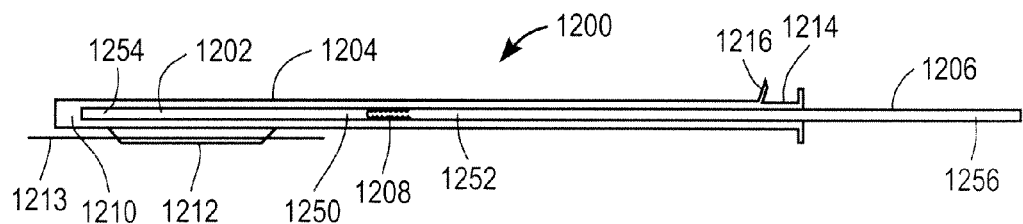
FIGS. 44-46 illustrate an exemplary device of the present invention.

FIG. 44 illustrates an exemplary device 1200, which comprises an implantable device 1202 moveably disposed within a delivery sheath 1204. The implantable device 1202 generally forms the distal anchoring member and the proximal anchoring member connected by a wire once the delivery sheath 1204 is removed. Details of forming the implantable device 1202 can be found in U.S. patent application Ser. No. 10/464,132 incorporated herein. The implantable device 1202 is releasably coupled to an actuator 1206 at a junction 1208. The actuator 1206 may be used to deploy, advance, retract, or otherwise, move the implantable device 1202 into, out of, or within the delivery sheath 1204.

The delivery sheath 1204 is made out of a biocompatible material such as those typically used for a catheter. The delivery sheath 1204 can be made out of a polymer commonly used in catheter construction such as Nylon, Pebax, Polyurethane, Polyolefin, etc . . . The delivery sheath 1204 is flexible but need not be and can be made to have preformed curvature to facilitate the maneuvering of the delivery sheath 1204 into the target blood vessel (e.g., a coronary sinus). The delivery sheath 1204 is sufficiently strong to hold the device 1202 in its delivery state until ready for deployment.

The delivery sheath 1204 constrains the implantable device 1202 in the pre-delivery or pre-deployment state. In one embodiment, in the pre-deployment state, the implantable device 1202 holds a temporary shape that allows it to be conveniently disposed within the delivery sheath 1204 (e.g., a relatively straight structure as shown in FIG. 44). The implantable device 1202 thus has an original preformed shape that can be temporarily changed, constrained, or shaped to fit into the delivery sheath 1204. Withdrawal of the delivery sheath 1204 deploys the implantable device 1202 allowing it to return to the original preformed shape The delivery sheath 1204 has an elongated lumen 1210, a guidewire lumen 1212, and a proximal connector 1214. The guidewire lumen 1212 allows for a guidewire 1213 to be inserted therein to guide the delivery sheath 1204 to the treatment site. The guidewire lumen 1212 may not be needed or included with the delivery sheath 1204 since there are other techniques that can be used to introduce the delivery sheath 1204 to the treatment site. For instance, the device 1202 and the delivery sheath 1204 can be delivered using the method 260 previously mentioned. Using the guidewire 1213 and the guidewire lumen 1212 is only one exemplary technique of introducing the delivery sheath to the treatment site. The use of a sub-selective sheath is another method that can be used to introduce the delivery sheath to the treatment site. Exemplary methods of delivering a device previously discussed can also be used. The proximal connector 1214 allows for the medical device 1200 to be flushed with a fluid when necessary. For example, a syringe (not shown) can be attached to the proximal connector 1214 at point 1216 and a fluid can be introduced thereto to a desired treatment site. Alternatively, a fluid can be introduced to lubricate the implantable device 1202 and the inner space of the delivery sheath 1204 to minimize friction between the implantable device 1202 and the delivery sheath 1204 so as to allow the implantable device 1202 to be easily moved within the delivery sheath 1204. The delivery sheath 1214 may also include radiopaque markers (not shown) to provide positioning information. The delivery sheath 1214 may also include other type of markers compatible with various types of imaging techniques known in the art such as echo imaging, infrared illuminations x-ray, and magnetic resonance imaging.

Figure 45:
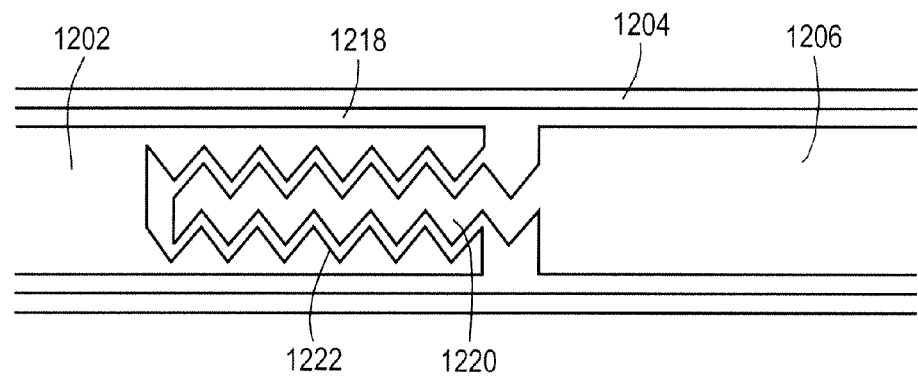
Figure 46:
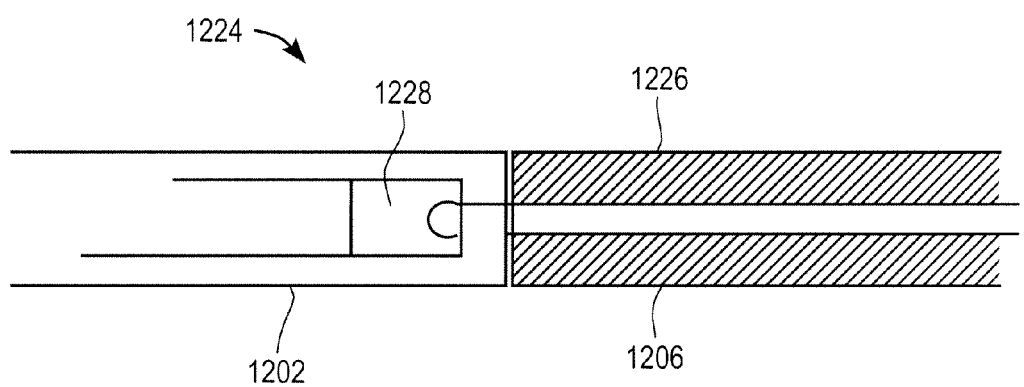

In one embodiment, the actuator 1206 is moveably disposed within the delivery sheath 1204. In other embodiments, the actuator 1206 is moveably and partially or completely disposed outside of the delivery sheath 1204. The actuator 1206 thus need not be disposed within the delivery sheath 1204. The junction 1208 where the actuator 1206 engages the implantable device 1202 may be disposed within the delivery sheath 1204 to prevent accidental disengagement. The actuator 1206 may be a hollow or a solid member, rod, or wire and may be coated with a lubricious material that facilitates the movement of the actuator 1206 in and out of the delivery sheath 1204. The actuator 1206 is releasably coupled to the implantable device 1202 in a way that allows the actuator 1206 to engage or disengage, attach to or detach from the implantable device 1202 when desired (FIGS. 45-46). For deployment of the implantable device 1202, the actuator 1206 engages the implantable device to move and/or facilitate in deploying the implantable device. After the deployment of the implantable device 1202, the actuator 1206 disengages the implantable device 1202 and can be withdrawn from the blood vessel or the coronary sinus.

FIGS. 45-46 illustrate enlarged view of the junction 1208, which is the connecting point for the actuator 1206 and the implantable device 1202. In one embodiment, the actuator 1206 is coupled to the implantable device 1202 through a connection mechanism 1218 as shown in FIG. 45. The connection mechanism 1218 includes a screw thread structure 1220 and a complimentary screw thread structure 1222. The screw thread structure 1220 couples to or extends from the actuator 1206 at the distal end section 1252 of the actuator 1206. The screw thread structure 1222 couples to or extends from the implantable device 1202 at the proximal end section 1250 of the implantable device 1202. One of the screw thread structure 1220 and the screw thread structure 1222 can be a female thread structure while the other can be a complimentary male thread structure. As shown in FIG. 46, the screw thread structure 1222 is a female thread structure and the screw thread structure 1220 is a male thread structure. The screw thread structure 1220 and screw thread structure 1222 engage one another to couple the implantable device 1202 to the actuator 1206. The screw thread structure 1220 and the screw thread structure 1222 disengage one another to release or detach the actuator 1206 from the implantable device 1202. Thus, during deployment, the screw thread structure 1220 and the screw thread structure 1222 engage one another to allow the actuator 1206 to move the implantable device 1202 and after the deployment, the screw thread structure 1220 and the screw thread structure 1222 disengage one another to allow the actuator 1206 to be detached from the implantable device 1202.

It is to be appreciated that there are many connection mechanisms that rely on a rotary and/or longitudinal motion and/or release of the implantable device 1202. Alternatively, the actuator 1206 can be coupled to the implantable device 1202 using a loop connection system 1224 as illustrated in FIG. 46. The proximal section 1250 of the implantable device 1202 may include a loop, opening, or a slot 1228. The distal section 1252 of the actuator 1206 may include a wire loop 1226 that can be inserted through the slot 1228. The wire loop 1226 keeps the actuator 1206 coupled to the implantable device 1202 until the removal of the wire loop 1226 from the slot 1228. The wire loop 1226 may be removed by releasing one end of the wire loop 1226 while pulling on the other end of the wire loop 1226. The wire loop 1226 holds the implantable device 1202 against the actuator 1206 such that the implantable device 1202 can be pushed or pulled by the actuator 1206. The wire loop 1226 may simply act to couple the implantable device 1202 to the actuator 1206 while the actuator 1206 is the member that performs the controlling or moving of the implantable device 1202.

In previously disclosures (e.g., U.S. patent application Ser. No. 10/464,132), a device such as the device 1202 is deployed in a way that the distal section of the device is deployed first for the distal anchoring member to form followed by the proximal section of the device being is deployed for the proximal anchoring member to form. The middle section of the device 1202 is a connecting member. FIGS. 47-52 illustrate an exemplary process where the proximal section of the device is deployed first followed by the distal section of the device being deployed. Deploying the proximal section first may simplify the tensioning of the connecting member of the device.

Figure 47:
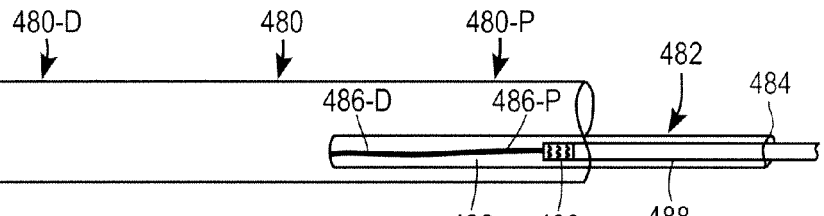
FIGS. 47-54 illustrate an exemplary method of deploying a proximal anchoring member first prior to deploying a distal anchoring member.
Figure 52:
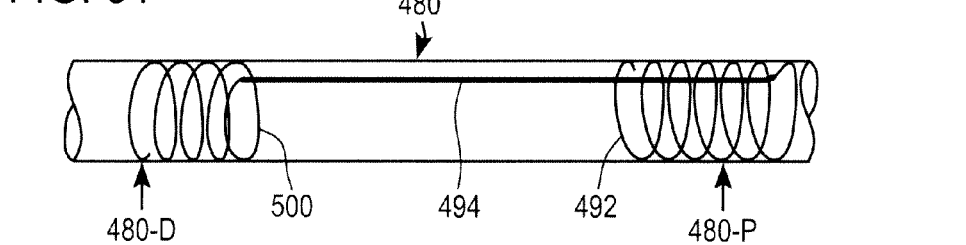

In FIG. 47, an assembly 482 including an implantable device 486 disposed within a delivery sheath 484 is inserted into a vessel 480. An actuator 488 is releasably coupled to the proximal end of the implantable device 486 at a junction 490. Previously discussed methods can be used to deliver the assembly 482 into the vessel, for example, method 260 or methods disclosed in U.S. patent application Ser. No. 11/008, 902 or 10/464,132 incorporated herein. The device 486 is similar to the device 1202 previously described except that the distal section 486-D of the device 486 forms a proximal anchoring member 492 and the proximal section 486-P of the device 486 forms a distal anchoring member 500 once the delivery sheath 484 is retracted and the device 486 is fully deployed (FIG. 52). The proximal anchoring member 492 refers to the anchoring member that is deployed at the proximal position 480-P in the vessel 480 and the distal anchoring member 500 refers to the anchoring member that is deployed at the distal position 480-D in the vessel 480. But from the perspective of the device 486, it is the distal section 486-D of the device that forms the proximal anchoring member 492 and it is the proximal section 486-P of the device that forms the distal anchoring member 500. In one embodiment, the device 486 is delivered into the CS similar to previously discussed.

Access to a vein (e.g., femoral, jugular, subclavian, etc . . . ) in a patient's body is gained using a cut-down or an introducer sheath procedure. In one embodiment, the vein is used to introduce the assembly 482 that includes the delivery sheath 484, the implantable device 486, and the actuator 488 into the right atrium (not shown) and then into the coronary sinus of the heart 280 previously shown. In one embodiment, the vein is used to introduce the assembly to a particular vessel, vessel 480. In the introducer sheath procedure, a procedure known in the art, the operator introduces the introducer sheath (not shown) into the vein through the patient's skin percutaneously. A needle or a similar puncture device (not shown) provides entry into the vein. The proximal end of the needle remains outside of the introducer sheath and is withdrawn. A distal end of a guide catheter (not shown) with a flexible guidewire (not shown) within a lumen of the guide catheter is inserted into the proximal end of the introducer sheath and advanced therethrough until the distal end of the guidewire or the guide catheter reaches the distal section of the vessel.

In one embodiment, a first guidewire and a guide catheter (not shown) are manipulated to gain access to the vessel 480. The first guidewire is removed once the guide catheter is in place. A second guidewire is then placed within the guide catheter. The second guidewire is configured to be used with the assembly 482. The assembly 482 is then inserted into the vessel over the guidewire and through the guide catheter.

Figure 48:
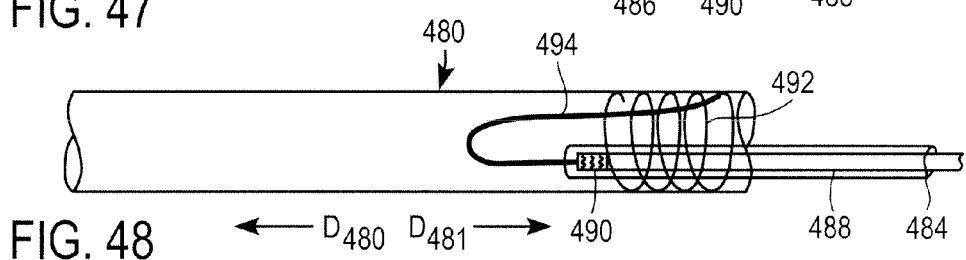

In FIG. 48, the distal section 486-D of the device 486 is deployed. A proximal anchoring member 492 is formed and deployed at the proximal section 480-P within the vessel 480. In one embodiment, to deploy the proximal anchoring member 492, the actuator 488 is pushed distally in the direction D480 to force the proximal anchoring member 492 out of the delivery sheath 484. The delivery sheath 484 may also be withdrawn proximally in the direction D481 to facilitate the positioning and deployment of the proximal anchoring member 492. Withdrawing the delivery sheath 484 allows the proximal anchoring member 492 to expand to the original preformed shape, e.g., a coiled structure. Before the delivery sheath 484 is withdrawn, the actuator 488 is advanced distally in the D480 direction to initiate the coiling of the proximal anchoring member 492 to allow it to form into the preformed coiled structure. After the proximal anchoring member 492 is fully deployed, the anchoring member 492 engages the inner wall of the vessel 480 as shown in FIG. 48. The outer diameter of the proximal anchoring member 492 is pressed against the inner wall of the vessel 480. In one embodiment, the actuator 488 is used to adjust the deployment position for the proximal anchoring member 492 after the delivery sheath 484 is retracted.

Figure 49:
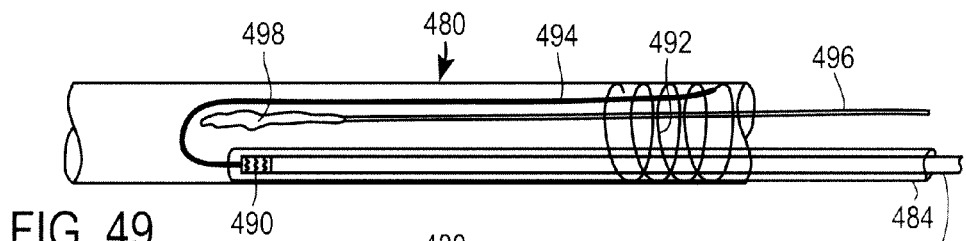

In FIG. 49, a connecting member 494 of the device 486 is deployed and positioned. Once the proximal anchoring member 492 is deployed and anchored in place, the delivery sheath 484 is pushed distally in the direction D481 while the actuator 488 moves even more distally in the direction D480 to allow the connecting member 494 to be deployed. The actuator 488 and the sheath 484 are also used together to adjust the position of the connecting member 494. In one embodiment, the connecting member 494 is placed along one side of the inner wall of the vessel 480. In one embodiment, the connecting member 494 is formed, at least partially, from preformed coiled sections and then the tension that is placed on the connecting member 494 will straighten out the coils into a nearly straight and flat connecting member 494. Urging or pushing on the actuator 488 and the sheath 484 while the proximal anchoring member 492 is already deployed in place will straighten out the preformed coils in the connecting member 494 and deploy the connecting member 494 against the particular side of the inner wall of the vessel 480.

An expandable member (e.g., a balloon) 498 is used to hold the connecting member 494 in place. The balloon 498 is inflated/deflated by an access 496. In one embodiment, the balloon 498 is inflated to hold the connecting member 494 in place so that the distal anchoring member can be deployed. In one embodiment, the balloon 498 holds the tension on the connecting member 494 while the distal anchoring member is being deployed.

Figure 50:
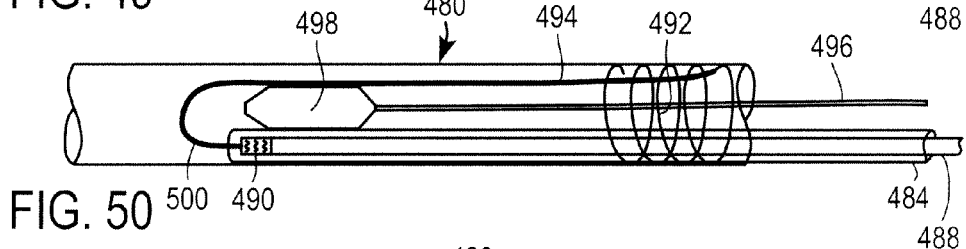

In FIG. 50, the distal anchoring member 500 is deployed. In one embodiment, the delivery sheath 484 is still placed over a portion of the device 486, e.g., the delivery sheath 484 is not retracted pass the junction 490. The balloon 498 is inflated via the access 496. The inflated balloon keeps tension on the connecting member 494 and/or the delivery sheath 484. The device 486 is urged distally in the direction D480 to allow distal anchoring member 500 to form. Similar to the proximal anchoring member 492, the distal anchoring member 500 expands to the original preformed shape, e.g., a coiled structure when the actuator 488 urges the device 486 beyond the end of the delivery sheath 484 (FIG. 51).

Figure 51:
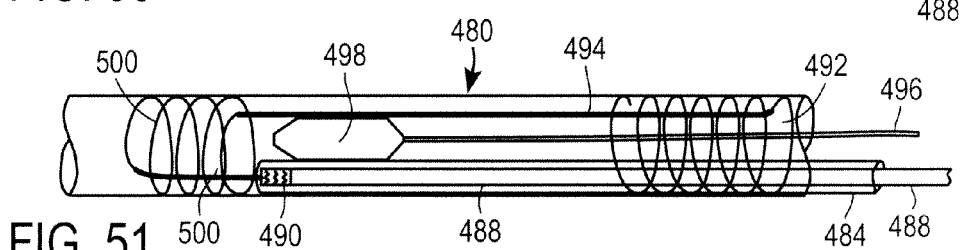

After the distal anchoring member 500 is fully deployed, the anchoring member 500 engages the inner wall of the vessel 480 as shown in FIG. 51. The outer diameter of the distal anchoring member 500 is pressed against the inner wall of the vessel 480. In one embodiment, the actuator 488 is used to adjust the deployment position for the distal anchoring member 500 after the delivery sheath 484 is retracted. The balloon 498 remains inflated until the distal anchoring member 500 is deployed and positioned as desired.

The amount of tension may also be limited by the anchoring ability of the distal anchoring member 500 and the proximal anchoring member 492. The stronger the anchoring ability of the distal anchoring member 500 and the proximal anchoring member 490, the stronger the tension that can be place on the connecting member 494. The balloon 498 is deflated to check the tension and resulting effect on the mitral valve. If tension needs to be adjusted, the actuator 488 can be used to move the distal anchoring member 500 back into the delivery sheath and the tension is adjusted for the connecting member 494. The deployment of the distal anchoring member 500 can then be repeated after the tension is adjusted. Once the tension is satisfactory, the actuator 488 is disengaged from the device 486, After the device 486 is completely deployed, the balloon 498, the actuator 488, and the delivery sheath 484 are removed from the vessel 480 as shown in FIG. 52.

Figure 53:
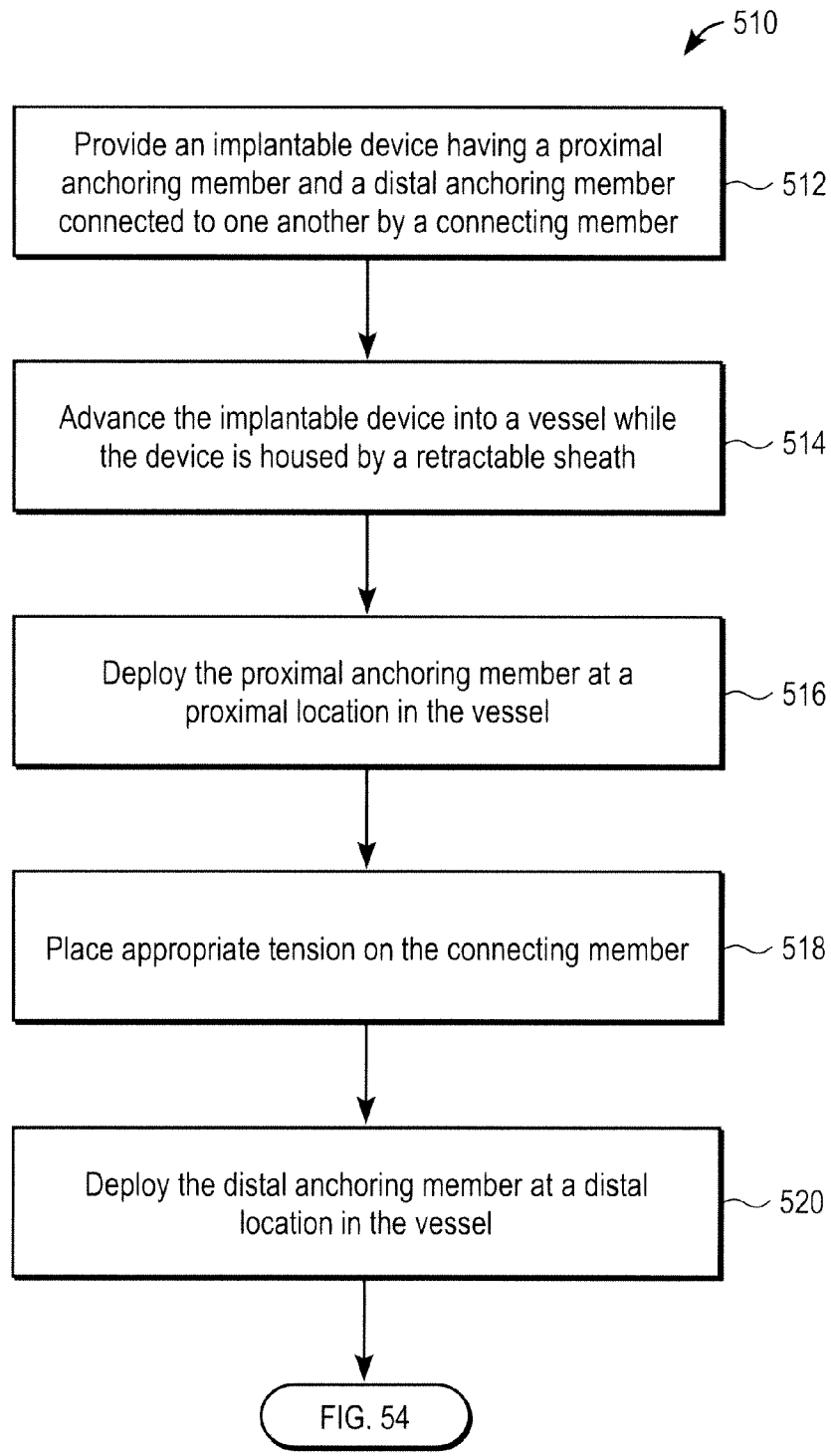
Figure 54:
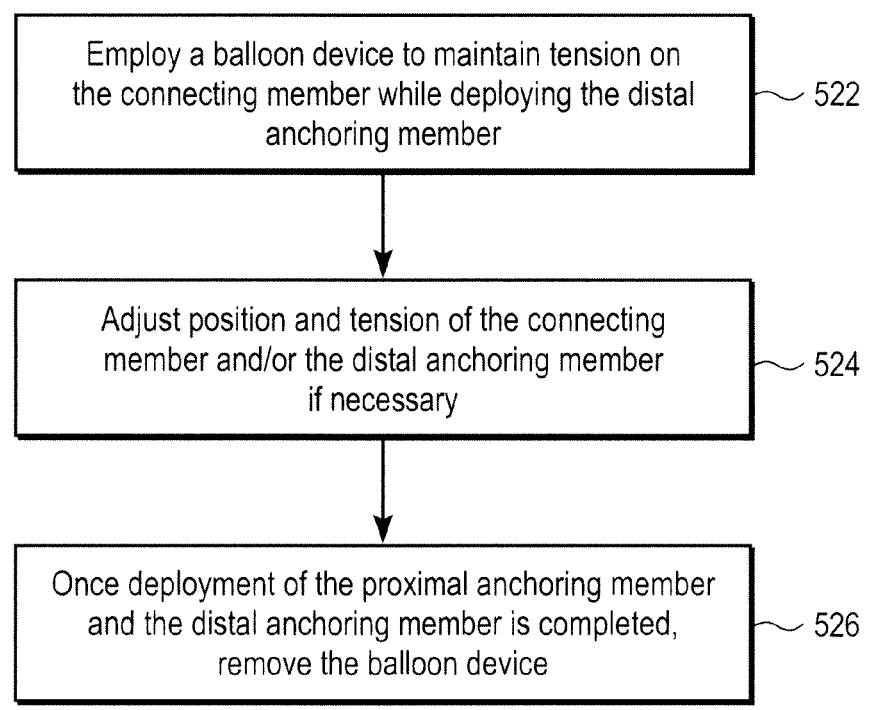
Figure 55:
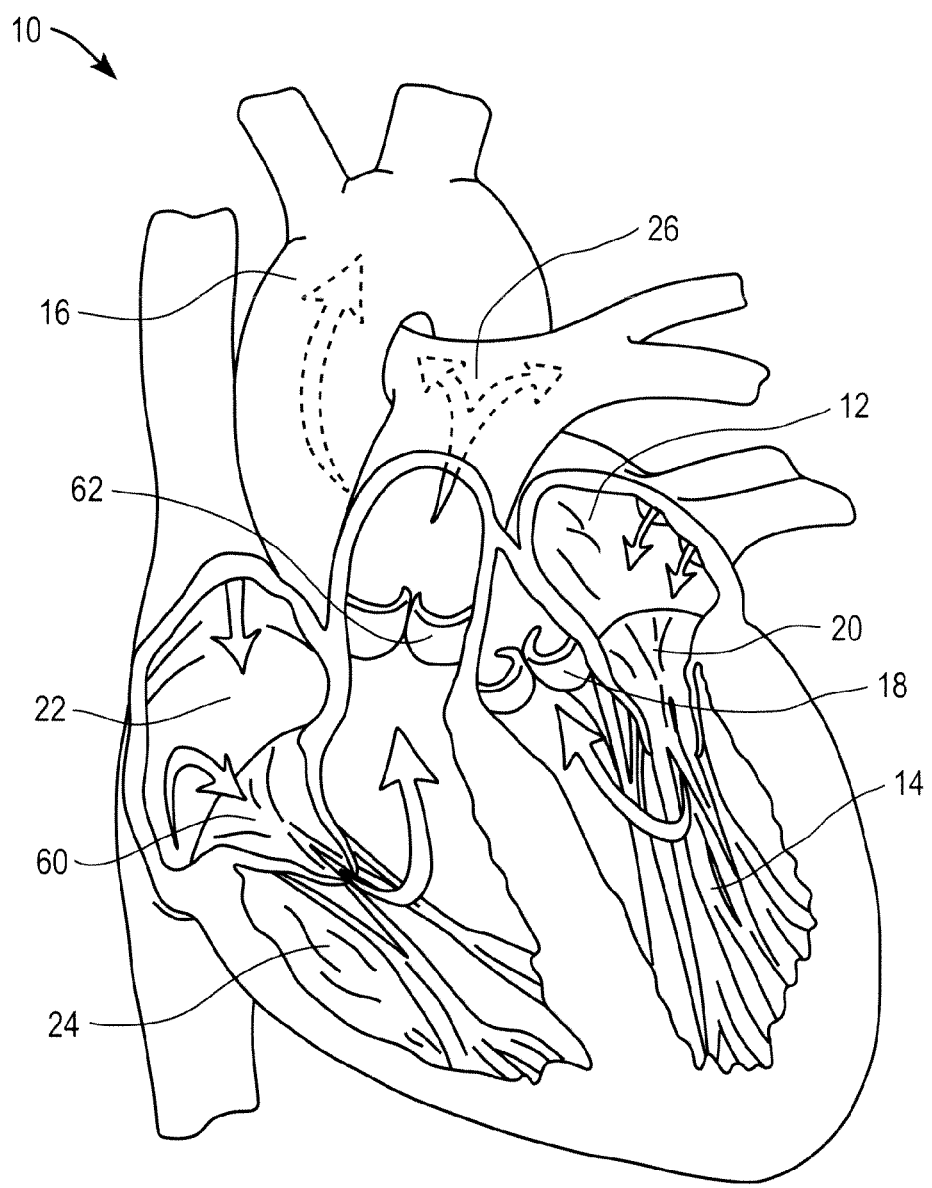
FIG. 55 is an illustration of a heart.
Figure 56:
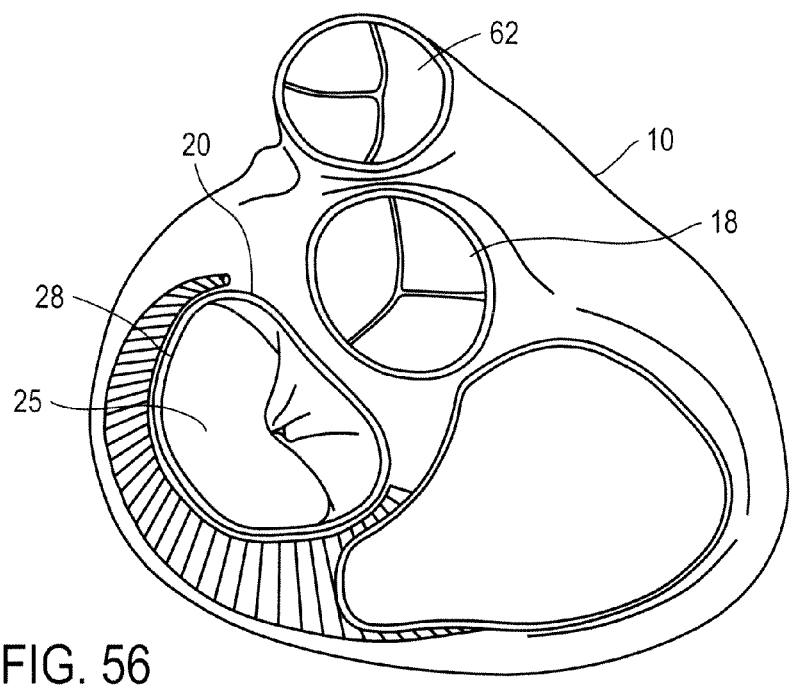
FIGS. 56-57 illustrate a normal mitral valve and an enlarged mitral valve, respectively.
Figure 57:
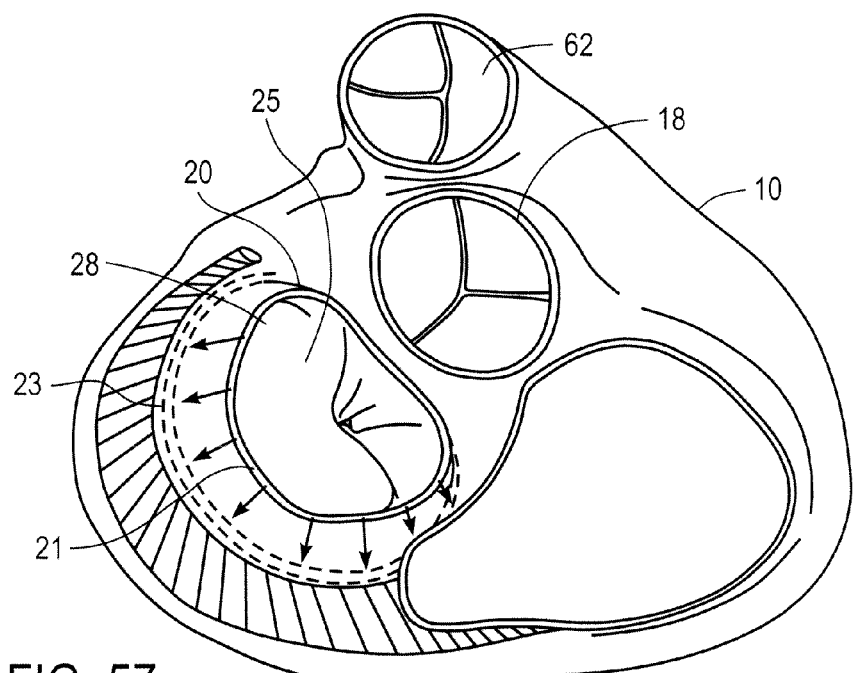
Figure 58:
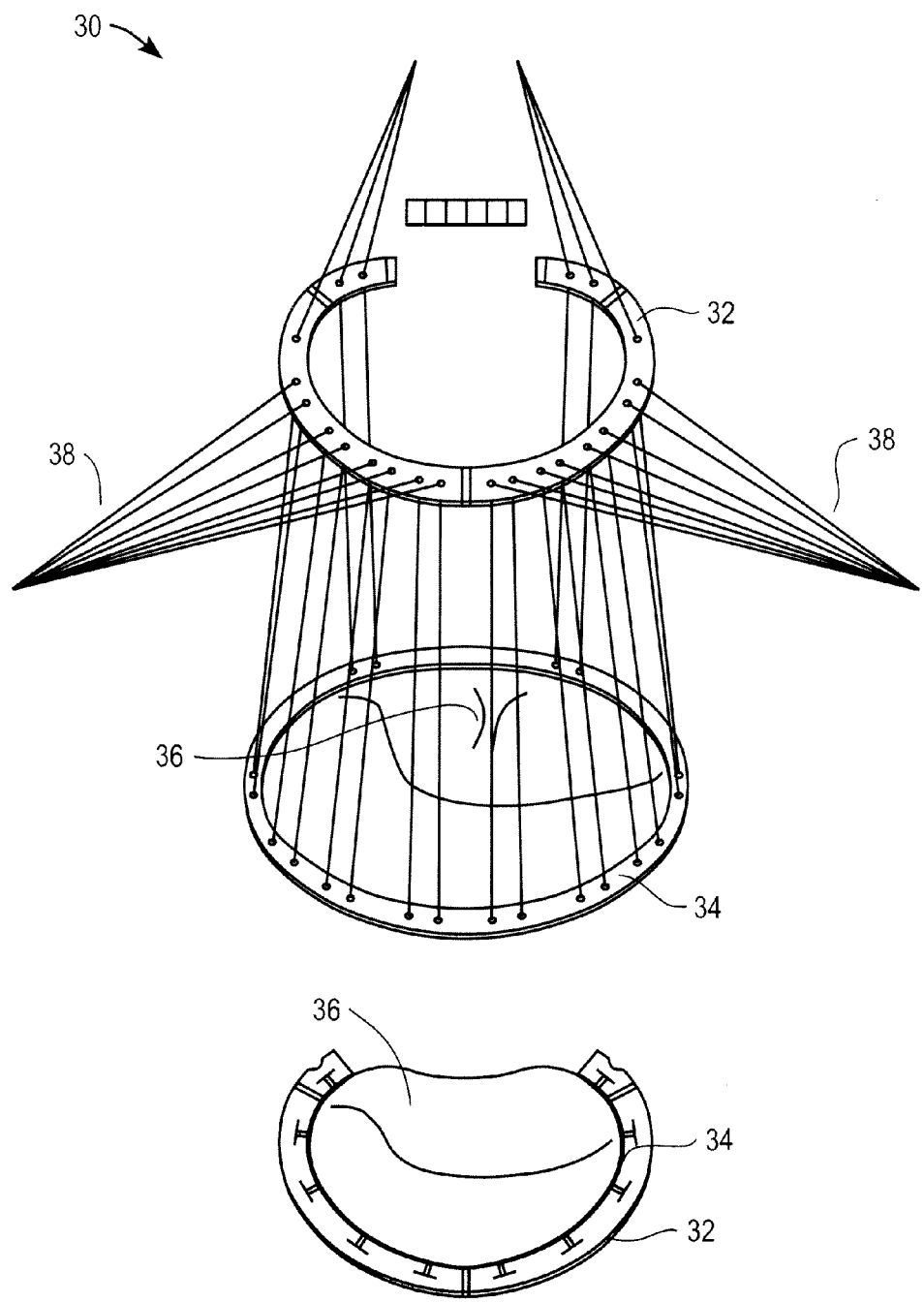
FIG. 58 is an illustration of a conventional annuloplasty procedure to constrict a valve (e.g., a mitral valve)
Figure 59:
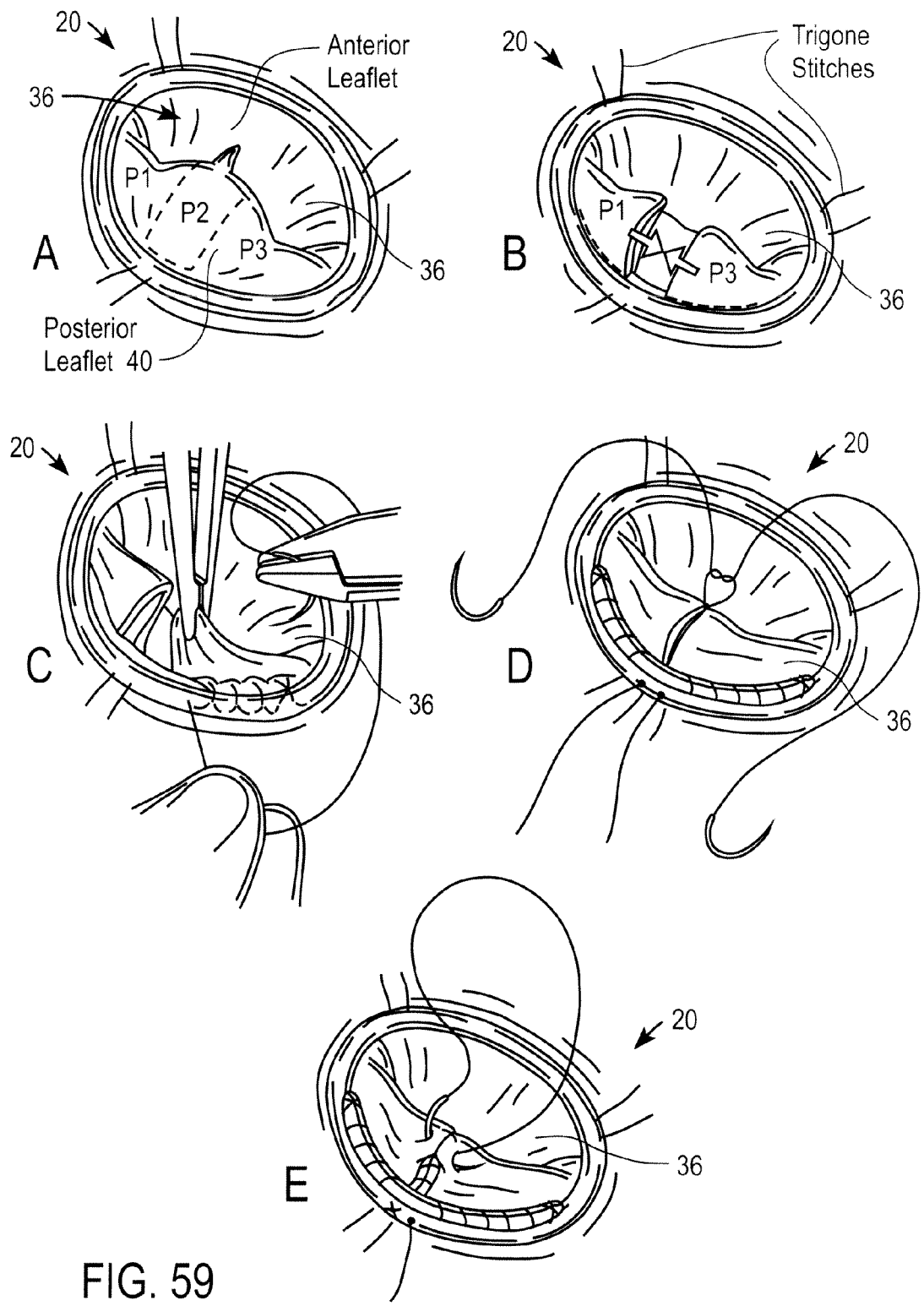
FIG. 59 is an illustration of a reconstruction procedure to reduce the size of a defective valve.
Figure 60:
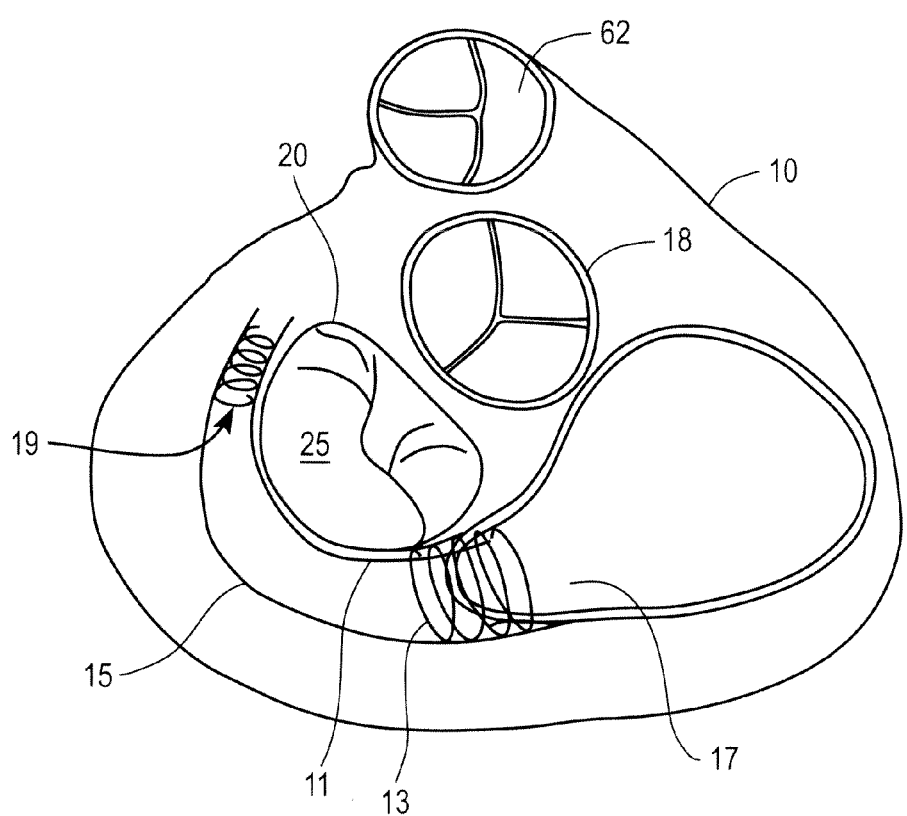
FIG. 60 illustrates how a device is deployed in a coronary sinus to reshape a mitral valve annulus.

FIGS. 53-54 illustrate an exemplary method 510 of deploying a device having a distal anchoring member and a proximal anchoring member in a vessel. At operation 512, an implantable device is provided. The device has a distal anchoring member and a proximal anchoring member connected to one another by a connecting member. At operation 514, the device is advanced into a vessel while the device is housed in a retractable (delivery) sheath. At operation 516, the proximal anchoring member is deployed at a proximal location in the vessel. The connecting member is then placed along a side of the vessel toward the distal section of the vessel. At operation 518, appropriate tension is placed on the connecting member. At operation 520, the distal anchoring member is deployed at a distal location in the vessel. At operation 522, a balloon device is used to maintain tension on the connecting member while the distal anchoring member is being deployed. At operation 524, the position and/or tension of the connecting member and/or the distal anchoring member are adjusted if necessary. At operation 526, once the deployment of the proximal anchoring member, the distal anchoring member, and the connecting member is completed, the balloon device is removed.

The foregoing description describes percutaneous methods (e.g., catheter based techniques) for delivering the annuloplasty devices described herein. It will be appreciated that surgical (non-percutaneous) techniques may alternatively be used to deploy/deliver these annuloplasty device.

It is to be understood that even though numerous characteristics and advantages of various embodiments have been set forth in the foregoing description together with details of structures and function of the various embodiments, this disclosure is illustrative only. Changes may be made in detail, especially matters of structure and management of parts, without departing from the scope of the various embodiments.

We claim:

1. A longitudinally adjustable apparatus comprising:
a distal portion and a proximal portion collectively having dimensions suitable for deployment in a vessel of a patient, the distal portion comprises a distal anchoring member, a distal telescope, and a distal backbone, and the proximal portion comprises a proximal anchoring member, a proximal telescope, and a proximal backbone, wherein the distal and proximal backbones are incorporated into the apparatus such that the distal and proximal backbones provide a structural support to the distal and proximal telescopes while providing flexibility to the apparatus, wherein the distal telescope and the proximal telescope are dimensioned to slide one in and out of the other;
a cord member coupled to the distal portion and longitudinally disposed within said distal and proximal telescopes, wherein applying a force on the cord in a proximal direction modifies a length dimension of the apparatus; and
a locking mechanism coupled to the proximal portion, the locking mechanism is configured to lock said cord into a position.

2. The apparatus of claim 1 further comprising:
a proximal adapter configured to deploy said proximal anchoring member and said distal anchoring member, wherein said proximal adapter comprises at least one locking device configured to perform one or more of preventing accidental deployment of the distal anchoring member and the proximal anchoring member, preventing accidental adjustment of the cord, and preventing accidental release of the apparatus.

3. The apparatus of claim 1 wherein said distal backbone provides an attachment point for said cord and comprises a spring-like section configured to support the distal telescope.

4. The apparatus of claim 1 wherein the proximal portion and the distal portion are further characterized in that
- said distal backbone comprises an attachment point for said cord member, comprises a distal anchor attachment section for said distal anchoring member to couple thereto, and comprises a spring-like section configured to support the distal telescope, wherein the attachment point, the distal anchor attachment section, and the spring-like section are made from a single tubing member cut into desired structures, and
- said proximal backbone comprises a proximal anchor attachment section for said proximal anchoring member to couple thereto and another spring-like section configured to support the proximal telescope, wherein the proximal attachment section and the spring-like section are made from a single tubing member cut into desired structures.

5. The apparatus of claim 4 wherein each of said spring-like sections includes a jacket capable of eluting a bioactive agent selected to perform one or more of limiting clot formation and encouraging tissue ingrowths or a combination thereof.

6. The apparatus of claim 4 wherein each of said distal and proximal anchoring attachment sections is further configured to provide flexibility along with support for each of said distal and proximal anchoring members, respectively.

7. The apparatus of claim 1 wherein said proximal backbone further comprises an attachment section for said locking mechanism to couple thereto.

8. The apparatus of claim 1 wherein said locking mechanism is coupled to said proximal portion at a position distal to said proximal anchoring member.

9. The apparatus of claim 1 further comprises a telescoping stop coupled to the distal portion of the apparatus.

10. The apparatus of claim 9 wherein the telescoping stop is configured to not protrude beyond a maximum radial expansion of the apparatus such that when said apparatus is fully deployed against a vessel wall, said telescoping stop does not engage said vessel wall.

11. The apparatus of claim 1 wherein each one of said proximal anchoring member and said distal anchoring member is a self expandable structure.

12. The apparatus of claim 1 wherein one or both of said proximal anchoring member and said distal anchoring member comprises at least one anchor, said anchor configured to fix said proximal anchoring member or said distal anchoring member in place.

13. The apparatus of claim 1 wherein said distal anchoring member and said distal backbone are made from one tubing member cut to into desired configurations to form said distal anchoring member and said distal backbone, and wherein said tubing member is further cut to provide a connection portion between the distal anchoring member and the distal backbone.

14. The apparatus of claim 1 wherein said proximal anchoring member and said proximal backbone are made from one tubing member cut to into desired configurations to form said proximal anchoring member and said proximal backbone, and wherein said tubing member is further cut to provide a connection portion between the proximal anchoring member and the proximal backbone.

15. The apparatus of claim 1 further comprises an outer housing for said locking mechanism, said outer housing couples to said proximal portion, wherein said proximal anchoring member, said proximal backbone, and said outer housing are made from one tubing member cut to into desired configurations for said proximal anchoring member, said proximal backbone, and said outer housing, and wherein said tubing member is further cut to provide a connection portion between the proximal anchoring member and the outer housing for said locking mechanism.

16. The apparatus of claim 1 further comprising:
- a proximal adapter releasably coupled to said apparatus and configured to deploy said proximal anchoring member and said distal anchoring member, wherein said proximal adapter comprises at least one locking device configured to perform one or more actions selected from the group consisting of preventing accidental deployment of the distal anchoring member and the proximal anchoring member, preventing accidental adjustment of the cord, and preventing accidental release of the apparatus; and
- a delivery sheath coupled to said proximal adapter and having a longitudinal movement controlled by said proximal adapter, said delivery sheath is disposed and movable over said proximal anchoring member and said distal anchoring member during deployment, wherein said delivery sheath keeps said proximal anchoring member and said distal anchoring member in collapsed states until deployment.

17. The apparatus of claim wherein said delivery sheath further comprises an atraumatic distal tip sealable during delivery and breakable during retraction to deploy said proximal anchoring member and said distal anchoring member.

18. The apparatus claim 1 wherein each of said distal and proximal backbones has cut-out sections.

19. The apparatus of claim 1 wherein said cord member is longitudinally constrained to one side of said apparatus.

20. The apparatus of claim 1 wherein said distal portion and said proximal portion are configured to further be adjustable in curvature.

21. The apparatus of claim 1 wherein said distal portion and said proximal portion are configured with a preset curvature such that once deployed, said distal portion and said proximal portion conform to said curvature.

22. The apparatus of claim 1 wherein one or both of said distal and proximal anchoring members is configured to comprise an attachment spine for coupling to respective distal and proximal portion of said apparatus, the attachment spine comprises attachment points for attaching to said respective distal and proximal backbones.

23. The apparatus of claim 1, wherein the apparatus has dimensions suitable for deployment in a coronary sinus vessel of a patient.

24. The apparatus of claim 23, wherein applying a force on the cord in a proximal direction, shortens a length of the apparatus.

25. The apparatus of claim 1, wherein applying a force on the cord in a proximal direction, shortens a length of the apparatus.

26. A longitudinally adjustable apparatus comprising:
- a distal portion and a proximal portion having dimensions suitable for deployment in a vessel of a patient, and a cord member working in conjunction to provide a longitudinal adjustment for said apparatus, the distal portion comprises a distal anchoring member, a distal telescope, and a distal backbone, and the proximal portion comprises a proximal anchoring member, a proximal telescope, and a proximal backbone, wherein the distal and proximal backbones are incorporated into the apparatus such that the distal and proximal backbones provide a structural support to the distal and proximal telescopes while providing flexibility to the apparatus, wherein the distal telescope and the proximal telescope are dimensioned to slide one in and out of the other, and wherein a cord member is longitudinally disposed along said distal and proximal telescopes to facilitate adjustability for the apparatus; and a locking mechanism coupled to the proximal portion, the locking mechanism is configured to lock said cord into a position, and wherein said distal telescope, said proximal telescope, and said cord member are configured such that when working in conjunction, said distal telescope and proximal telescope slide off each other completely with a portion of said cord member exposed between said distal telescope and said proximal telescope.

27. The apparatus of claim 26 wherein said cord member comprises sections of different thicknesses and a set of bumps.

28. The apparatus of claim 27 wherein said bumps, said sections of different thicknesses and said distal and proximal telescopes work in conjunction to control a total length for said apparatus.

* * * * *